(12) United States Patent
Theander et al.

(10) Patent No.: US 7,745,580 B2
(45) Date of Patent: Jun. 29, 2010

(54) COMPOUNDS USEFUL IN THE DIAGNOSIS AND TREATMENT OF PREGNANCY-ASSOCIATED MALARIA

(75) Inventors: Thor Grundtvig Theander, Ishøj (DK); Ali Salanti, Copenhagen (DK); Lars Hviid, Copenhagen S (DK); Trine Staalsø, Copenhagen NV (DK); Anja Tatiana Ramstedt Jensen, Brønshøj (DK); Thomas Lavstsen, Copenhagen Ø (DK); Madelaine Dahlbäck, Malmö (SE)

(73) Assignee: Kobenhavns Universitet, Copenhagen (DK)

( * ) Notice: Subject to any disclaimer, the term of this patent is extended or adjusted under 35 U.S.C. 154(b) by 7 days.

(21) Appl. No.: 10/543,312

(22) PCT Filed: Dec. 30, 2003

(86) PCT No.: PCT/DK03/00938

§ 371 (c)(1),
(2), (4) Date: Aug. 18, 2006

(87) PCT Pub. No.: WO2004/067559

PCT Pub. Date: Aug. 12, 2004

(65) Prior Publication Data

US 2007/0053928 A1    Mar. 8, 2007

(30) Foreign Application Priority Data

Jan. 27, 2003  (DK)  .................. PA 2003 00102

(51) Int. Cl.
*A61K 39/00* (2006.01)
*C07K 1/00* (2006.01)
*C07K 2/00* (2006.01)

(52) U.S. Cl. .................... 530/350; 530/300; 424/185.1; 435/975

(58) Field of Classification Search .................. 530/350
See application file for complete search history.

(56) References Cited

FOREIGN PATENT DOCUMENTS

| WO | WO 00/25728 A | 5/2000 |
|----|---------------|--------|
| WO | WO 01/16326 A | 3/2001 |
| WO | WO0116326 * | 3/2001 |
| WO | WO0116326 A2 * | 3/2001 |

OTHER PUBLICATIONS

Michal Fried et al., "Maternal antibodies block malaria", Nature, vol. 395, Oct. 29, 1998, pp. 851-852.
Malcolm J. Gardner et al., "Genome sequence of the human malaria parasite *Plasmodium falciparum*", Nature vol. 419, 2002, pp. 498-511.
Thomas Lavstsen et al., "Sub-grouping of *Plasmodium falciparum* 3D7 var genes based on sequence analysis of coding and non-coding regions", Malaria Journal, 2003,2, pp. 1-14.
Iona O'Neil-Dunne et al., "Gravidity-Dependent Production of Antibodies That Inhibit Binding of *Plasmodium falciparum*-Infected Erythorocytes to Placental Chondroitin Sulfate Proteoglycan during Pregnancy", Infection and Immunity, Dec. 2001, pp. 7487-7492.
Bridget A. Robinson et al., "Widespread functional specialization of *Plasmodium falciparum* erythrocyte membrane protein 1 family members to bind CD36 analysed across a parasite genome", Molecular Microbiology (2003) 47(5), 1265-1278.
C.E. Shulman et al., "Malaria in pregnancy: adverse effects on haemoglobin levels and birthweight in primigravidae and multigravidae", Tropical Medicine and International Health, vol. 6, No. 10, pp. 770-778, Oct. 2001.
Joseph D. Smith et al., "Classification of adhesive domains in the *Plasmodium falciparum* Erythrocyte Membrane Protein 1 family", Molecular and Biochemical Parasitology 110 (2000) 293-310.
Joseph D. Smith et al., "Switches in Expression of *Plasmodium falcimparum* var Genes Correlate with Changes in Antigenic and Cytoadherent Phenotypes of Infected Erythrocytes", Cell, vol. 82, 101-110, Jul. 14, 1995.

(Continued)

*Primary Examiner*—Mark Navarro
(74) *Attorney, Agent, or Firm*—Stephen A. Bent; Foley & Lardner LLP

(57) ABSTRACT

The present invention relates to nucleic acid molecules related to the var2csa gene family as well as amino acid sequences encoded by such nucleic acid molecules with respect to their role in mediating adhesion of infected red blood cells to chondroitin sulphate A (CSA) in the placenta which is characteristic for the pathogenesis of pregnancy associated malaria (PAM). Accordingly, The invention provides the use compounds that are related to VAR2CSA polypeptides var2csa nucleic acid molecules as medicaments, as well as it provides pharmaceutical compositions, in particular immunological compositions and vaccines, hereunder nucleotide-based vaccines comprising these compounds. In addition, the invention provides the use of the compounds mentioned for the manufacture of compositions, such as immunogenic compositions. Other aspects of the invention relates to methods of treatment and prevention of pregnancy associated malaria wherein these methods are based on the nucleic acid molecules and polypeptides the invention. As these compounds can also be used as biotechnological tools the invention provides in vitro diagnostic methods and kits comprising reagents and IgGs/antibodies designated to the use in such methods. The invention also relates to methods of identifying agents capable of modulating the VAR2CSA dependent adhesion to CSA and agent capable of interacting with VAR2CSA. Finally, a method for identifying polypeptides, which will induce a specific IgG/antibody response upon administration to a subject is provided by the invention.

7 Claims, 19 Drawing Sheets

OTHER PUBLICATIONS

Figure 9:
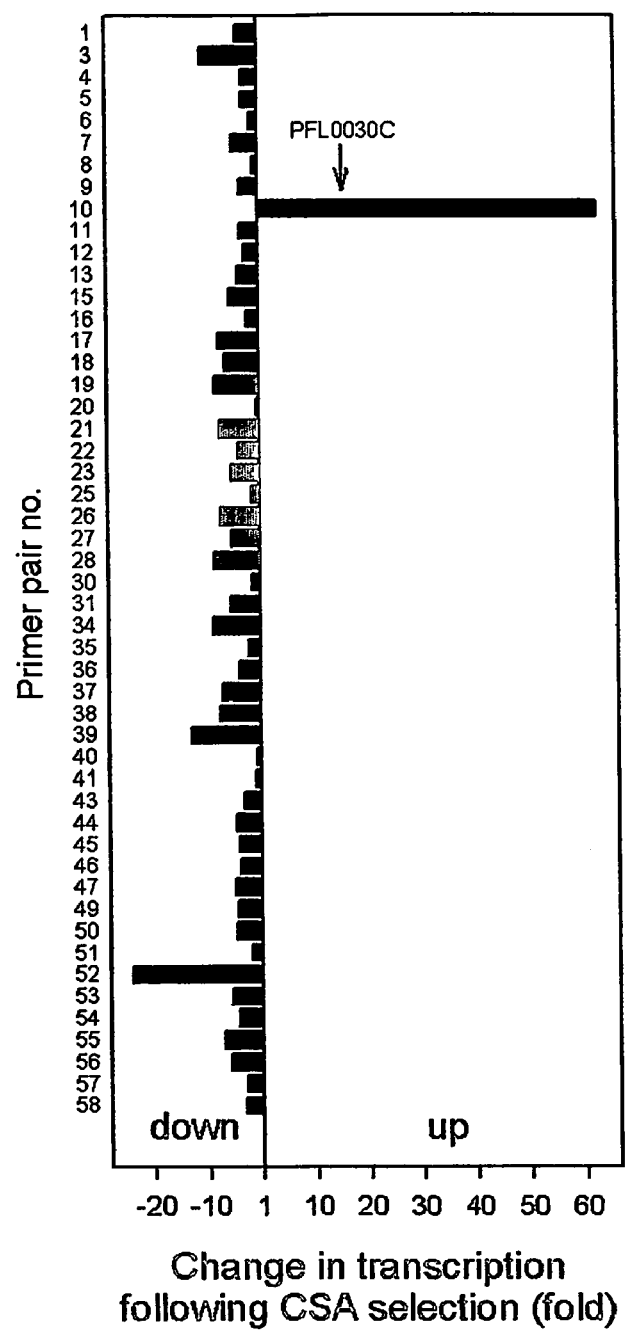

Trine Staalsoe et al., "Detection of Antibodies to Variant Antigens on *Plasmodium falciparum*-Infected Erythrocytes by Flow Cytometry", Cytometry, 35:329-336 (1999).

Mats Wahlgren et al., "Waves of Malarial Var-Iations", Cell, vol. 96, pp. 603-606, Mar. 5, 1999.

Database EMBL 'Online!, Oct. 3, 2002, M.J. Gardner et al., "*Plasmodium falciparum* 3D7 chromosome 12 section 1 of 9 of the complete sequence".

Database EMBL 'Online! Jul. 20, 2002, K. Tang et al., PfESToab46901.y1 *Plasmodium falciparum* 3D7 asexual cDNA *Plasmodium falciparum* cDNA 5' similar to TR:Q26030 Q26030 Variant Surface Protein;, mRNA sequence.

Ali Salanti et al., "A sub-family of common and highly conserved *Plasmodium falciparum* var genes", Molecular & Biochemical Parasitology vol. 122, No. 1, Jun. 2002, pp. 111-115.

Patrick Duffy et al., "Variant proteins on the surface of malaria-infected erythrocytes: Developing vaccines", Trends in Parasitology, vol. 17, No. 8, Aug. 2001, pp. 354-356.

Pierre A. Buffet et al., "*Plasmodium falciparum* domain mediating adhesion to chondroitin sulfate A: A receptor for human placental infection", Proceedings of the National Academy of Sciences of USA National Academy of Science, Washington, US, vol. 96, No. 22, Oct. 26, 1999, pp. 12743-12748.

C. H. Ricke et al., "Plasma antibodies from malaria-exposed pregnant women recognize variant surface antigens on *Plasmodium falciparum*-infected erythrocytes in a parity-dependent manner and block parasite adhesion to chondroitin sulfate A", Journal of Immunology (Baltimore MD: 1950), US, Sep. 15, 2000, vol. 165, No. 6, pp. 3309-3316.

Trine Staalsoe et al., "Acquisition and decay of antibodies to pregnancy-associated variant antigens on the surface of *Plasmodium falciparum*: Infected erythrocytes that protect against placental parasitemia", Journal of Infectious Diseases, vol. 184, No. 5, 2001, pp. 618-626.

Ali Salanti et al., "Selective upregulation of a single distinctly structured var gene in chondroitin sulphate A-adhereing *Plasmodium falciparum* involved in pregnancy-associated malaria", Molecular Microbiology, vol. 49, No. 1, Jul. 20, 2003, pp. 179-191.

* cited by examiner

A.
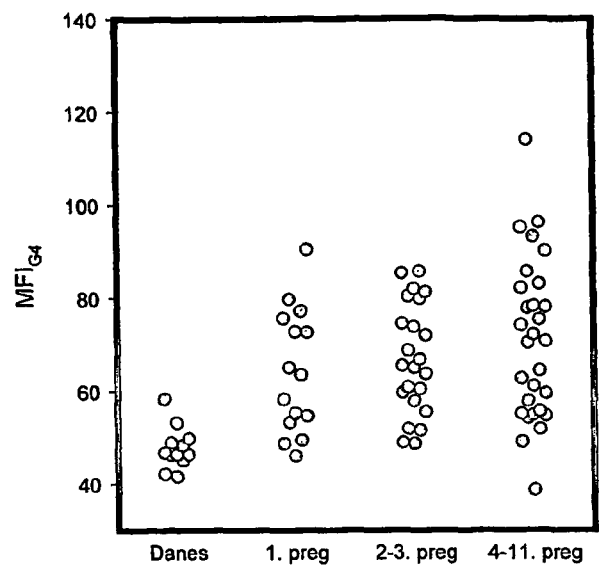
B.
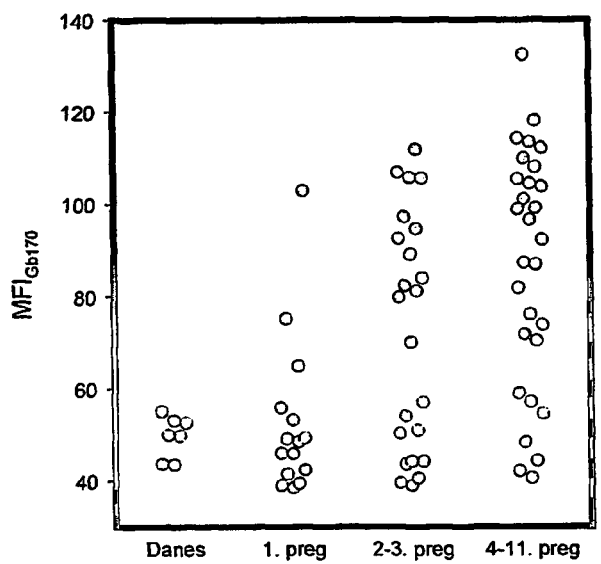
Fig. 1

A.
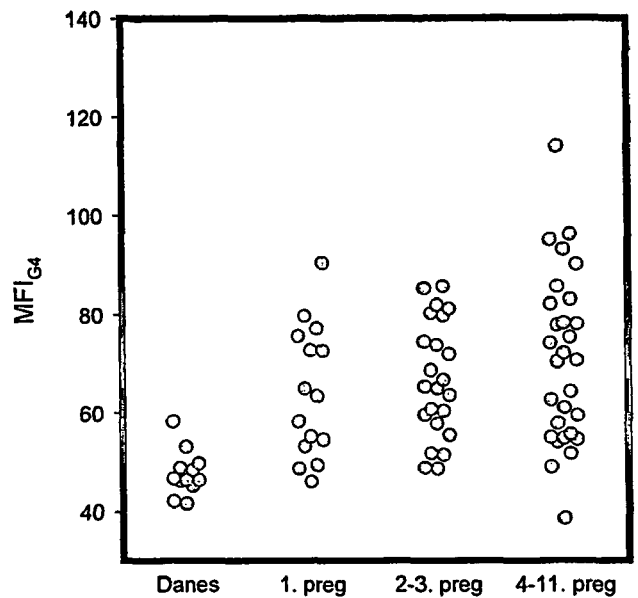
B.
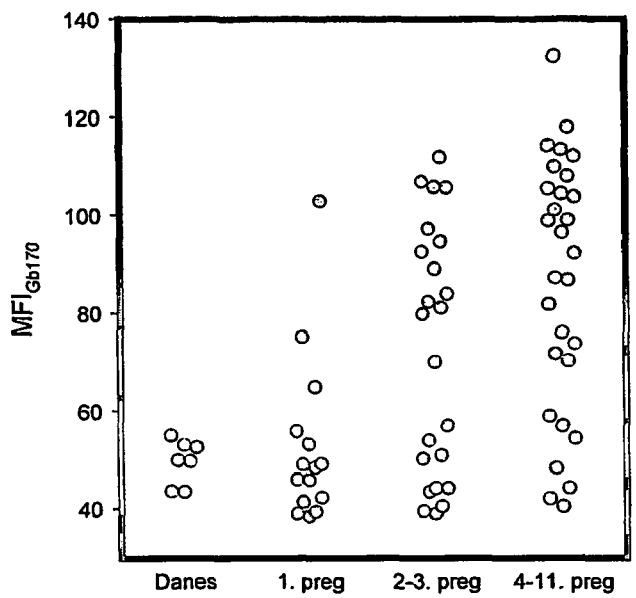
Fig. 2

A.
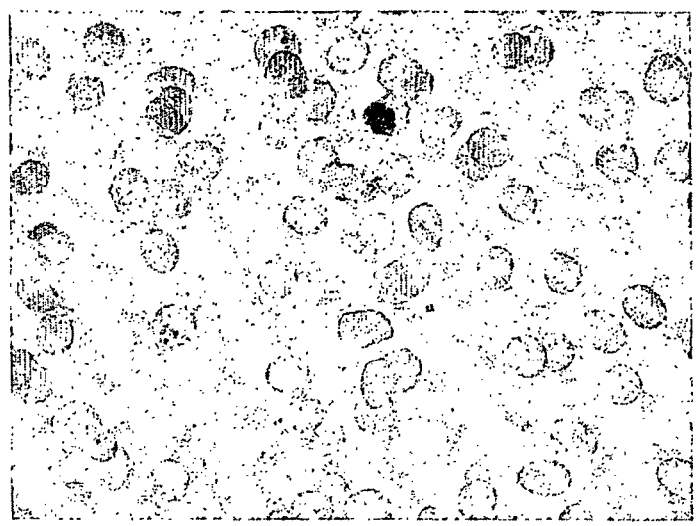
B.
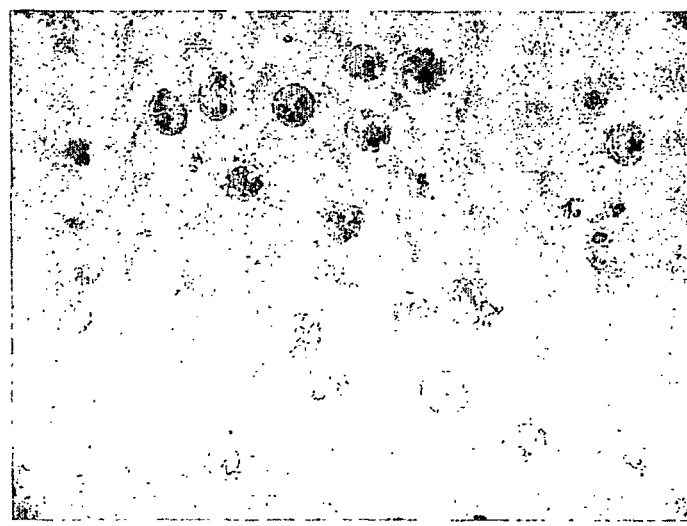
Fig. 3

A.
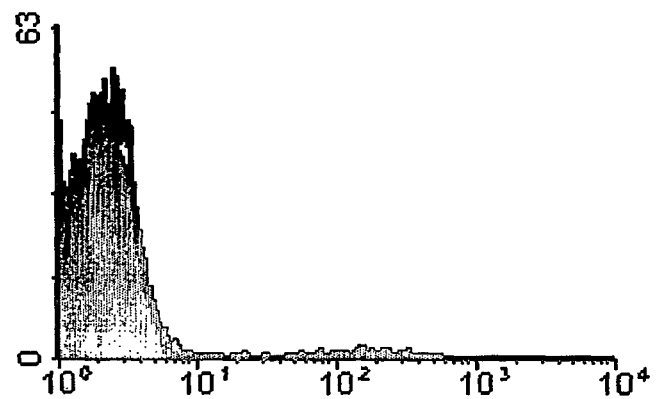
B.
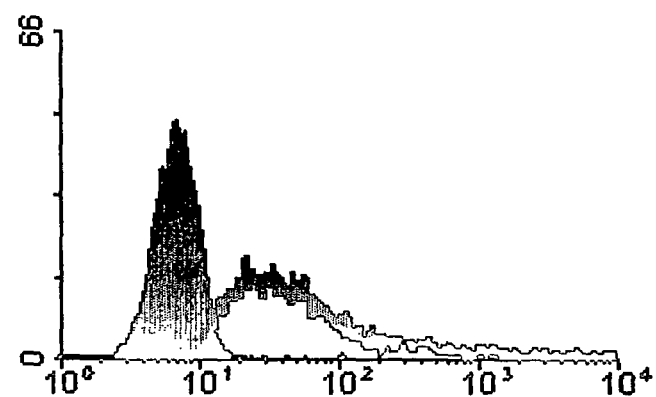
Fig. 4

A.
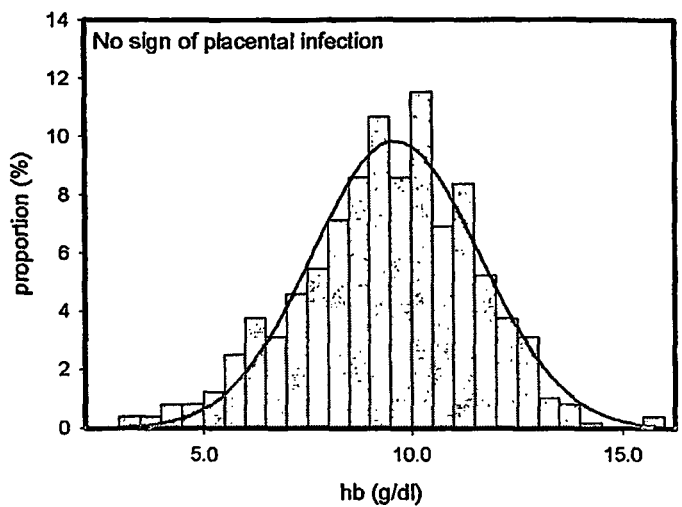
B.
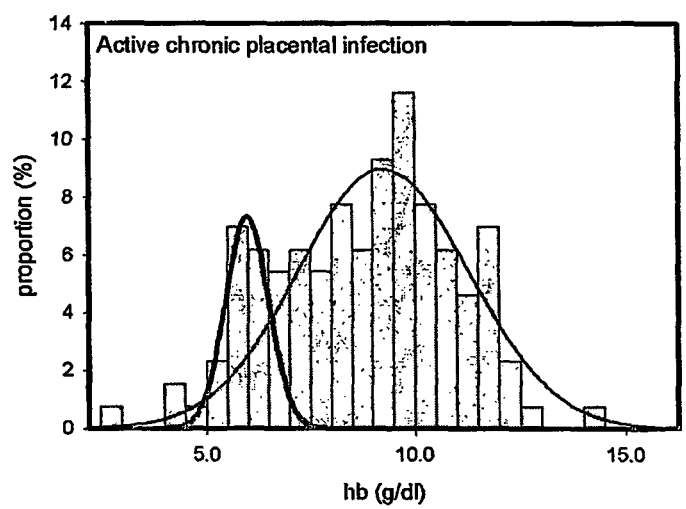
Fig. 5

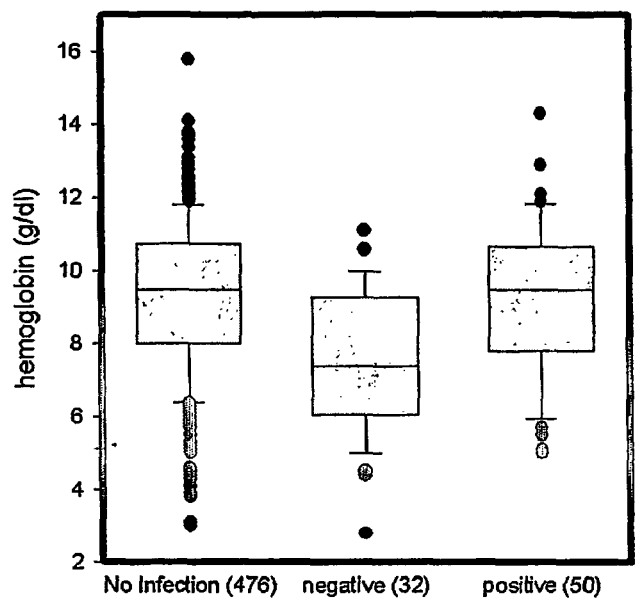
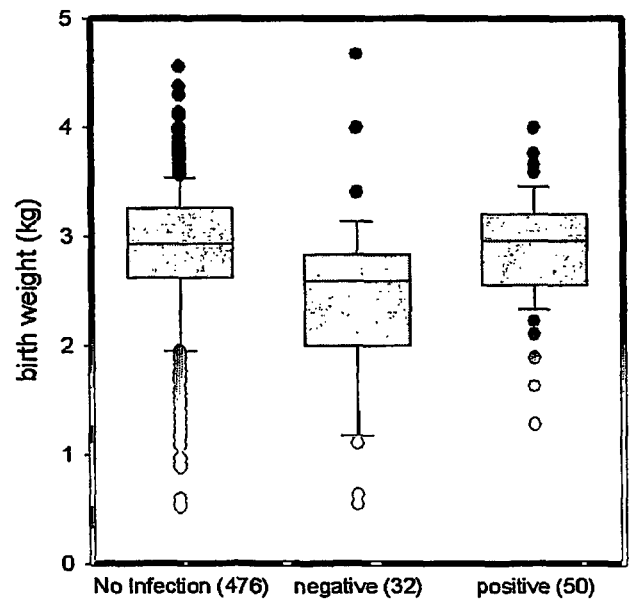
Fig.6

A.
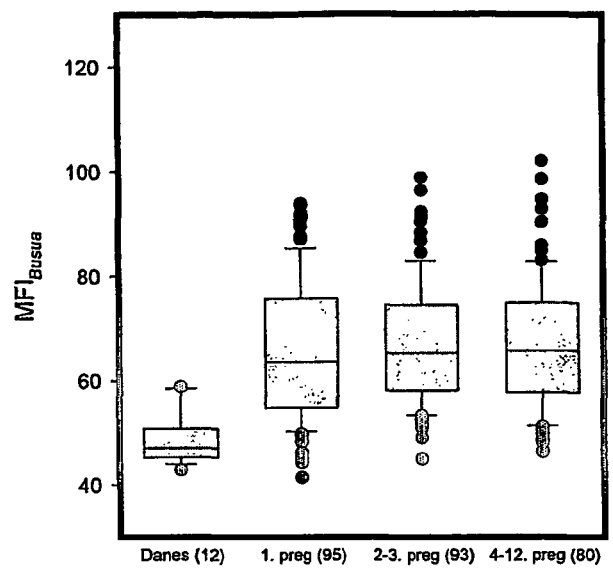
B.
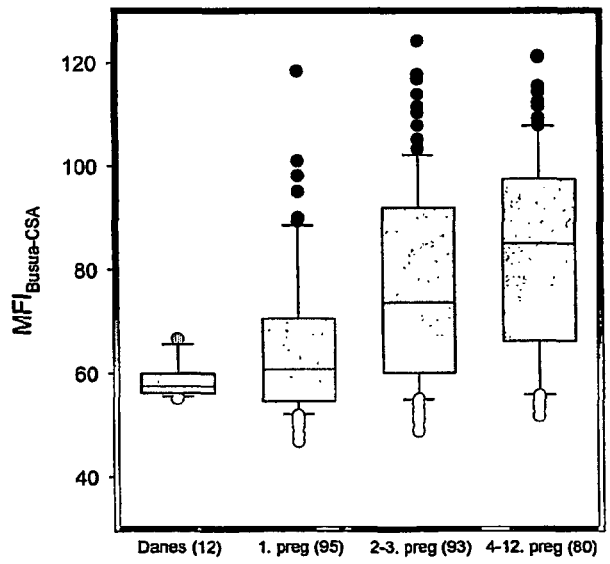
Fig. 7

A. *msp1* K1
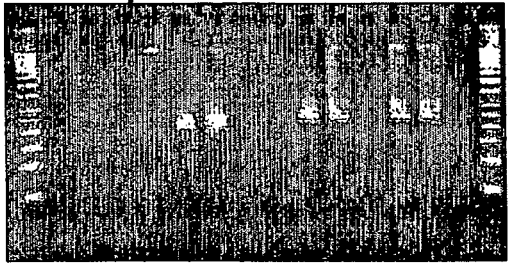
D. *msp2* IC1
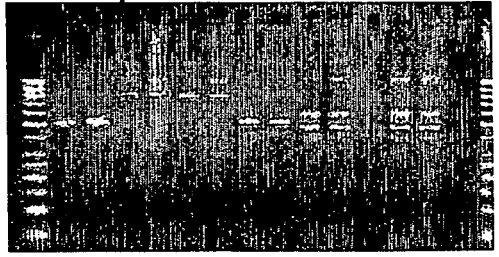
B. *msp1* MAD20
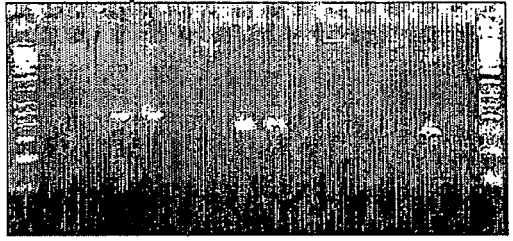
E. *msp2* FC27
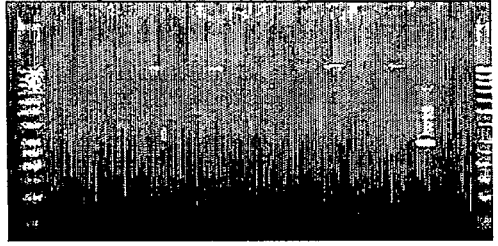
C. *msp1* RO33
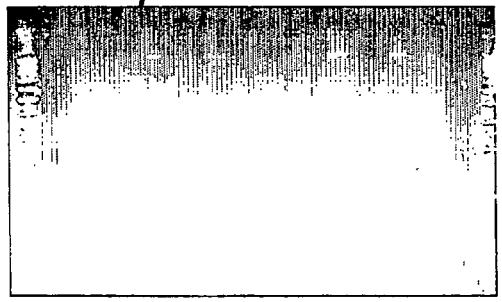
F. *glurp*
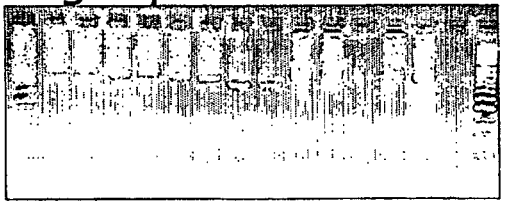
Fig.8

Fig. 10

A

```
2o2var2csa  CQDFLRILQENCSDNKRGSSSNGSCDKNSEEICQKKLENVEASLTNCYKCDKCKSEQSKKQNNKWIWKKYSGNGEGLQKEYA
3d7var2csa  CQDFLRILQENCSDNKSGSSSNGSCNNKQEACEKNLEKVLASLTNCYKCDKCKSEQSKKNNKNWIWKKSSGKEGGLQKEYA 2o2var2csa  NTIGLPPRTQSLCLVCLHEKEGK--TQHKTISTNSELLKEWIIAAFHEGKNLKKRYPQNKNDDNNSKLCKALEYSFADYGDL
3d7var2csa  NTIGLPPRTQSLCLVVCLDEKGKKTQELKNIRTNSELLKEWIIAAFHEGKNLKPSHEK-KNDDNGKKLCKALEYSFADYGDL 2o2var2csa  IKGTSIWDNEYTKDLELNLQKAFGKLFRKYIKKNNTAEQDTSYSSLDELRESWWNTNKKYIWTAMKHGADMNGTTCS-SGSG
3d7var2csa  IKGTSIWDNEYTKDLELNLQKIFGKLFRKYIKKNNTAEQDTSYSSLDELRESWWNTNKKYIWLAMKHGAGMNSTTCCGDGSV 2o2var2csa  DNGDSSGCDDIPIIDIIEPQYLRELQDWVEHFCKQRQAKVKDVINSGNSGKNTSGERKIGGTGNSDGCKKQRVAGDAVKTEDED
3d7var2csa  TGSGSSGCDDIPTDDLIEPQYLREFQDWVNEHFCKQRQEKVMPVHENCKSCKES------GGTGNGECKTPCKNKGEVVKKIEED 2o2var2csa  QRTAVGGTAGSSWVKRWDQIMKRYSKHIEDAKRNRKAGTGNCGPSSTTNAADNKCVQSDIDSPEKHLEDIGITTPSSYLSNM
3d7var2csa  CKGGDC-TAGSSWMKRWDQIMKRYSKYLEDAKRNRKAGTKNCGPSSTLNAAENKGVQSDIDSHEKHLEDIGITTESSYLSIM 2o2var2csa  LDENSCGADKAPWTTYTTYTTYTTYTTYTTTEKCNKERDKSKSQQSNTSVVVNVPSPLGNTPHEYKYACECKIPTTEETCDD
3d7var2csa  LDDNICGADKAPWTTYT---------TYTTTEKCNKETDKSKLQQONTAVVVNVPSPLGNTPHGYKYACCKIPTNEETCDD 2o2var2csa  RKEYMNQWIIDNTKNPKGSCSTDNDYELYTYNGVQIKQAAGRSSSTKLDENDVMFFNLFEQWNKEIQY EIEQYMTNANISCNN
3d7var2csa  RKEYMNQWSCGSARTMKR-GYKNDNYELCKYNGVDVKPTTVRSNSSKLDDKDVTFFNLFEQWNKEIQY QIEQYMTNTKISCNN
```

B

```
2o2var2csa  DMKVSETSCDLNATNYIRGCQSRTYDGKIFPGKGGEKQGICKDTIIHGDTNGACIPPRTQNLCVGNLWDKSYGGRSNIKNDTKE
3d7var2csa  KMKSSETSCDCSEPIYIRGCQPKIYDGKIFPGKGGEKQWICKDTIIHGDTNGACIPPRTQNLCVGELWDKRYGGRSNIKNDTKE 2o2var2csa  SLKNKLKNAIQKETELLYEYHDKGTAIISKNDKKGQKEKEEKNNDSNGLPKGFCHAVQRSFIDYKNMILGTSVNIYEYIGKLQE
3d7var2csa  SLKQKIKNAIQKETELLYEYHDKGTAIISRNEMKGQKEKEEKNNDSNGLPKGFCHAVQRSFIDYKNMILGTSVNIYEYIGKLQE 2o2var2csa  DIKKIIECGTPQQKDKTVG-GAENVNAWWKDIEREMWGAVKCGITKINKK-KKNGTENVDECGVSPSTGNDEDQSVSWF
3d7var2csa  DIKKIIEKGTTKQNGKTVGSGAENVNAWWKGIEGEMWDAVRCAITKINKKQKKNGTFSIDECGIFPPTGNDEDQSVSWF
```

Fig.14

A

```
BM033  CSEPIYIRGCQPKIYDGKIPPGKGGEKQWICKDTIIHGDTNGACIPPRTQNLCVGNLWYKSYGGRSNIKNETKESLKNKDKNAIQKET
BM074  CSEPIYIRGCQPKIYDGKIFPGKGGEKKWICKDTIIHGDTNGACIPPRTQNLCVGELWYKSYGGRSNIKNDTKESLKNKDKNAIQKET
BM078  CSEPIYIRGCQPKIYDGKILPGKGGEKQWICKDTIIHGDTNGACIPPRTQNLCVGELWDKSYGGRSNIKNETKESLKQKDKNAIQKET
EJ021  CSEPIYIRGCQPKIYDGTISPGKGGEKQWICKDTIIHGDTNGACIPPRTQNLCVGELWYKSYGGRSNIKNDTKESLKNKDKNAIQKET
EJ023  CSEPIYIRGCQSKIYDGTISPGKGGEKQWICKDTIIHGDTNGACIPPRTQNLCVGELWYKSYGGRSNIKNDTKESLKNKDKNAIQKET
EJ017  CSEPIYIRGCQSKIYDGKIFPGKGGEKQWICKDTIIHGDTNGACIPPRTQNICVGELWDKSYGGRSNIKNDTKESLKNKDKNAIQKET
EJ010  CSEPIYIRGCQPKIYDGKIPPGKGGEKQWICKDTIIHGDTNGACIPPRTQNLCVGELWDKRYGGRSNIKNDTKESLKQKDKNAIQKET
3D7    CSEPIYIRGCQPKIYDGKIFPGKGGEKQWICKDTIIHGDTNGACIPPRTQNLCVGELWDKRYGGRSNIKNDTKESLKQKDKNAIQKET

BM033  ELLYEYHDKGTAIIS
BM074  ELLYEYHDKGTAIIS
BM078  ELLYEYHDKGTAIIS
EJ021  ELLYEYHDKGTAIIS
EJ023  ELLYEYHDKGTAIIS
EJ017  ELLYEYHDKGTAIIS
EJ010  ELLYEYHDKGTAIIS
3D7    ELLYEYHDKGTAIIS
```

B

```
BM033  GQGDKIQGACKRKCEEYKKYISEKKQEWDKQKTKYENKYVGKSASDLLKENYPECISANFDFIFNNNIEYKTYYPYGDYSSICSCEQV
BM074  GQGDKVEGACKRKCEEYKKYISEKKQEWDKQKTKYENKYVGKSASDLLKENYPECISANFDFIFNDNIEYKTYYPYGDYSSICSCEQV
BM078  GQGDKIQGDCKRKCEEYKKYISEKKQEWDKQKTKYENKYVGKSASDLLKENYPECISANFDFIFNDNIEYKTYYPYGDYSSICSCEQV
EJ021  GQGDKVEGACKRKCEEYKKYISEKKQEWDKQKTKYENKYVGKSASDLLKENYPECISANFDFIFNDNIEYKTYYPYGDYSSICSCEQV
EJ023  GQEDKVEGACKRKCEEYKKYISEKKQEWDKQKTKYENKYVGKSASDLLKENYPECISANFDFIFNDKADEKYYPYGDYSSICSCEQV
EJ017  GQEDKIQGACKRKCEKYKKYISEKKQEWDKQKTKYENKYVGKSASDLLKENYPECISANFDFIFNDNIEYKTYYPYGDYSSICSCEQV
EJ010  GQGDKIQGDCKRKCEEYKKYISEKKQEWDKQKTKYENKYVGKSASDLLKENYPECISANFDFIFNDNIEYKTYYPYGDYSSICSCEQV
3D7    GQGDKIQGDCKRKCEEYKKYISEKKQEWDKQKTKYENKYVGKSASDLLKENYPECISANFDFIFNDNIEYKTYYPYGDYSSICSCEQV
```

Fig.15

SEQUENCE LISTING

<160> NUMBER OF SEQ ID NOS: 3

<210> SEQ ID NO 1
<211> LENGTH: 9171
<212> TYPE: DNA
<213> ORGANISM: Plasmodium falciparum

<400> SEQUENCE: 1
atggataaat caagtattgc taacaaaatt gaagcatatt taggtgcaaa atccgatgat        60

```
tctaaaatag accaatcgtt gaaagctgat cctagtgaag tgcagtacta tggaagtgga    120
ggtgatggat attacttaag aaaaaatatt tgcaaaatta ccgtgaatca ttcagattct    180
ggaacaaatg atccttgtga tagaatacca cctccttatg gcgataatga ccaatggaaa    240
tgtgccataa ttttatctaa agtaagtgaa aaacctgaaa atgtatttgt tcctccgaga    300
agacaacgta tgtgcattaa caatttagaa aaattaaatg ttgataaaat tagggataaa    360
catgcatttt tggcagatgt attacttacg gccagaaatg aaggagaaag aatagtgcag    420
aatcatccag atacaaatag ttccaatgtt tgtaatgcat tagaaagaag ttttgctgac    480
attgcagata ttattagagg tacagatcta tggaaaggta ctaatagtaa tttagaacaa    540
aatttaaaac aaatgtttgc aaaaatacga gaaacgaca aggtacttca agataaatac    600
ccaaaggacc aaaattatag aaaattacga gaagattggt ggaatgctaa tagacaaaag    660
gtgtgggaag ttattacttg tggtgcgcga agtaacgatt tactcataaa acgtggatgg    720
agaacatctg gaaatctaa tggagacaat aaacttgaat tgtgtcgcaa atgtggccat    780
tatgaagaaa aggttcctac caaattagat tatgtccctc aattcttaag gtggttaaca    840
gaatggatag aggatttta tagagagaag caaaatctga tcgatgacat ggagagacac    900
cgtgaagagt gtacatcaga ggatcataaa tctaaagaag gtacatcata ttgtagtacc    960
tgtaaagaca atgtaagaa atattgtgaa tgtgtgaaga atggaaatc cgaatgggaa    1020 aatcaaaaaa ataaatatac agaattatat caacaaaaca aaacgaaac ttcgcaaaaa    1080 aatacatcaa gatatgatga ttatgttaaa gatttttta aaaaacttga agctaattat    1140
tcgtctcttg aaaattatat aaagggtgat ccttatttcg cagaatatgc aaccaaatta    1200
tcatttattt taaattcatc agatgctaat aatccgtctg aaaaaataca aaaaaataat    1260
gatgaagtat gtaactgtaa tgaatcagga attgcatctg ttgaacagga acaaatatcg    1320
gatccgtcgt cgaataaaac atgtatcaca catagctcca taaaagctaa taagaaaaaa    1380
gtatgtaaac atgtaaagtt gggtgttcgt gaaaatgata agatttgag agtatgcgta    1440 attgagcaca cttccttaag tggtgttgaa aattgttgtt gccaagattt cttgcgaatt    1500
cttcaagaaa attgtagtga taataaagt ggatctagtt ctaatggtag ttgtaataac    1560
aaaaatcagg aagcatgtga aaaaaattta gaaaagtac ttgcatcttt aactaattgt    1620
tataaatgcg acaaatgtaa atctgaacaa tcaaaaaaa ataacaaaaa ttggatatgg    1680
aaaaaatcct ctggtaagga aggtggatta caaaaagaat atgctaatac aataggttta    1740
cccccaagaa cacaatcctt atgtttagta gtgtgtttag atgaaaaagg aaaaaaaaca    1800
caagaactta agaatattag gaccaattca gaattattaa aagagtggat aattgctgca    1860
tttcatgaag gaaaaaattt aaaaccttcc catgaaaaaa aaaatgatga caatggaaaa    1920
aaattatgca aagctttaga atacagtttt gccgattatg gagatttaat taaaggtaca    1980
agtatatggg ataatgaata tacaaaagat ttggaactaa atttacaaaa aatttttgga    2040 aaacttttc gtaaatatat aaaaaagaat aatactgctg aacaagatac ttcatattct    2100
tctcttgatg aattaagaga atcatggtgg aacacgaaca aaaatatat ttggttagca    2160 atgaaacatg gtgcgggaat gaatagtact acgtgttgtg gtgatggtag tgtcactggt    2220
agtggtagta gttgtgatga tattcctacg attgatttga tccctcaata tttacggttt    2280
ttgcaagaat gggtagaaca ttttttgtaaa caacgtcaag aaaaagtaaa acctgtgata    2340
gagaattgta agtcgtgtaa ggaaagtgga ggtacatgta acggtgagtg taaaactgaa    2400
tgtaaaaata aatgtgaagt atacaaaaaa tttattgaag actgtaaggg tggtgatggt    2460
```

```
actgctggat cctcatgggt gaaaaggtgg gaccaaatat ataagaggta ttccaaatat    2520
atagaagacg cgaaacgaaa ccgtaaagcg ggcacaaaaa attgtggccc aagtagtact    2580
acaaatgctg ccgaaaataa atgtgtacaa tcagatatcg attcgttttt caaacattta    2640
attgatatag gattgaccac accatcttct tatttatcta ttgttcttga tgacaacata    2700
tgtggcgcgg acaaagctcc ttggacaaca tacacgacac acacaacaac agaaaaatgt    2760
aataaagaaa cagataaatc aaagttacaa caatgtaata ctgccgtggt tgtaaatgtt    2820
ccgtctccac tgggtaacac tccacacgga tataaatacg catgccagtg taaaatacca    2880
actaatgaag aaacatgtga tgatagaaaa gaatatatga atcaatggag ttgtggtagc    2940
gcacgaacta tgaaacgtgg ttataaaaat gacaactacg aattatgtaa atataatggt    3000
gtagatgtaa aaccgacaac agttagatca aatagctcta aattagatga caaggatgtg    3060
acgttcttta atttgtttga acagtggaac aaagaaatac aatatcagat agagcagtat    3120
atgacaaata caaaaatatc gtgcaataac gagaaaaacg tattgagtag ggtgtcagac    3180
gaagctgcgc aaccaaaatt tagtgacaat gaaagagata gaaatagcat tacccatgag    3240
gataagaatt gcaaagaaaa atgtaaatgt tacagtttat ggatagaaaa aattaatgat    3300
cagtgggata aacagaaaga caattataat aaatttcaaa gaaaacaaat atatgatgca    3360
aataaaggtt ctcagaataa aaaagttgtt agtttatcta atttttgtt ttttcatgt     3420 tgggaagaat atatcaaaa atatttcaat ggcgattgga gtaaaattaa gaatatagga    3480
tctgatacgt ttgagtttct aataaaaaaa tgtggaaacg attcaggtga tggagaaaca    3540
atatttagtg aaaaattgaa taatgcagaa aaaaaatgta aggaaaatga aagtaccaat    3600
aataaaatga aatcaagtga aacatcatgt gactgtagtg aacctattta tattcgtggg    3660
tgtcaaccaa aaatttatga tggaaaaata tttccaggta aaggaggcga gaaacaatgg    3720
atatgtaaag atactataat acatggagat acaaatggtc cctgtatccc tccaagaaca    3780
caaaatttat gtgttggaga gttatgggat aaacgttatg gtggaaggag taatattaaa    3840
aatgatacaa aggaatcatt aaaacagaaa ataaaaaatg ctatacaaaa agaacggaa    3900 ttgttgtatg aataccacga taaaggtaca gcaattatat cacgaaatcc tatgaaagga    3960 caaaagaaa aagaagaaaa aaacaatgat tctaatggat taccaaaagg ttttttgtcat    4020 gctgttcaaa gaagttttat tgattataag aatatgattt tgggtaccag tgtaaatata    4080
tatgagtaca ttgaaaaatt acaagaagat ataaaaaaaa ttatcgaaaa aggaacaact    4140
aaacaaaacg gaaaaacagt tggtagtggt gcagaaaacg taaatgcttg gtggaaagga    4200
attgaggggg aaatgtggga tgcagtaaga tgtgctataa caaaaataaa taaaaaacaa    4260
aagaagaatg gtacatttag tatcgatgaa tgtgaatat tccccccaac aggaaatgat    4320
gaggatcagt ccgtttcgtg gtttaaagaa tggagcgaac agttttgtat agaacgatta    4380
caatatgaaa aaaatatacg tgacgcatgc actaataatg gtcaaggaga taaaatacaa    4440
ggagattgta aagaaaatg tgaagaatat aaaaatata tttctgaaaa aaacaagaa     4500 tgggacaaac aaaaaacaaa atatgaaaat aaatatgtag gaaaatctgc gagtgattta    4560
ttgaagaaaa attatcctga atgtatatca gcaattttg atttatatt taacgataat    4620 attgaatata aaacatatta tccatatgga gattatagca gtatatgttc gtgcgaacaa    4680
gtaaaatatt atgaatataa taatgctgag aaaaaaata ataaatctct ttgtcatgaa    4740
aaaggtaatg ataggacatg gagtaaaaaa tatataaaaa aattggaaaa tggtcgaaca    4800
```

```
ttagagggtg tatacgtccc cccaagacgg caacaattat gtctttatga actatttcca    4860
ataattataa aaaacaaaaa tgatattaca aacgcaaaaa aagaattatt ggaaacatta    4920
caaatagttg cagagcgaga agcatattat ttatggaaac agtatcatgc acataatgat    4980
acaacttatc ttgcacataa gaaagcttgt tgtgctattc gtggaagttt ttatgatttg    5040
gaagatatta ttaaaggcaa cgatttagtg catgacgaat acacgaaata tatagacagt    5100
aaattaaacg aaattttcga tagtagcaat aaaaatgata tagagacaaa acgtgcgcgt    5160
acagattggt gggaaaacga agcaattgct gttcctaaca taacaggtgc aaataaaagt    5220
gatcctaaaa caattaggca gctagtatgg gatgctatgc aatctggagt aagaaaggcc    5280
atcgatgaag aaaaggaaaa aaaaaaaccg aatgaaaatt ttcctccatg tatgggagtt    5340
caacatatag aatagccaa acctcaattt ataagatggt tggaagaatg gacaaatgag    5400
ttttgcgaga aatatacaaa atatttcgaa gatatgaaat ccaattgtaa tctcagaaaa    5460
ggtgctgatg attgtgatga taatagtaat atcgaatgta aaaagcatg tgcaaattat    5520 acgaattggt taaatccaaa aaggatagaa tggaatggaa tgagcaatta ttataataaa    5580
atataccgta aaagtaacaa agaatcggaa gatggaaaag attattcaat gattatggaa    5640
cctacagtca ttgactattt gaacaaaaga tgcaatggcg aaattaatgg gaactacatt    5700
tgttgtagtt gtaaaaatat aggtgaaaat agcacttcag gtacagttaa taaaaaacta    5760
caaaaaaagg aaacacaatg tgaagacaat aaaggacctc tagatttaat gaacaaggta    5820
ttaaataaaa tggacccaaa atatagcgag cacaagatga agtgcacaga agtttacttg    5880
gaacatgttg aagaacaatt aaaagaaatt gacaatgcaa taaaagatta caaattatat    5940
cctttagata gatgttttga cgacaagagc aagatgaagg tgtgtgattt aattggagat    6000
gctataggat gtaaacataa gacaaaactg gatgaacttg atgaatggaa tgatgtggat    6060
atgcgagatc cttacaataa gtataaaggt gttttaattc ctcctagacg tagacaattg    6120
tgtttctcaa ggattgtgag aggtcccgca aatttaagaa acttaaagga atttaaagaa    6180
gaaattttaa aaggagccca atcggaaggt aagttttgg gtaattatta taacgaagat    6240
aaagataaag aaaaggcgct agaagctatg aaaaacagtt tttacgatta tgaatatata    6300
ataaaaggta gtgatatgtt aacaaatata caattcaagg atattaaaag gaaattagac    6360
agattactag aaaaagagac taataatacc gaaaagttg acgattggtg ggaaacaaat    6420
aagaaatcta tatggaatgc tatgttatgt gggtacaaga atctgggaa taaaataata    6480 gatccatcat ggtgtaccat acctactaca gaaacccctc cgcaatttttt acgatggata    6540 aaagaatggg gaacaaacgt gtgtatacaa aaagaagagc ataaagaata cgttaaatca    6600
aaatgttcta atgttactaa tttaggggca caagaatcgg aatcaaaaaa ttgtacatca    6660
gaaattaaaa aatatcaaga atggagcagg aaaaggtcta ttcagtggga agctatatcc    6720
gaaggttata aaaaatataa gggtatggat gaatttaaaa atacatttaa aaatataaag    6780
gaaccggatg ctaatgaacc gaatgctaat gaatatttga agaaacattg ttctaaatgt    6840
ccgtgtggat ttaatgatat gcaagaaata actaaatata caaacatcgg aaatgaagca    6900
tttaagcaaa taaagaaaca agttgatatt ccagctgaac ttgaagatgt tatttaccgt    6960 ctaaacatc atgagtatga taaaggtaat gattatattt gtaataaata taaaatata    7020 aacgttaata tgaaaaaaaa taatgatgat acttggactg atttggttaa aaattcttcg    7080
gacattaata aggtgtgct attacctcca cgaagaaaaa atttgtttct aaaaattgat    7140
gaatcagata tatgtaaata taaaagagat cctaaattgt ttaaagattt catttattcg    7200
```

```
tcggcaattt ctgaagttga aaggttaaaa aaagtatatg gtgaggctaa aacgaaagtt    7260
gttcatgcaa tgaaatatag ttttgccgat ataggaagta ttatcaaagg cgatgatatg    7320
atggaaaaca attcgtctga taagataggt aaaattttgg gagatggagt cggacaaaat    7380
gaaaaacgta aaaatggtg ggacatgaat aaatatcaca tatgggaatc tatgttatgt     7440
ggatacaaac atgcctacgg aaatatttca gaaaatgata gaaaaatgct tgatatacct    7500
aataatgatg acgaacatca atttcttcga tggtttcaag aatggactga aaatttctgt    7560
acaaaaagaa atgaattgta tgaaaatatg gtcactgcat gcaattctgc gaaatgcaat    7620
acatctaatg gatctgttga taaaaaagaa tgcactgaag catgtaaaaa ttatagtaat    7680
tttattttaa taaaaaaaaa ggagtatcag tcactaaata gtcaatacga tatgaattat    7740
aaagaaacca agcagaaaa aaaagaatcc ccagaatatt tcaaagataa atgtaatggt     7800
gaatgtagtt gtctctctga atattttaag gatgaaacaa gatggaaaaa tccttatgaa    7860
actctggatg acacagaagt taaaaataat tgtatgtgca aacctccccc cccagctagt    7920
aataatacca gtgacattct gcaaaaaacc attccttttg gtattgcgtt ggcgttagga    7980
tcaattgctt ttttattcat gaagaaaaaa cccaaaacac ctgtggacct tttacgtgta    8040
cttgatatac ctaaaggcga ttatggaata cccacccccca aatcatccaa tagatatatc    8100
ccctatgcaa gtgatcgata taaggcaaa acatatattt atatggaagg agatactagt     8160
ggagatgacg ataaatatat ttgggactta tcttcctctg atataacttc ctccgaaagt    8220
gagtatgaag aagtggatat caatgatata tatgtaccaa gttttcccaa atataaaacg    8280
ttcattgaat tagtactaga accttccaaa agggatacat ttaatacatc aagtggtgac    8340
acattcacca ataaacttac ggatgatgaa tggaaccaat tgaaacagga ttttattgaa    8400
caatatttac aaaacataca aaaggatttt attttacatg atagtatgga tgaaaaacct    8460
tttattactc aaatccagga tagatttctt gatagtagtc atgaagaagt tacttataat    8520
attgattgga atgttcctga aaatattaat aggattacta ataacatgga cgatccaaaa    8580
tactgctcaa ataatatgta tactggtacc gatttaatta atgattcatt aaatggtaac    8640
caatatattg atatatatga tgagatgctg aaacgaaaag aaaacgaatt atttggaaca    8700
tatcatacaa aatatacaac ctttaacagt gtttctaaac aaacacctag tgacccgata    8760
attaaccaac tagatttata tcataaatgg atagacaaac atagagatat ttgcgaacag    8820
tggaaaacca agaggatat gttatataaa ttgaatgaag tgtggaatat ggaacgtaag    8880
gaatatctat tggatataca accatcaact ctggatgata ttcataaaat taatgatgaa    8940
acatataata ttattagtac aaataatata tatgatcatc cctcacagga aacccccctc    9000
caactacttg gatcaacaaa tattataccc agttatatta ccacggaaca aaataatgga    9060
ttgcgcacaa atatatctat ggatacatat attgatgaaa caataataa taatgtggta    9120
gccactagta taataggtga cgatcagatg gaaaattcgt acaattgttg a             9171
```

<210> SEQ ID NO 2
<211> LENGTH: 3056
<212> TYPE: PRT
<213> ORGANISM: Plasmodium falciparum

<400> SEQUENCE: 2

Met Asp Lys Ser Ser Ile Ala Asn Lys Ile Glu Ala Tyr Leu Gly Ala
1               5                   10                  15

Lys Ser Asp Asp Ser Lys Ile Asp Gln Ser Leu Lys Ala Asp Pro Ser

-continued

```
                    20                  25                  30
Glu Val Gln Tyr Tyr Gly Ser Gly Gly Asp Gly Tyr Tyr Leu Arg Lys
            35                  40                  45

Asn Ile Cys Lys Ile Thr Val Asn His Ser Asp Ser Gly Thr Asn Asp
         50                  55                  60

Pro Cys Asp Arg Ile Pro Pro Tyr Gly Asp Asn Asp Gln Trp Lys
 65                  70                  75                  80

Cys Ala Ile Ile Leu Ser Lys Val Ser Glu Lys Pro Glu Asn Val Phe
                 85                  90                  95

Val Pro Pro Arg Arg Gln Arg Met Cys Ile Asn Asn Leu Glu Lys Leu
                100                 105                 110

Asn Val Asp Lys Ile Arg Asp Lys His Ala Phe Leu Ala Asp Val Leu
                115                 120                 125

Leu Thr Ala Arg Asn Glu Gly Glu Arg Ile Val Gln Asn His Pro Asp
            130                 135                 140

Thr Asn Ser Ser Asn Val Cys Asn Ala Leu Glu Arg Ser Phe Ala Asp
145                 150                 155                 160

Ile Ala Asp Ile Ile Arg Gly Thr Asp Leu Trp Lys Gly Thr Asn Ser
                165                 170                 175

Asn Leu Glu Gln Asn Leu Lys Gln Met Phe Ala Lys Ile Arg Glu Asn
            180                 185                 190

Asp Lys Val Leu Gln Asp Lys Tyr Pro Lys Asp Gln Asn Tyr Arg Lys
            195                 200                 205

Leu Arg Glu Asp Trp Trp Asn Ala Asn Arg Gln Lys Val Trp Glu Val
210                 215                 220

Ile Thr Cys Gly Ala Arg Ser Asn Asp Leu Leu Ile Lys Arg Gly Trp
225                 230                 235                 240

Arg Thr Ser Gly Lys Ser Asn Gly Asp Asn Lys Leu Glu Leu Cys Arg
                245                 250                 255

Lys Cys Gly His Tyr Glu Glu Lys Val Pro Thr Lys Leu Asp Tyr Val
                260                 265                 270

Pro Gln Phe Leu Arg Trp Leu Thr Glu Trp Ile Glu Asp Phe Tyr Arg
            275                 280                 285

Glu Lys Gln Asn Leu Ile Asp Asp Met Glu Arg His Arg Glu Glu Cys
290                 295                 300

Thr Ser Glu Asp His Lys Ser Lys Glu Gly Thr Ser Tyr Cys Ser Thr
305                 310                 315                 320

Cys Lys Asp Lys Cys Lys Lys Tyr Cys Glu Cys Val Lys Lys Trp Lys
                325                 330                 335

Ser Glu Trp Glu Asn Gln Lys Asn Lys Tyr Thr Glu Leu Tyr Gln Gln
            340                 345                 350

Asn Lys Asn Glu Thr Ser Gln Lys Asn Thr Ser Arg Tyr Asp Asp Tyr
            355                 360                 365

Val Lys Asp Phe Phe Lys Leu Glu Ala Asn Tyr Ser Ser Leu Glu
            370                 375                 380

Asn Tyr Ile Lys Gly Asp Pro Tyr Phe Ala Glu Tyr Ala Thr Lys Leu
385                 390                 395                 400

Ser Phe Ile Leu Asn Ser Ser Asp Ala Asn Asn Pro Ser Glu Lys Ile
                405                 410                 415

Gln Lys Asn Asn Asp Glu Val Cys Asn Cys Asn Glu Ser Gly Ile Ala
            420                 425                 430

Ser Val Glu Gln Glu Gln Ile Ser Asp Pro Ser Ser Asn Lys Thr Cys
435                 440                 445
```

```
Ile Thr His Ser Ser Ile Lys Ala Asn Lys Lys Val Cys Lys His
450                 455                 460

Val Lys Leu Gly Val Arg Glu Asn Asp Lys Asp Leu Arg Val Cys Val
465                 470                 475                 480

Ile Glu His Thr Ser Leu Ser Gly Val Glu Asn Cys Cys Cys Gln Asp
                485                 490                 495

Phe Leu Arg Ile Leu Gln Glu Asn Cys Ser Asp Asn Lys Ser Gly Ser
                500                 505                 510

Ser Ser Asn Gly Ser Cys Asn Asn Lys Asn Gln Glu Ala Cys Glu Lys
        515                 520                 525

Asn Leu Glu Lys Val Leu Ala Ser Leu Thr Asn Cys Tyr Lys Cys Asp
530                 535                 540

Lys Cys Lys Ser Glu Gln Ser Lys Lys Asn Asn Lys Asn Trp Ile Trp
545                 550                 555                 560

Lys Lys Ser Ser Gly Lys Glu Gly Gly Leu Gln Lys Glu Tyr Ala Asn
                565                 570                 575

Thr Ile Gly Leu Pro Pro Arg Thr Gln Ser Leu Cys Leu Val Val Cys
                580                 585                 590

Leu Asp Glu Lys Gly Lys Lys Thr Gln Glu Leu Lys Asn Ile Arg Thr
        595                 600                 605

Asn Ser Glu Leu Leu Lys Glu Trp Ile Ala Ala Phe His Glu Gly
610                 615                 620

Lys Asn Leu Lys Pro Ser His Glu Lys Lys Asn Asp Asp Asn Gly Lys
625                 630                 635                 640

Lys Leu Cys Lys Ala Leu Glu Tyr Ser Phe Ala Asp Tyr Gly Asp Leu
                645                 650                 655

Ile Lys Gly Thr Ser Ile Trp Asp Asn Glu Tyr Thr Lys Asp Leu Glu
                660                 665                 670

Leu Asn Leu Gln Lys Ile Phe Gly Lys Leu Phe Arg Lys Tyr Ile Lys
                675                 680                 685

Lys Asn Asn Thr Ala Glu Gln Asp Thr Ser Tyr Ser Ser Leu Asp Glu
690                 695                 700

Leu Arg Glu Ser Trp Trp Asn Thr Asn Lys Lys Tyr Ile Trp Leu Ala
705                 710                 715                 720

Met Lys His Gly Ala Gly Met Asn Ser Thr Thr Cys Cys Gly Asp Gly
                725                 730                 735

Ser Val Thr Gly Ser Gly Ser Ser Cys Asp Asp Ile Pro Thr Ile Asp
                740                 745                 750

Leu Ile Pro Gln Tyr Leu Arg Phe Leu Gln Glu Trp Val Glu His Phe
                755                 760                 765

Cys Lys Gln Arg Gln Glu Lys Val Lys Pro Val Ile Glu Asn Cys Lys
                770                 775                 780

Ser Cys Lys Glu Ser Gly Gly Thr Cys Asn Gly Glu Cys Lys Thr Glu
785                 790                 795                 800

Cys Lys Asn Lys Cys Glu Val Tyr Lys Lys Phe Ile Glu Asp Cys Lys
                805                 810                 815

Gly Gly Asp Gly Thr Ala Gly Ser Ser Trp Val Lys Arg Trp Asp Gln
                820                 825                 830

Ile Tyr Lys Arg Tyr Ser Lys Tyr Ile Glu Asp Ala Lys Arg Asn Arg
                835                 840                 845

Lys Ala Gly Thr Lys Asn Cys Gly Pro Ser Ser Thr Thr Asn Ala Ala
850                 855                 860
```

-continued

```
Glu Asn Lys Cys Val Gln Ser Asp Ile Asp Ser Phe Phe Lys His Leu
865                 870                 875                 880

Ile Asp Ile Gly Leu Thr Thr Pro Ser Ser Tyr Leu Ser Ile Val Leu
            885                 890                 895

Asp Asp Asn Ile Cys Gly Ala Asp Lys Ala Pro Trp Thr Thr Tyr Thr
                900                 905                 910

Thr Tyr Thr Thr Thr Glu Lys Cys Asn Lys Glu Thr Asp Lys Ser Lys
            915                 920                 925

Leu Gln Gln Cys Asn Thr Ala Val Val Val Asn Val Pro Ser Pro Leu
    930                 935                 940

Gly Asn Thr Pro His Gly Tyr Lys Tyr Ala Cys Gln Cys Lys Ile Pro
945                 950                 955                 960

Thr Asn Glu Glu Thr Cys Asp Asp Arg Lys Glu Tyr Met Asn Gln Trp
                965                 970                 975

Ser Cys Gly Ser Ala Arg Thr Met Lys Arg Gly Tyr Lys Asn Asp Asn
            980                 985                 990

Tyr Glu Leu Cys Lys Tyr Asn Gly Val Asp Val Lys Pro Thr Thr Val
            995                 1000                1005

Arg Ser Asn Ser Ser Lys Leu Asp Asp Lys Asp Val Thr Phe Phe Asn
    1010                1015                1020

Leu Phe Glu Gln Trp Asn Lys Glu Ile Gln Tyr Gln Ile Gly Gln Tyr
1025                1030                1035                1040

Met Thr Asn Thr Lys Ile Ser Cys Asn Asn Glu Lys Asn Val Leu Ser
                1045                1050                1055

Arg Val Ser Asp Glu Ala Ala Gln Pro Lys Phe Ser Asp Asn Glu Arg
            1060                1065                1070

Asp Arg Asn Ser Ile Thr His Glu Asp Lys Asn Cys Lys Glu Lys Cys
    1075                1080                1085

Lys Cys Tyr Ser Leu Trp Ile Glu Lys Ile Asn Asp Gln Trp Asp Lys
    1090                1095                1100

Gln Lys Asp Asn Tyr Asn Lys Phe Gln Arg Lys Gln Ile Tyr Asp Ala
1105                1110                1115                1120

Asn Lys Gly Ser Gln Asn Lys Lys Val Val Ser Leu Ser Asn Phe Leu
            1125                1130                1135

Phe Phe Ser Cys Trp Glu Glu Tyr Ile Gln Lys Tyr Phe Asn Gly Asp
            1140                1145                1150

Trp Ser Lys Ile Lys Asn Ile Gly Ser Asp Thr Phe Glu Phe Leu Ile
            1155                1160                1165

Lys Lys Cys Gly Asn Asp Ser Gly Asp Gly Glu Thr Ile Phe Ser Glu
    1170                1175                1180

Lys Leu Asn Asn Ala Glu Lys Lys Cys Lys Glu Asn Glu Ser Thr Asn
1185                1190                1195                1200

Asn Lys Met Lys Ser Ser Glu Thr Ser Cys Asp Cys Ser Glu Pro Ile
            1205                1210                1215

Tyr Ile Arg Gly Cys Gln Pro Lys Ile Tyr Asp Gly Lys Ile Phe Pro
            1220                1225                1230

Gly Lys Gly Gly Glu Lys Gln Trp Ile Cys Lys Asp Thr Ile Ile His
    1235                1240                1245

Gly Asp Thr Asn Gly Ala Cys Ile Pro Pro Arg Thr Gln Asn Leu Cys
    1250                1255                1260

Val Gly Glu Leu Trp Asp Lys Arg Tyr Gly Gly Arg Ser Asn Ile Lys
1265                1270                1275                1280

Asn Asp Thr Lys Glu Ser Leu Lys Gln Lys Ile Lys Asn Ala Ile Gln
```

-continued

```
                1285                1290                1295
Lys Glu Thr Glu Leu Leu Tyr Glu Tyr His Asp Lys Gly Thr Ala Ile
            1300                1305                1310
Ile Ser Arg Asn Pro Met Lys Gly Gln Lys Glu Lys Glu Glu Lys Asn
        1315                1320                1325
Asn Asp Ser Asn Gly Leu Pro Lys Gly Phe Cys His Ala Val Gln Arg
        1330                1335                1340
Ser Phe Ile Asp Tyr Lys Asn Met Ile Leu Gly Thr Ser Val Asn Ile
1345                1350                1355                1360
Tyr Glu Tyr Ile Gly Lys Leu Gln Glu Asp Ile Lys Lys Ile Ile Glu
            1365                1370                1375
Lys Gly Thr Thr Lys Gln Asn Gly Lys Thr Val Gly Ser Gly Ala Glu
            1380                1385                1390
Asn Val Asn Ala Trp Trp Lys Gly Ile Glu Gly Glu Met Trp Asp Ala
            1395                1400                1405
Val Arg Cys Ala Ile Thr Lys Ile Asn Lys Lys Gln Lys Lys Asn Gly
        1410                1415                1420
Thr Phe Ser Ile Asp Glu Cys Gly Ile Phe Pro Pro Thr Gly Asn Asp
1425                1430                1435                1440
Glu Asp Gln Ser Val Ser Trp Phe Lys Glu Trp Ser Glu Gln Phe Cys
            1445                1450                1455
Ile Glu Arg Leu Gln Tyr Glu Lys Asn Ile Arg Asp Ala Cys Thr Asn
            1460                1465                1470
Asn Gly Gln Gly Asp Lys Ile Gln Gly Asp Cys Lys Arg Lys Cys Glu
        1475                1480                1485
Glu Tyr Lys Lys Tyr Ile Ser Glu Lys Lys Gln Glu Trp Asp Lys Gln
        1490                1495                1500
Lys Thr Lys Tyr Glu Asn Lys Tyr Val Gly Lys Ser Ala Ser Asp Leu
1505                1510                1515                1520
Leu Lys Glu Asn Tyr Pro Glu Cys Ile Ser Ala Asn Phe Asp Phe Ile
            1525                1530                1535
Phe Asn Asp Asn Ile Glu Tyr Lys Thr Tyr Tyr Pro Tyr Gly Asp Tyr
            1540                1545                1550
Ser Ser Ile Cys Ser Cys Glu Gln Val Lys Tyr Tyr Glu Tyr Asn Asn
        1555                1560                1565
Ala Glu Lys Lys Asn Asn Lys Ser Leu Cys His Glu Lys Gly Asn Asp
        1570                1575                1580
Arg Thr Trp Ser Lys Lys Tyr Ile Lys Lys Leu Glu Asn Gly Arg Thr
1585                1590                1595                1600
Leu Glu Gly Val Tyr Val Pro Pro Arg Arg Gln Gln Leu Cys Leu Tyr
            1605                1610                1615
Glu Leu Phe Pro Ile Ile Ile Lys Asn Lys Asn Asp Ile Thr Asn Ala
            1620                1625                1630
Lys Lys Glu Leu Leu Glu Thr Leu Gln Ile Val Ala Glu Arg Glu Ala
        1635                1640                1645
Tyr Tyr Leu Trp Lys Gln Tyr His Ala His Asn Asp Thr Thr Tyr Leu
        1650                1655                1660
Ala His Lys Lys Ala Cys Cys Ala Ile Arg Gly Ser Phe Tyr Asp Leu
1665                1670                1675                1680
Glu Asp Ile Ile Lys Gly Asn Asp Leu Val His Asp Glu Tyr Thr Lys
            1685                1690                1695
Tyr Ile Asp Ser Lys Leu Asn Glu Ile Phe Asp Ser Ser Asn Lys Asn
            1700                1705                1710
```

-continued

```
Asp Ile Glu Thr Lys Arg Ala Arg Thr Asp Trp Trp Glu Asn Glu Ala
    1715                1720                1725

Ile Ala Val Pro Asn Ile Thr Gly Ala Asn Lys Ser Asp Pro Lys Thr
1730                1735                1740

Ile Arg Gln Leu Val Trp Asp Ala Met Gln Ser Gly Val Arg Lys Ala
1745                1750                1755                1760

Ile Asp Glu Glu Lys Glu Lys Lys Pro Asn Glu Asn Phe Pro Pro
            1765                1770                1775

Cys Met Gly Val Gln His Ile Gly Ile Ala Lys Pro Gln Phe Ile Arg
            1780                1785                1790

Trp Leu Glu Glu Trp Thr Asn Glu Phe Cys Glu Lys Tyr Thr Lys Tyr
        1795                1800                1805

Phe Glu Asp Met Lys Ser Asn Cys Asn Leu Arg Lys Gly Ala Asp Asp
        1810                1815                1820

Cys Asp Asp Asn Ser Asn Ile Glu Cys Lys Lys Ala Cys Ala Asn Tyr
1825                1830                1835                1840

Thr Asn Trp Leu Asn Pro Lys Arg Ile Glu Trp Asn Gly Met Ser Asn
            1845                1850                1855

Tyr Tyr Asn Lys Ile Tyr Arg Lys Ser Asn Lys Glu Ser Glu Asp Gly
            1860                1865                1870

Lys Asp Tyr Ser Met Ile Met Glu Pro Thr Val Ile Asp Tyr Leu Asn
        1875                1880                1885

Lys Arg Cys Asn Gly Glu Ile Asn Gly Asn Tyr Ile Cys Cys Ser Cys
        1890                1895                1900

Lys Asn Ile Gly Glu Asn Ser Thr Ser Gly Thr Val Asn Lys Lys Leu
1905                1910                1915                1920

Gln Lys Lys Glu Thr Gln Cys Glu Asp Asn Lys Gly Pro Leu Asp Leu
            1925                1930                1935

Met Asn Lys Val Leu Asn Lys Met Asp Pro Lys Tyr Ser Glu His Lys
            1940                1945                1950

Met Lys Cys Thr Glu Val Tyr Leu Glu His Val Glu Glu Gln Leu Lys
            1955                1960                1965

Glu Ile Asp Asn Ala Ile Lys Asp Tyr Lys Leu Tyr Pro Leu Asp Arg
    1970                1975                1980

Cys Phe Asp Asp Lys Ser Lys Met Lys Val Cys Asp Leu Ile Gly Asp
1985                1990                1995                2000

Ala Ile Gly Cys Lys His Lys Thr Lys Leu Asp Glu Leu Asp Glu Trp
            2005                2010                2015

Asn Asp Val Asp Met Arg Asp Pro Tyr Asn Lys Tyr Lys Gly Val Leu
            2020                2025                2030

Ile Pro Pro Arg Arg Arg Gln Leu Cys Phe Ser Arg Ile Val Arg Gly
    2035                2040                2045

Pro Ala Asn Leu Arg Asn Leu Lys Glu Phe Lys Glu Glu Ile Leu Lys
    2050                2055                2060

Gly Ala Gln Ser Glu Gly Lys Phe Leu Gly Asn Tyr Tyr Asn Glu Asp
2065                2070                2075                2080

Lys Asp Lys Glu Lys Ala Leu Glu Ala Met Lys Asn Ser Phe Tyr Asp
            2085                2090                2095

Tyr Glu Tyr Ile Ile Lys Gly Ser Asp Met Leu Thr Asn Ile Gln Phe
            2100                2105                2110

Lys Asp Ile Lys Arg Lys Leu Asp Arg Leu Leu Glu Lys Glu Thr Asn
    2115                2120                2125
```

```
Asn Thr Glu Lys Val Asp Asp Trp Trp Glu Thr Asn Lys Lys Ser Ile
        2130                2135                2140

Trp Asn Ala Met Leu Cys Gly Tyr Lys Lys Ser Gly Asn Lys Ile Ile
2145                2150                2155                2160

Asp Pro Ser Trp Cys Thr Ile Pro Thr Thr Glu Thr Pro Pro Gln Phe
            2165                2170                2175

Leu Arg Trp Ile Lys Glu Trp Gly Thr Asn Val Cys Ile Gln Lys Glu
        2180                2185                2190

Glu His Lys Glu Tyr Val Lys Ser Lys Cys Ser Asn Val Thr Asn Leu
        2195                2200                2205

Gly Ala Gln Glu Ser Glu Ser Lys Asn Cys Thr Ser Glu Ile Lys Lys
        2210                2215                2220

Tyr Gln Glu Trp Ser Arg Lys Arg Ser Ile Gln Trp Glu Ala Ile Ser
2225                2230                2235                2240

Glu Gly Tyr Lys Lys Tyr Lys Gly Met Asp Glu Phe Lys Asn Thr Phe
            2245                2250                2255

Lys Asn Ile Lys Glu Pro Asp Ala Asn Glu Pro Asn Ala Asn Glu Tyr
        2260                2265                2270

Leu Lys Lys His Cys Ser Lys Cys Pro Cys Gly Phe Asn Asp Met Gln
        2275                2280                2285

Glu Ile Thr Lys Tyr Thr Asn Ile Gly Asn Glu Ala Phe Lys Gln Ile
        2290                2295                2300

Lys Glu Gln Val Asp Ile Pro Ala Glu Leu Glu Asp Val Ile Tyr Arg
2305                2310                2315                2320

Leu Lys His His Glu Tyr Asp Lys Gly Asn Asp Tyr Ile Cys Asn Lys
            2325                2330                2335

Tyr Lys Asn Ile Asn Val Asn Met Lys Lys Asn Asn Asp Asp Thr Trp
        2340                2345                2350

Thr Asp Leu Val Lys Asn Ser Ser Asp Ile Asn Lys Gly Val Leu Leu
        2355                2360                2365

Pro Pro Arg Arg Lys Asn Leu Phe Leu Lys Ile Asp Glu Ser Asp Ile
        2370                2375                2380

Cys Lys Tyr Lys Arg Asp Pro Lys Leu Phe Lys Asp Phe Ile Tyr Ser
2385                2390                2395                2400

Ser Ala Ile Ser Glu Val Glu Arg Leu Lys Lys Val Tyr Gly Glu Ala
            2405                2410                2415

Lys Thr Lys Val Val His Ala Met Lys Tyr Ser Phe Ala Asp Ile Gly
        2420                2425                2430

Ser Ile Ile Lys Gly Asp Asp Met Met Glu Asn Asn Ser Ser Asp Lys
        2435                2440                2445

Ile Gly Lys Ile Leu Gly Asp Gly Val Gly Gln Asn Glu Lys Arg Lys
        2450                2455                2460

Lys Trp Trp Asp Met Asn Lys Tyr His Ile Trp Glu Ser Met Leu Cys
2465                2470                2475                2480

Gly Tyr Lys His Ala Tyr Gly Asn Ile Ser Glu Asn Asp Arg Lys Met
            2485                2490                2495

Leu Asp Ile Pro Asn Asn Asp Asp Glu His Gln Phe Leu Arg Trp Phe
        2500                2505                2510

Gln Glu Trp Thr Glu Asn Phe Cys Thr Lys Arg Asn Glu Leu Tyr Glu
        2515                2520                2525

Asn Met Val Thr Ala Cys Asn Ser Ala Lys Cys Asn Thr Ser Asn Gly
        2530                2535                2540

Ser Val Asp Lys Lys Glu Cys Thr Glu Ala Cys Lys Asn Tyr Ser Asn
```

-continued

```
            2545                2550                2555                2560
Phe Ile Leu Ile Lys Lys Lys Glu Tyr Gln Ser Leu Asn Ser Gln Tyr
            2565                2570                2575

Asp Met Asn Tyr Lys Glu Thr Lys Ala Glu Lys Lys Glu Ser Pro Glu
            2580                2585                2590

Tyr Phe Lys Asp Lys Cys Asn Gly Glu Cys Ser Cys Leu Ser Glu Tyr
            2595                2600                2605

Phe Lys Asp Glu Thr Arg Trp Lys Asn Pro Tyr Glu Thr Leu Asp Asp
        2610                2615                2620

Thr Glu Val Lys Asn Asn Cys Met Cys Lys Pro Pro Pro Ala Ser
2625                2630                2635                2640

Asn Asn Thr Ser Asp Ile Leu Gln Lys Thr Ile Pro Phe Gly Ile Ala
            2645                2650                2655

Leu Ala Leu Gly Ser Ile Ala Phe Leu Phe Met Lys Lys Lys Pro Lys
            2660                2665                2670

Thr Pro Val Asp Leu Leu Arg Val Leu Asp Ile Pro Lys Gly Asp Tyr
            2675                2680                2685

Gly Ile Pro Thr Pro Lys Ser Ser Asn Arg Tyr Ile Pro Tyr Ala Ser
            2690                2695                2700

Asp Arg Tyr Lys Gly Lys Thr Tyr Ile Tyr Met Glu Gly Asp Thr Ser
2705                2710                2715                2720

Gly Asp Asp Asp Lys Tyr Ile Trp Asp Leu Ser Ser Ser Asp Ile Thr
            2725                2730                2735

Ser Ser Glu Ser Glu Tyr Glu Glu Val Asp Ile Asn Asp Ile Tyr Val
            2740                2745                2750

Pro Ser Phe Pro Lys Tyr Lys Thr Phe Ile Glu Leu Val Leu Glu Pro
            2755                2760                2765

Ser Lys Arg Asp Thr Phe Asn Thr Ser Ser Gly Asp Thr Phe Thr Asn
            2770                2775                2780

Lys Leu Thr Asp Asp Glu Trp Asn Gln Leu Lys Gln Asp Phe Ile Glu
2785                2790                2795                2800

Gln Tyr Leu Gln Asn Ile Gln Lys Asp Phe Ile Leu His Asp Ser Met
            2805                2810                2815

Asp Glu Lys Pro Phe Ile Thr Gln Ile Gln Asp Arg Phe Leu Asp Ser
            2820                2825                2830

Ser His Glu Glu Val Thr Tyr Asn Ile Asp Trp Asn Val Pro Glu Asn
            2835                2840                2845

Ile Asn Arg Ile Thr Asn Asn Met Asp Asp Pro Lys Tyr Cys Ser Asn
            2850                2855                2860

Asn Met Tyr Thr Gly Thr Asp Leu Ile Asn Asp Ser Leu Asn Gly Asn
2865                2870                2875                2880

Gln Tyr Ile Asp Ile Tyr Asp Glu Met Leu Lys Arg Lys Glu Asn Glu
            2885                2890                2895

Leu Phe Gly Thr Tyr His Thr Lys Tyr Thr Thr Phe Asn Ser Val Ser
            2900                2905                2910

Lys Gln Thr Pro Ser Asp Pro Ile Ile Asn Gln Leu Asp Leu Tyr His
            2915                2920                2925

Lys Trp Ile Asp Lys His Arg Asp Ile Cys Glu Gln Trp Lys Thr Lys
            2930                2935                2940

Glu Asp Met Leu Tyr Lys Leu Asn Glu Val Trp Asn Met Glu Arg Lys
2945                2950                2955                2960

Glu Tyr Leu Leu Asp Ile Gln Pro Ser Thr Leu Asp Asp Ile His Lys
            2965                2970                2975
```

```
Ile Asn Asp Glu Thr Tyr Asn Ile Ile Ser Thr Asn Asn Ile Tyr Asp
        2980                2985                2990

His Pro Ser Gln Glu Thr Pro Leu Gln Leu Leu Gly Ser Thr Asn Ile
    2995                3000                3005

Ile Pro Ser Tyr Ile Thr Thr Glu Gln Asn Asn Gly Leu Arg Thr Asn
3010                3015                3020

Ile Ser Met Asp Thr Tyr Ile Asp Glu Thr Asn Asn Asn Asn Val Val
3025                3030                3035                3040

Ala Thr Ser Ile Ile Gly Asp Asp Gln Met Glu Asn Ser Tyr Asn Cys
        3045                3050                3055

<210> SEQ ID NO 3
<211> LENGTH: 8000
<212> TYPE: DNA
<213> ORGANISM: Plasmodium falciparum

<400> SEQUENCE: 3
atggacaagt cctccatcgc caacaagatc gaggcctacc tgggagccaa gtccgacgac      60
tccaagatcg accagagcct gaaggccgac ccctccgagg tgcagtacta cggctccgga     120
ggcgacggct actacctgag gaagaacatc tgcaagatca ccgtgaacca ctccgactcc     180
ggcaccaacg accttgcga cagaatcccc cctccttacg cgacaacga ccagtggaag      240 tgcgccatca tcctgtccaa ggtgtccgag aagcccgaga cgtgttcgt gccccccagg      300 agacagagga tgtgcatcaa caacctggag aagctgaacg tggacaagat cagggacaag      360
cacgccttcc tggccgacgt gctgctcacc gccaggaacg agggagagag gatcgtgcag      420
aaccaccccg acaccaactc ctccaacgtg tgcaacgccc tggagagatc cttcgccgac      480
atcgcagaca tcatcagggg aaccgacctg tggaagggca ccaactccaa cctggagcag      540
aacctgaagc agatgttcgc caagatcagg gagaacgaca aggtgctcca ggacaagtac      600
cccaaggacc agaactacag gaagctgagg gaggactggt ggaacgccaa caggcagaag      660
gtgtgggaag tgatcacctg cggagccagg tccaacgacc tgctcatcaa gaggggctgg      720
aggacctccg gcaagtccaa cggcgacaac aagctggagc tgtgcaggaa gtgcggacac      780
tacgaggaga aggtgcccac caagctggac tacgtgcccc agttcctgag atggctcacc      840
gagtggatcg aggacttcta cagggagaag cagaacctca tcgacgacat ggagaggcac      900
agggaggagt gcacctccga ggaccacaag tccaaggagg gcacctccta ctgctccacc      960
tgcaaggaca agtgcaagaa gtactgcgag tgcgtgaaga agtggaagtc cgagtgggaa     1020
aaccagaaga caagtacac cgagctgtac cagcagaaca agaacgagac ctcccagaag     1080
aacacctcca gatacgacga ctacgtgaag gacttcttca gaagctgga ggccaactac     1140 tccagcctgg agaactacat caagggcgac ccctacttcg ccgagtacgc caccaagctg     1200
tccttcatcc tgaactcctc cgacgccaac aacccctccg agaagatcca agaacaac      1260 gacgaggtgt gcaactgcaa cgagtccgga atcgcctccg tggagcagga gcagatctcc     1320
gacccctcca gcaacaagac ctgcatcacc cactcctcca tcaaggccaa caagaagaag     1380
gtgtgcaagc acgtgaagct gggcgtgagg gagaacgaca aggacctgag ggtgtgcgtg     1440
atcgaacaca cctcccctgtc cggagtggag aactgctgct gccaggactt cctgagaatc     1500
ctccaggaga actgctccga caacaagtcc ggctcctcct ccaacggctc ctgcaacaac     1560
aagaaccagg aggcctgcga agaacctg gagaaggtgc tggcctccct caccaactgc     1620
tacaagtgcg acaagtgcaa gtccgagcag tccaagaaga caacaagaa ctggatctgg     1680
```

```
aagaagagca gcggcaagga gggcggcctc cagaaggagt acgccaacac catcggactg   1740
ccccccagga cccagagcct gtgcctggtg gtgtgcctgg acgagaaggg caagaagacc   1800
caggagctga agaacatcag gaccaactcc gaactgctga aggagtggat catcgccgcc   1860
ttccacgagg gaaagaacct gaagccttcc cacgagaaga gaacgacga caacggcaag    1920 aagctgtgca aggccctgga gtacagcttc gccgactacg gcgacctcat caagggaacc   1980
tccatctggg acaacgagta cactaaggac ctggagctga acctgcagaa gatcttcgga   2040
aagctgttca ggaagtacat caagaagaac aacaccgccg agcaggacac ctcctactcc   2100
agcctggacg agctgaggga gtcctggtgg aacaccaaca gaagtacat ctggctggcc    2160 atgaagcacg gagccggcat gaactccacc acctgctgcg cgacggctc cgtgaccggc    2220 tccggctcct cctgcgacga catccctacc atcgacctca tccctcagta cctcagattc   2280
ctccaggagt gggtcgaaca cttctgcaag cagaggcagg agaaggtgaa gcccgtgatc   2340
gagaactgca agtcctgcaa ggagtccggc ggcacctgca acggcgagtg caagaccgag   2400
tgcaagaaca agtgcgaggt gtacaagaag ttcatcgagg actgcaaggg cggcgacggc   2460
accgccggat cctcctgggt gaagaggtgg gaccagatct acaagaggta ctccaagtac   2520
atcgaggacg ccaagaggaa caggaaggcc ggcaccaaga actgcggccc ttcctctacc   2580
accaacgccg ccgagaacaa gtgcgtgcag tccgacatcg acagcttctt caagcacctc   2640
atcgacatcg gcctcaccac cccctcctcc tacctgtcca tcgtgctgga cgacaacatc   2700
tgtggagccg acaaggcccc ctggaccacc tacaccactt acaccaccac cgagaagtgc   2760
aacaaggaga ccgacaagtc caagctccag cagtgcaaca ccgccgtggt ggtgaacgtg   2820 ccctccccc tgggcaacac ccccacggc tacaagtacg cctgccagtg caagatcccc     2880
accaacgagg aaacctgcga cgacaggaag gaatacatga accagtggtc ctgcggctcc   2940
gccagaacca tgaagagggg ctacaagaac gacaactacg agctgtgcaa gtacaacggc   3000
gtggacgtga agcccaccac cgtgagatcc aactcctcca agctggacga caaggacgtg   3060
accttcttca acctgttcga gcagtggaac aaggagatcc agtaccagat cgagcagtac   3120
atgaccaaca ccaagatctc ctgcaacaac gagaagaacg tgctgtccag ggtgtccgac   3180
gaggccgccc agcccaagtt ctccgacaac gagagggaca ggaactccat cacccacgag   3240
gacaagaact gcaaggagaa gtgcaagtgc tactccctgt ggatcgagaa gatcaacgac   3300
cagtgggaca gcagaagga caactacaac aagttccagc gcaagcagat ctacgacgcc    3360
aacaagggct cccagaacaa gaaggtggtg tccctgtcca acttcctgtt cttctcatgc   3420
tgggaggaat acatccagaa gtacttcaac ggcgactggt ccaagatcaa gaacatcggc   3480
tccgacacct tcgagttcct catcaagaag tgcggcaacg actccggcga cggagagacc   3540
atcttctccg agaagctgaa caacgccgag aagaagtgca aggagaacga gtccaccaac   3600
aacaagatga agtcctccga gacctcctgc gactgctccg agcccatcta catcagaggc   3660
tgccagccca agatctacga cggcaagatc ttccccggca agggcggcga gaagcagtgg   3720
atctgcaagg acaccatcat ccacggcgac accaacggcg cctgcatccc ccccaggact   3780
cagaacctgt gcgtgggaga gctgtgggac aagaggtacg gcggcaggtc caacatcaag   3840
aacgacacca aggagtccct gaagcagaag atcaagaacg ccatccagaa ggagaccgag   3900
ctgctgtacg agtaccacga caagggcacc gccatcatct ccaggaaccc catgaagggc   3960
cagaaggaga aggaggagaa gaacaacgac agcaacggcc tgcccaaggg cttctgccac   4020
```

```
gctgtgcaga ggagcttcat cgactacaag aacatgatcc tgggcacctc cgtgaacatc    4080
tacgagtaca tcggcaagct ccaggaggac atcaagaaga tcatcgagaa gggcaccacc    4140
aagcagaacg gcaagaccgt gggcagcgga gccgagaacg tgaacgcctg gtggaagggc    4200
atcgagggag agatgtggga cgccgtgagg tgcgccatca ccaagatcaa caagaagcag    4260
aagaagaacg gcaccttcag catcgacgag tgcggcatct ccccccccac cggcaacgac    4320
gaggaccagt ccgtgtcctg gttcaaggag tggtccgaac agttctgcat cgagaggctc    4380
cagtacgaga gaacatcag ggacgcctgc accaacaacg ccagggcga caagatccag    4440 ggcgactgca agagaaagtg cgaggagtac aagaagtaca tctccgaaaa gaagcaggag    4500
tgggacaagc agaagaccaa gtacgagaac aagtacgtgg gcaagtccgc ctccgacctg    4560
ctgaaggaga actaccccga gtgcatctcc gccaacttcg acttcatctt caacgacaac    4620
atcgagtaca agacctacta cccctacggc gactactcca gcatctgtag ctgcgagcag    4680
gtgaagtact acgaatacaa caacgctgag aagaagaaca acaagtccct gtgccacgag    4740
aagggcaacg acaggacctg gtccaagaag tacatcaaga agctggagaa cggcagaacc    4800
ctggagggcg tgtacgtgcc ccccaggagg cagcagctct gtctgtacga gctgttcccc    4860
atcatcatca agaacaagaa cgacatcacc aacgccaaga aggagctgct ggagaccctc    4920
cagatcgtgg ccgagagaga ggcctactac ctgtggaagc agtaccacgc ccacaacgac    4980
accacctacc tggctcacaa gaaggcctgc tgcgccatca gaggatcctt ctacgacctg    5040
gaggacatca tcaagggcaa cgacctggtg cacgacgagt acaccaagta catcgactcc    5100
aagctgaacg agatcttcga ctcctccaac aagaacgaca tcgagaccaa gagggccaga    5160
accgactggt gggagaacga ggccatcgcc gtgcccaaca tcaccggagc caacaagtcc    5220
gaccccaaga ccatcagaca gctcgtgtgg gacgctatgc agtccggagt gaggaaggcc    5280
atcgacgagg agaaggagaa gaagaagccc aacgagaact ccctcccctg catgggcgtg    5340
cagcacatcg gcatcgccaa gccccagttc atcagatggc tggaggaatg gaccaacgag    5400
ttctgcgaga gtacaccaa gtacttcgag gacatgaagt ccaactgcaa cctgaggaag    5460
ggagccgacg actgcgacga caactccaac atcgagtgca agaaggcctg cgcaaactac    5520
accaactggc tgaacccccaa gaggatcgag tggaacggca tgagcaacta ctacaacaag    5580
atctacagga agagcaacaa ggagtccgag gacggcaagg actacagcat gatcatggag    5640
cccaccgtga tcgactacct gaacaagagg tgcaacggcg agatcaacgg caactacatc    5700
tgctgctctt gcaagaacat cggcgagaac tccacctccg gcaccgtgaa caagaagctc    5760
cagaagaagg agacccagtg cgaggacaac aagggcccctc tggacctcat gaacaaggtg    5820
ctgaacaaga tggaccccaa gtactccgag cacaagatga agtgcaccga ggtgtacctg    5880
gagcacgtgg aggaacagct gaaggagatc gacaacgcca tcaaggacta caagctgtac    5940
cccctggaca gatgcttcga cgacaagtcc aagatgaagg tgtgcgacct catcggcgac    6000
gccatcggat gcaagcacaa gaccaagctg gacgaactgg acgagtggaa cgacgtggac    6060
atgagggacc cttacaacaa gtacaagggc gtgctcatcc cccccaggag gaggcagctc    6120
tgcttcagca gaatcgtgag aggacccgcc aacctgagaa acctgaagga gttcaaggag    6180
gagatcctga agggagccca gtccgaggc aagttcctgg caactactac aacgaggac    6240 aaggacaagg agaaggccct ggaggccatg aagaactctt tctacgacta cgagtacatc    6300
atcaagggct ccgacatgct caccaacatc cagttcaagg acatcaagcg caagctggac    6360
aggctgctgg agaaggagac caacaacacc gagaaggtgg acgactggtg ggagaccaac    6420
```

```
-continued aagaagtcca tctggaacgc catgctgtgc ggctacaaga agtccggcaa caagatcatc      6480
gacccttcct ggtgcaccat ccctaccacc gagaccccc  cacagttcct gagatggatc      6540
aaggagtggg gaaccaacgt gtgcatccag aaggaggagc acaaggagta cgtgaagtcc      6600
aagtgctcca acgtgaccaa cctgggagcc caggagtccg agtccaagaa ctgcaccagc      6660
gagatcaaga agtaccagga gtggtccagg aagagatcca tccagtggga ggccatctcc      6720
gagggctaca agaagtacaa gggcatggac gagttcaaga acactttcaa gaacatcaag      6780
gagcccgacg ccaacgagcc caacgccaac gagtacctga agaagcactg ctccaagtgc      6840
ccctgcggct tcaacgacat gcaggaaatc accaagtaca ccaacatcgg caacgaggcc      6900
ttcaagcaga tcaaggagca ggtggacatc cccgccgagc tggaggacgt gatctacagg      6960
ctgaagcacc acgagtacga caagggcaac gactacatct gcaacaagta caagaacatc      7020
aacgtgaaca tgaagaagaa caacgacgac acctggaccg acctggtgaa gaactcctcc      7080
gacatcaaca agggcgtgct gctgcccct  aggaggaaga acctgttcct gaagatcgac      7140
gagtccgaca tctgcaagta caagagggac cccaagctct tcaaggactt catctactcc      7200
tccgccatca gcgaagtgga gcgactgaag aaggtgtacg gcgaggccaa gaccaaggtg      7260
gtgcacgcca tgaagtactc tttcgccgac atcggctcca tcatcaaggg cgacgacatg      7320
atggagaaca acagctccga caagatcggc aagatcctgg gcgacggcgt gggccagaac      7380
gagaagagga agaagtggtg ggacatgaac aagtaccaca tctgggagtc catgctgtgc      7440
ggatacaagc acgcctacgg caacatctcc gagaacgaca ggaagatgct cgacatcccc      7500
aacaacgacg acgagcacca gttcctgaga tggttccagg agtggaccga gaacttctgc      7560
accaagagga acgagctgta cgaaaacatg gtgaccgcct gcaactccgc caagtgcaac      7620
acctccaacg gcagcgtgga caagaaggag tgcaccgagg cttgcaagaa ctactccaac      7680
ttcatcctca tcaagaagaa ggagtaccag agcctgaact cccagtacga catgaactac      7740
aaggagacca aggccgagaa gaaggagtcc cccgagtact tcaaggacaa gtgcaacggc      7800
gagtgctcct gcctgtccga gtacttcaag gacgaaacca ggtggaagaa ccctacgag       7860 accctggacg acaccgaggt gaagaacaac tgcatgtgca agccccctcc ccctgcctcc      7920
aacaacacca gcgacatcct ccagaagacc atcccttcg  gaatcgccct ggctctggga      7980
tccatcgctt tcctgttcat                                                 8000
```

COMPOUNDS USEFUL IN THE DIAGNOSIS AND TREATMENT OF PREGNANCY-ASSOCIATED MALARIA

FIELD OF THE INVENTION

The present invention relates to the fields of preventing or treating pregnancy-associated malaria (PAM) and it provides compounds, which are useful within these fields. These compounds may be used as medicaments or they may constitute parts of pharmaceutical compositions, in particular immunogenic compositions. Also, these compounds may be used in vaccines and in methods of treatment and for the manufacture of compositions and/or they may provide basis for a method of generating a vaccine against PAM. Furthermore, the invention relates to the use of these compounds as biotechnological tools and in in vitro diagnostic methods and kits.

GENERAL BACKGROUND

Malaria constitutes a permanent catastrophe. Annually, the disease kills between 1 and 2 million Africans and the economic losses due to malaria constitute a hindrance for economic development. In areas of stable malaria transmission the disease mainly affects children, because adults have acquired immunity which protects them against severe malaria syndromes and most febrile malaria episodes. However, pregnant women constitute an important exception to this rule since they often suffer from severe malaria attacks.

Further, even in the absence of overt clinical symptoms the presence of parasites in pregnant women can have very serious consequences for both mother and child because the infection cause maternal anaemia, as well as premature delivery, low birth weight, and increased infant mortality (Brabin, 1983).

Thus, pregnancy-associated malaria (PAM) is a major health problem in malaria-endemic areas and on a world basis it affects millions of pregnant women and their offspring. In endemic areas, PAM is concentrated among primigravid women, indicating that protective immunity to PAM is acquired as a function of parity and that it is possible to make a vaccine protecting against PAM.

Malaria is caused by unicellular parasites living and multiplying asexually in the red blood cells (RBC). In each 48-hour cycle, the parasites invade RBC, multiply within them, and eventually burst them, before they go on to invade new RBC. Four Plasmodium species cause human disease, but by far the most of the malaria disease burden is caused by *Plasmodium falciparum*, which is also the cause of PAM.

RBC infected by the late developmental stages of *P. falciparum* blood parasites are not found in the peripheral circulation, as they adhere to receptors on the endothelial lining. This adhesion, called sequestration, is mediated through parasite-encoded, clonally variant surface antigens (VSA) inserted into the membrane of the infected RBC (IRBC) and is thought to be an immune evasion strategy, possibly evolved to avoid splenic clearance.

The best-characterised VSA are encoded by the var genes. This gene family, encompassing about 60 members per genome, encodes the variant protein *P. falciparum* erythrocyte membrane protein 1 (PfEMP1), which is located on the surface of the *P. falciparum*-infected erythrocytes where it mediates adhesion.

A given parasite expresses only one PfEMP1 at a time, but in each generation a fraction of the daughter parasites may switch to expression of alternative PfEMP1 species through an unknown process. Different PfEMP1 molecules have different receptor specificities, and clonal switching between expression of the various var gene products in a mutually exclusive manner allows the parasite to modify its adhesion properties, which in turn determines in which tissue the parasite can sequester (Wahlgren et al., 1999).

PAM is caused by the accumulation of parasites in the intervillous space of the placenta, where parasites adhere to the syncytlotrophoblast.

The glycosaminoglycan chondroltin sulphate A (CSA) can mediate parasite adhesion in vitro, and although CSA-adhering parasites are rarely found in non-pregnant hosts, placental parasites preferentially or perhaps even exclusively bind to CSA, whereas they seldom bind to CD36, which is the most common sequestration ligand for parasites from non-pregnant hosts. Thus, it seems that the placenta constitutes a niche for antigenically distinct parasite variants that have evolved to sequester exclusively at this site.

According to this theory, such parasites cannot survive in non-pregnant hosts. Primigravid women in endemic countries are consequently fully susceptible to CSA-adhering parasites, even if they have acquired protection to most other parasite variants. With increasing parity, an increasing proportion of women has encountered such parasites during previous pregnancies and produced protective antibodies against them, which in turn explains the parity-dependency of susceptibility to PAM. This notion is supported by the fact that plasma from some pregnant women can block the binding of placental parasites to CSA and that the proportion of pregnant women with plasma that block binding at partum increases with parity (Duffy and Fried, 1999).

As PAM can occur even in women who have acquired immunity to malaria, the parasites causing PAM must be able to escape the immunological effector mechanisms that control parasite multiplication in immune hosts. This is supported by the fact that VSA expressed by parasites isolated from the placenta of women with PAM are not recognised by plasma antibodies from clinically immune adult males or women who have not been pregnant, implying that the VSA expressed by parasites causing PAM cannot multiply successfully in men, but only in women harbouring a placenta.

Another significant characteristic shared by VSA expressed by placental parasite isolates is that the levels of plasma IgG in malaria-exposed pregnant women are positively correlated to parity (parity-dependent IgG recognition). Together, these observations suggest that parasites causing PAM express VSA molecules that do not cross-react serologically with the VSA expressed on parasites which do not sequester in the placenta, and that a vaccine protecting against PAM, should induce antibodies which recognise VSA on placental parasites but not VSA expressed by parasites isolated from peripheral blood of men or non-pregnant women.

The ability of plasma to block the binding of placental parasites to CSA which are found in some malaria-exposed pregnant women, is independent of the geographic origin of plasma as well as parasites (Fried et al., 1998). These data suggest that the VSA responsible for placental adhesion to CSA are not only functionally and antigenically distinct from other molecules present at the IRBC surface, but also that they share relatively conserved antigenic determinants. The fact that many women in areas of low malaria transmission intensity suffer from PAM indicates that even though parasites in the peripheral blood of non-pregnant individuals do not express the protein responsible for placental adhesion, most parasite genomes carry genes encoding the protein, which can be selected for or actively turned on if the parasite infects a pregnant women. Together these data indicate that the gene encoding the protein responsible for PAM is carried by most parasites, and that it is conserved and structurally different from other VSA.

Parasites isolated from peripheral blood of non-pregnant individuals do not normally bind to CSA in vitro but after several rounds of in vitro panning on CSA bound to plastic, parasite lines that bind specifically to CSA can be established. These parasite lines normally express VSA with several phenotypical features similar to VSA expressed by placental parasites: i) CSA-selected parasites bind to placental tissue, ii) CSA-selected parasites are recognised by plasma in a gender- and parity-dependent manner (Staalsoe et al., 2001), iii) plasma from pregnant women often block the adhesion of CSA-selected parasites to both CSA and placental tissue, iv) CSA selected parasites do not bind CD36. None of these characteristics are normally found in the parental parasite lines before CSA selection. Thus, in vitro-generated, CSA-binding parasite lines resemble placental parasites, and comparison of gene expression between CSA-binding parasite lines and the parental line can be( used as a tool to identify the gene(s) involved in the pathogenesis of PAM.

Several groups of researchers have identified specific PfEMP1 molecules that can mediate binding to CSA (Buffet et al., 1999). One such molecule, FCR3.varCSA, has been cloned recently and its prophylactic and therapeutic applicability with respect to PAM has been claimed (Scherf et al. WO 01/16326). However, this parasite isolate was not shown to be gender-specifically recognised by immune sera. One must keep in mind, however, that the structure of PfEMP1 has been optimised during evolution to mediate binding to different ligands.

Since CSA bearing proteins also exist on the endothelial surface outside the placenta, and CSA is notoriously a sticky molecule, the demonstration that a species of PfEMP1 mediates binding to CSA does not in itself constitute evidence that the molecule mediates binding to placenta in vivo and is involved in the pathogenesis of PAM. As for the FCR3.varCSA, it has subsequently been reported that a FCR3CSA strain with a FCR3varCSA knockout is still able to adhere in vitro to CSA.

The present invention relates to a particular PfEMP1, VAR2CSA and the var2csa gene, which serves a unique function for *Plasmodium falciparum*.

WO 00 25728 describes the DNA and protein sequences derived from the sequencing of chromosome 2 of *Plasmodium falciparum* 3D7. The sequences are disclosed for use in a vaccine against malaria. This publication does not address any expression characteristics, binding abilities or antigenic properties for any of the disclosed sequences, nor does this application does not relate to pregnancy associated malaria. Furthermore, the chromosome 2 of *P. falciparum* contains numerous fragmented and truncated var sequences.

Sequence ID No 3 is the protein sequence of the DNA in sequence in SEQ ID No 213. This sequence only disclose a fragment of 1323 bp/440 aa coding for a truncated PfEMP1 encoding only the conserved exon2 part of the molecule.

In the EMBL online database, Database accession no. AE014844, disclose *Plasmodium falciparum* 3D7 chromosome 12 section 1 of 9 of the complete sequence.

This sequence is identical to var2csa and is derived from the sequencing of the whole *Plasmodium falciparum* 3D7 genome. The online reference is merely a sequence submisson and does not contain any information on function of sequence nor any relevance for a malaria vaccine or a pregnancy associated malaria vaccine.

In the present application, the var2csa sequence is provided as SEQ ID NO.: 1 and is excluded from the embodiments pertaining to the nucleic acid sequences as such. An open reading frame (ORF) comprises nucleic acids No. 48802-56805. This ORF is the translation of the nucleotide sequence of var2csa derived from the sequencing of the whole *Plasmodium falciparum* 3D7 genome. In the present application, this protein sequence is provided as SEQ ID NO.: 2 and is excluded from the embodiments relating to amino acid sequences as such.

In the EMBL online database, Database accession no. BQ739499 (PfESToab46 g01.y1) describes a cDNA fragment of 548 bp identical to var2csa. This fragment is derived from sequencing of a *Plasmodium falciparum* 3D7 EST library. This online submisson does not contain any information on this sequence in relation to a vaccine against malaria.

WO 01/16326 disclose a PfEMP1 sequence for the use in a vaccine against PAM and for the use of treatment of PAM. The sequence FCR3varCSA is from the *Plasmodium falciparum* strain FCR3 and is fundamentally different from var2csa in spite of the proteins belonging to the same variant surface antigen family (var).

As mentioned above, PfEMP1 genes show both intra and inter genomic variation, and the global repertoire of PfEMP1 proteins is assumed to be very large. The common features shared by the PfEMP1 family of genes and proteins (Smith et al., 1995) are the organisation of the genes (two exons and an intron), and the presence of domain structures that can be classified as Duffy Binding ligand-like (DBL) or cysteine-rich interdomain region (CIDR)(Smith et al., 2000).

In addition the proteins share a relative conserved c-terminal tail consisting of a trans membrane region and a relatively short intracellular domain. However, it must be stressed that the genes and the encoded proteins vary considerably between each other; both with regards to sequence (primary structure) and organisation of the domains (Lavstsen et al., 2003).

It is also clear that expression of different PfEMP1 molecules confer parasite different functional (Smith et al., 1995). (Smith et al., 2000; Robinson et al., 2003) and antigenic characteristics (Salanti et al., 2003). Furthermore, it is obvious that an efficient PfEMP1-based vaccine against malaria and PAM in particular is limited to a few specific PfEMP1 types.

Within PfEMP1 domains classified as belonging to the same group and subgroup (i.e. DBLα, DBLβ, CIDRγetc) short identity blocks of 2-14 amino acids can be identified between hyper variable blocks of varying lengths (of up to several hundred amino acids) in which there is no or very little homology between randomly chosen PfEMP1s.

Although the sequence of the entire *P. falciparum* genome is known, the VAR2CSA protein and its role in the pathogenesis of malaria has not previously been described. Accordingly, the present invention provides a new PfEMP1 molecule. The PfEMP1 molecules constitute a very large and diverse family of proteins, the prior identification of other PfEMP1 molecule does not suggest any function of VAR2CSA for the parasite, which is unique, and distinct from that of previously described PfEMP1s.

The domain structure of FCR3varCSA is somehow classic consisting of a "conserved" domain headstructure (DBL1α, CIDR1α, DBL2β), furthermore the CSA binding domain of this molecule has been mapped to the DBL3-γ of this molecule and until the discovery of VAR2CSA there was a general consensus about DBL3-γ as being the CSA binding domain.

The domain structure of VAR2CSA is fundamentally different from all other PFEMP1 proteins, including FCR3varCSA.

The first 3 domains do not fit any current classification and has been named DBLX—the last 3 domains are a unusual repetition of three ε domains: DBL1-X, DBL2-X, DBL3-X, DBL4ε, DBL5ε, DBL6ε.

What is most noteworthy is that VAR2CSA does not have the DBL-γ domain which was thought to be the domain mediating adhesion to CSA and to placenta nor is there any CIDR domains present.

A ClustalX alignment of the exon1 of the two proteins only gives an overall identity of 18.3% and it is not even possible to make a reasonable aligment from the nucleotide sequence. Thus the two proteins are very different in both primary sequence structure and in domain architectural structure.

Summa summarum, *Plasmodium falciparum* erythrocyte membrane protein-1 (PfEMP1), is a highly polymorphic and diverse family of proteins. Every parasite genome carries as mentioned about 60 genes encoding PfEMP1 and the repertoire of PfEMP1 genes differ from parasite genome to parasite genome. Thus, PfEMP1 genes show both intra and inter genomic variation, and the global repertoire of PfEMP1 proteins is assumed to be very large.

SUMMARY OF THE INVENTION

In essence, the inventive concept described herein is based on the observation that a single gene, var2csa, is up-regulated, both transcriptionally and translationally, in parasites of the species *Plasmodium falciparum*, when these parasites have been selected for their ability to mediate adhesion of infected RBC to CSA in vitro and that this gene product is gender specifically and parity dependently recognised by immune serum As the cytoadhesion to CSA is intimately linked to pregnancy-associated malaria products of this gene provide for novel approaches to diagnosing and treating PAM prophylactically and/or therapeutically.

In the broadest sense, the present invention relates to a polypeptide, VAR2CSA, encoded by the var2csa gene, and provides parts hereof as well as polypeptides, which with respect to their sequence are identical in part to the VAR2CSA or said parts hereof. In addition, the invention relates to the var2csa nucleic acid molecule and provides parts hereof as well as nucleic acid molecules, which with respect to their sequence are identical in part to the var2csa nucleic acid molecule or to said parts hereof.

In preferred embodiments, polypeptides of the invention comprise sub-sequences of the above mentioned polypeptides of at least 100 amino acids in length and having at least 80% sequence identity to VAR2CSA. In Equally preferred embodiments nucleic acids molecules of the invention comprise sub-sequences of the above mentioned nucleic acid molecules, which are at least 300 nucleotides in length and have at least 80% sequence identity. Even more preferred embodiments are polypeptides of the invention bearing one or more B-cell epitope(s) and, optionally, other epitopes, in particular T-cell epitopes found within the full-length sequence of the polypeptide or nucleotide sequences encoding such sub-sequences. Other preferred embodiments may be regions within the polypeptides of the invention and corresponding regions within the nucleic acid molecules of the invention, which can be shown to be involved in interaction with CSA or regions which may be assumed to be involved in such interaction.

A primary aspect of the present invention pertains to the above mentioned amino acid sequences and nucleic acid sequences for use as a medicament. Other aspects of the invention include pharmaceutical compositions, in particular immunogenic compositions, and use of the polypeptides and nucleic acids for the manufacture of compositions, hereunder immunogenic compositions which are to administered in order to prophylactically or therapeutically reduce the incidence, prevalence or severity of PAM. It is further within the scope of the present invention to provide a method of treatment and prevention of pregnancy-associated malaria which comprises administering an effective amount of one or more of the described molecules of the invention to a subject. It will appear that the mentioned polypeptides and nucleic acid molecules will also be useful as biotechnological tools. Therefore, the invention also relates to in vitro diagnostic methods, which comprise contacting a sample with polypeptides or nucleic acid molecules having the sequences described above, allowing in vitro reactions to occur and subsequently detecting any molecular complexes formed. These may for instance be complexes of antigens and antibodies. In some aspects of the invention, the polypeptides of the invention are parts of diagnostic kits. Alternatively, these kits may comprise antibodies, which specifically recognise such polypeptides.

Other aspects include vaccines based on the molecules of the invention, and, finally, it is also within the scope of the present invention to provide compounds comprising at least one of these molecules with the proviso that the full-length sequence of the VAR2CSA polypeptide and the full-length var2csa nucleotide sequence are excluded.

Finally, some aspects of the invention relate to the process of identifying compounds or compositions, which can be employed in the therapeutic or prophylactic treatment of malaria. This may for instance be a method for identifying agents capable of modifying the VAR2CSA dependent adhesion to glycos-amino glucans (GAG), wherein a cell expressing one of the above mentioned polypeptides is provided. When contacted with the agent(s) of interest, the adhesion of this cell to GAG is detected. Alternatively, interaction of the agent(s) with the expressed polypeptides is detected. Finally, in one aspect, the invention relates to a method for identifying polypeptides, which will induce a specific IgG/antibody response, or nucleic acid molecules encoding such polypeptides. This method comprises contacting a tissue or a fluid sample with such polypeptides and detecting in vitro reactions with IgGs/antibodies possibly present in the sample.

DEFINITIONS RELATING TO THE PRESENT INVENTION

The term 'adhesion to CSA' refers to the ability of erythrocytes infected by mature stages of *P. falciparum* to adhere (bind) to surfaces (artificial supports such as a polymer, or tissues), where chondroitin sulphate A (CSA) is available for specific interaction with variant surface antigens expressed on the surface of the infected erythrocytes. The capacity of a given parasite isolate/line/clone for adhesion to CSA in vitro is defined as the proportion of parasitised erythrocytes that can withstand washing after having been allowed to adhere (bind) to CSA. The term 'adhesion to CSA' is further described and defined in Fried & Duffy, 1996.

In the present context 'complementary sequence' refers to nucleotide sequences which will hybridise to a nucleic acid molecule of the invention under stringent conditions. The term "stringent conditions" in refers to general conditions of high stringency. The term "stringency" is well known in the art and is used in reference to the conditions (temperature, ionic strength and the presence of other compounds such as organic solvents) under which nucleic acid hybridisations are conducted. With "high stringency" conditions, nucleic acid base pairing will occur only between nucleic acid fragments that have a high frequency of complementary base sequences, as compared to conditions of "weak" or "low" stringency.

As an example, high stringency hybridisation conditions comprise (1) low ionic strength and high temperature for washing, such as 0.015 M NaCl/0.0015 M sodium citrate, pH 7.0 (0.1×SSC) with 0.1% sodium dodecyl sulfate (SDS) at 50° C.; (2) hybridisation in 50% (vol/vol) formamide with 5×Denhardt's solution (0.1% (wt/vol)) highly purified bovine serum albumin/0.1% (wt/vol) Ficoll/0.1% (wt/vol) polyvinylpyrrolidone), 50 mM sodium phosphate buffer at pH 6.5 and 5×SSC at 42° C.; or (3) hybridisation in 50% formamide, 5×SSC, 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C. with washes at 42° C. in 0.2×SSC and 0.1% SDS.

The term 'effective amount' refers to an amount or concentration of a substance such as an amino acid sequence, nucleotide sequence or an antibody which is effective to produce a protective prophylactic or therapeutic response with respect to the disease malaria. In general, an effective amount of the substance, which is administered to a human subject, will vary depending upon a number of factors associated with that subject, including whether the subject has previously been exposed to *Plasmodium falciparum*. The person of ordinary skill in the art can determine an effective amount of the substance by varying the dosage of the product and measuring the resulting cellular and humoral immune and/or therapeutic responses subsequent to administration. In particular, the concentration range of an immunogenic substance is chosen so as to enhance the likelihood of eliciting an immunogenic response e.g. vaccinating the recipient for a long period of time, without causing a malaria infection in the vaccine recipient.

'Endemic areas' refers to areas where transmission of *P. falciparum* parasites occurs repeatedly over years. Depending on the intensity of transmission, endemic areas are often divided (in order of decreasing intensity) into holo-(Intense, perennial transmission), hyper- (intense, seasonal transmission), meso- (less intense, locally and temporally varying transmission), hypo-endemic (little transmission with little effect at the population level) areas.

A 'B-cell epitope' is defined as an antigenic determinant, which functionally is the portion of an antigen, which combines with the antibody paratope. B-cell epitopes are usually composed of approximately 6 amino acids and are expected to be located at the surface of the protein and surface probability programs and hydrofobicity plots can therefore help defining areas with B-cell epitopes. With respect to the present invention the Protean 4.0 software in the DNAstar package is used with default settings when defining such areas. Specific B-cell epitopes should preferably be determined experimentally, which can be done by methods well known to the person of ordinary skill in the art.

In the present context the term 'DNA vaccine' refers to vaccines based on any species of nucleic acid molecules, comprising species of DNA or RNA.

The term 'T cell epitope' refers to a sequence of about ten amino acids that are part of a much longer, folded chain of amino acids and can lead to activation of a T-cell when presented on the surface of a cell in complex with Major Histocompatibility Complex (MHC) II and/or 1. Probability values for putative T-cell epitopes within a polypeptide may be obtained with the use of computers, neural networks and prediction servers such as SYFPEITHI server at Centre for Biological Sequence Analysis BioCentrum-DTU, Technical University of Denmark (syfpeithi.bmi-heidelberg.com/Scripts/MHCServer.dll/EpPredict.htm) which is used with default unchangeable settings.

The term 'fusion protein' is to be interpreted as the product of a var2csa nucleic acid sequence to which an exogenous nucleic acid sequence that may be of virtually any length has been added.

'in vitro panning' refers to a procedure by which erythrocytes infected by a particular isolate/line/clone of *P. falciparum* is selected for dominant expression of a variant surface antigen (VSA) with defined adhesion characteristics. To select for expression of VSA that can adhere to chondroitin sulphate A (CSA) in vitro by in vitro panning, erythrocytes infected by mature stages of the isolate/line/clone in question are allowed to adhere to culture dishes previously coated by CSA. Unbound (non-adhering) erythrocytes are removed by washing, and only the remaining bound (adhering) are used to propagate the isolate/line/clone further. The process of in vitro panning is usually repeated at a minimum of three times to ensure uniform expression of the VSA with the desired adhesion characteristics.

The term 'nucleic acid molecule' refers to an oligomer or polymer of ribonucleic acid (RNA) or deoxyribonucleic acid (DNA) or mimetics thereof. This term includes molecules composed of naturally-occurring nucleobases, sugars and covalent internucleoside (backbone) linkages as well as molecules having non-naturally occurring nucleobases, sugars and covalent internucleoside (backbone) linkages which function similarly or combinations thereof. Such modified or substituted nucleic acids are often preferred over native forms because of desirable properties such as, for example, enhanced cellular uptake, enhanced affinity for nucleic acid target and increased stability in the presence of nucleases and other enzymes, and are in the present context described by the terms "nucleic acid analogues" or "nucleic acid mimics". Preferred examples of nucleic acid mimetics are peptide nucleic acid (PNA-), Locked Nucleic Acid (LNA-) , xylo-LNA-, phosphorothioate-, 2'-methoxy-, 2'-methoxyethoxy-, morpholino- and phosphoramidate-containing molecules or the like.

By 'Parity-dependent antibody recognition' is meant specific plasma IgG antigen recognition that is monotonously increasing at the population level with increasing parity (gravidity) of the plasma donors and is independent of plasma donor age. To test for parity-dependent antibody recognition of variant surface antigens (VSA) expressed on the surface of erythrocytes infected by a *P. falciparum* isolate, line, or clone, the level of specific recognition of VSA expressed by the isolate/line/clone in question in a panel of Individual plasma samples from third-trimester pregnant women of different parity is determined by flow cytometry (Staalsoe et al. 1999). The isolate/line/clone is said to show parity-dependent antibody recognition if there is a statistically significant (Multiple linear regression analysis, P<0.05) effect of donor parity on the level of VSA-specific IgG recognition in individual plasma samples after allowing for the confounding effect of age.

With respect to the present invention the term 'polypeptide' refers to an amino acid chain of any length, including a full-length protein, oligopeptides, short peptides and fragments thereof, wherein the amino acid residues are linked by covalent bonds.

'isolated' and 'purified': The term 'isolated' requires the material to be removed from the environment in which it was present originally. For example, a polypeptide or nucleic acid, which is expressed in a cell, is not isolated. However, the same polypeptide or nucleic acid, when separated from some or all of the coexisting material occurring in the original environment, will be considered as isolated. It is in accordance with this definition to regard polypeptides and nucleic acids present in cell lysates as isolated. By 'purifying' a compound such as a polypeptide or a nucleic acid is meant increasing the degree of purity of a preparation of the compound by removing completely or partially at least one contaminant from the preparation. When applied to a preparation of a compound the term 'degree of purity' refers to its relative content by weight of the compound of interest, based on the total weight of the preparation. The degree of purity of a compound may be within the range of 1-100%, such as from 1-100%, 10-100%, 20-100%, 30-100%, 40-100%, 50-100%, 60-100%, 70-100%, 80-100% and 90-100%. 'Substantially pure' is herein used to describe a polypeptide or a nucleic acid with a degree of purity of at least 70%, such as at least 75%, at least 80%, at least 85%, at least 90% at least 95%, at least 99% or preferably substantially pure from other components. The % value herein indicates % (w/w).

The term 'sequence identity' indicates a quantitative measure of the degree of homology between two amino acid sequences or between two nucleic acid sequences of equal length. If the two sequences to be compared are not of equal length they must be aligned to give the best possible fit, allowing the insertion of gaps or, alternatively, truncation at the ends of the polypeptide sequences or nucleotide sequences. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$).

In all polypeptide or amino acid based embodiments of the invention the percentage of sequence identity between one or more sequences is based on alignment of the respective sequences as performed by clustalW software (www.ebi.ac.uk/clustalW/index.html) using the default settings of the program. These settings are as follows: Alignment=3Dfull, Gap Open 10.00, Gap Ext. 0.20, Gap separation Dist. 4, Protein weight matrix: Gonnet. With respect to the nucleotide-based embodiments of the invention, the percentage of sequence identity between one or more sequences is also based on alignments using the clustalW software with default settings. For nucleotide sequence alignments these settings are: Alignment=3Dfull, Gap Open 10.00, Gap Ext. 0.20, Gap separation Dist. 4, DNA weight matrix: identity (IUB).

By the term 'vector' is meant a phage, plasmid or virus DNA in which another DNA is inserted for introduction into bacterial or other cells for amplification (DNA cloning), and studies of expression as well as for production, hereunder large scale production, of a given compound.

Gender specific recognition: The term 'gender specific recognition' relates to specific plasma IgG antigen recognition that is higher in female adult women compared to men, both living in the same P. falciparum malaria endemic area. To test for gender specific antibody recognition of variant surface antigens (VSA) expressed on the surface of erythrocytes infected by a P. falciparum isolate, line, or clone, the level of specific recognition of VSA expressed by the isolate/line/clone in question in a panel of individual plasma samples is determined by flow cytometry (Staalsoe et al. 1999). The isolate/line/clone is said to show gender specific antibody recognition, if there is a statistically significant (Multiple linear regression analysis, $P<0.05$) effect of gender on the level of VSA-specific IgG recognition in individual plasma samples.

A cloned, expressed and purified protein can also be said to be "gender specificly recognised", this is tested by ELISA by testing the levels of antigen specific IgG in sera from for example 30 women and 30 men from an malaria endemic area. The protein is said to be gender specifically recognised when the level of antigen specific IgG is higher in women compared to men (Mann-Whitney U-test, $P<0.05$).

Placental parasite: A placental parasite or a placental isolate is a parasite that is gender specifically and parity dependant recognised as previously described.

Therapeutic antibodies: Following synthesis or expression and isolation or purification of a protein, the isolated or purified molecules can be used to generate antibodies that can be used prophylactic and therapeutic with respect to PAM. One possible effect of such a therapeutically effective dose of an antibody is the inhibition of adhesion of parasites to the placenta.

Therapeutic polypeptides: Following synthesis or expression and isolation or purification of a protein, the isolated or purified molecules can be used prophylactic and therapeutic applicability with respect to PAM. One possible effect of such a therapeutically effective dose of an polypeptide is the inhibition of adhesion of parasites to the placenta. Such a protein could be a polypeptide, which is identical to VAR2CSA or sequences substantially identical to sequence SEQ ID NO.: 2

Antisense and siRNA: Antisense nucleic acids can be administered as vaccine, therapeutically or prophylactic.

The antisense nucleic acids should have a length and melting temperature sufficient to permit formation of an intracellular duplex having sufficient stability to inhibit the expression of the mRNA in the duplex. Antisense molecules are obtained from a nucleotide sequence encoding VAR2CSA or sequences substantially homologous to sequence SEQ ID NO.: 1 or SEQ ID NO.: 3 as well as any other recodonised sequence encoding an amino acid sequence identical to SEQ ID NO.:2 by reversing the orientation of the coding region with respect to a promoter so as to transcribe the opposite strand from that which is normally transcribed in the cell. This product will inhibit expression of VAR2CSA and thus hinder binding of parasites to placenta. The expression of VAR2CSA and binding of parasites can also be inhibited by administering small interference RNA causing RNA interference by hybridisation and subsequent degradation of target mRNA.

Immune response: in the present context, the term 'immune response' is used in its broadest meaning referring to the response that occurs in the human body as reaction to its contact with a foreign substance. An immune response comprises the activation of B-lymphocytes and/or T-cells. Activation of B-lymphocytes can result in production of antibodies that can target an antigen. T-cells can be CD8+ or CD4+ or CD8−/CD4−. Activation of an immune response also comprises the activation of macrophages and/or the production of specific T and B memory cells.

Medicament relates to any composition comprising any of the polypeptides and/or nucleic acids describe herein for treatment of malaria and/or preventition of initiation of malaria and/or prophylaxis of malaria infection.

'VSA' refers to variant surface antigens expressed on the surface of RBC infected by *Plasmodium falciparum*. In the present context the variant surface antigen is PfEMP1.

'Serological phenotype' refers to the antibody profile obtained by FACS analysis of RBC infected by *P. falciparum* expressing VSA on the surface of said RBC.

3D7 refers to a specific laboratory isolate of a *Plasmodium falciparum* 3D7, which is a long-term clone derived from *P. falciparum* NF54 isolated from a Dutch malaria patient (Delemarre and Van der Kaay, 1979).

Unless otherwise defined herein or below in the remainder of the specification, all technical and scientific terms used herein have the same meaning as commonly understood by those of ordinary skill in the art to which the invention belongs.

A "polynucleotide sequence" (e.g., a nucleic acid, polynucleotide, oligonucleotide, etc.) is a polymer of nucleotides comprising nucleotides A,C,T,U,G, or other naturally occurring nucleotides or artificial nucleotide analogues, or a character string representing a nucleic acid, depending on context. Either the given nucleic acid or the complementary nucleic acid can be determined from any specified polynucleotide sequence. Numbering of a given amino acid polymer or nucleotide polymer "corresponds to" or is "relative to" the numbering of a selected amino acid polymer or nucleic acid polymer when the position of any given polymer component (e.g., amino acid, nucleotide, also referred to generically as a "residue") is designated by reference to the same or an equivalent position in the selected amino acid or nucleotide polymer, rather than by the actual numerical position of the component in the given polymer. Thus, for example, the numbering of a given amino acid position in a given polypeptide sequence corresponds to the same or equivalent amino acid position in a selected polypeptide sequence used as a reference sequence.

A "variant" is a polypeptide comprising a sequence, which differs (by deletion of an amino acid, insertion of an amino acid, and/or substitution of an amino acid for a different amino acid) in one or more amino acid positions from that of a parent polypeptide sequence. The variant sequence may be a non-naturally occurring sequence, i.e., a sequence not found in nature.

"Naturally occurring" as applied to an object refers to the fact that the object can be found in nature as distinct from being artificially produced by man. For example, a polypeptide or polynucleotide sequence that is present in an organism (including viruses, bacteria, protozoa, insects, plants or mammalian tissue) that can be isolated from a source in nature and which has not been intentionally modified by man in the laboratory is naturally occurring. "Non-naturally occurring" as applied to an object means that the object is not naturally-occurring—i.e., the object cannot be found in nature as distinct from being artificially produced by man.

A "fragment" or "subsequence" refers to any portion of a given sequence. It is to be understood that a fragment or subsequence of a sequence will be shorter that the sequence itself by at least one amino acid or one nucleic acid residue. Thus, a fragment or subsequence refers to a sequence of amino acids or nucleic acids that comprises a part of a longer sequence of amino acids (e.g., polypeptide) or nucleic acids (e.g., polynucleotide) respectively.

In one aspect, a "substantially pure" or "isolated" nucleic acid (e.g., RNA or DNA), polypeptide, protein, or composition also means where the object species (e.g., nucleic acid or polypeptide) comprises at least about 50, 60, or 70 percent by weight (on a molar basis) of all macromolecular species present. A substantially pure or isolated composition can also comprise at least about 80, 90, or 95 percent by weight of all macromolecular species present in the composition. An isolated object species can also be purified to essential homogeneity (contaminant species cannot be detected in the composition by conventional detection methods) wherein the composition consists essentially of derivatives of a single macromolecular species. The term "purified" generally denotes that a nucleic acid, polypeptide, or protein gives rise to essentially one band in an electrophoretic gel. It typically means that the nucleic acid, polypeptide, or protein is at least about 50% pure, 60% pure, 70% pure, 75% pure, more preferably at least about 85% pure, and most preferably at least about 99% pure.

The term "isolated nucleic acid" may refer to a nucleic acid (e.g., DNA or RNA) that is not immediately contiguous with both of the coding sequences with which it is immediately contiguous (i.e., one at the 5' and one at the 3' end) in the naturally occurring genome of the organism from which the nucleic acid of the invention is derived. Thus, this term includes, e.g., a cDNA or a genomic DNA fragment produced by polymerase chain reaction (PCR) or restriction endonuclease treatment, whether such cDNA or genomic DNA fragment is incorporated into a vector, integrated into the genome of the same or a different species than the organism, including, e.g., a virus, from which it was originally derived, linked to an additional coding sequence to form a hybrid gene encoding a chimeric polypeptide, or independent of any other DNA sequences. The DNA may be double-stranded or single-stranded, sense or anti-sense.

A "recombinant polynucleotide" or a "recombinant polypeptide" is a non-naturally occurring polynucleotide or polypeptide that includes nucleic acid or amino acid sequences, respectively, from more than one source nucleic acid or polypeptide, which source nucleic acid or polypeptide can be a naturally occurring nucleic acid or polypeptide, or can itself have been subjected to mutagenesis or other type of modification. A nucleic acid or polypeptide may be deemed "recombinant" when it is artificial or engineered, or derived from an artificial or engineered polypeptide or nucleic acid. A recombinant nucleic acid (e.g., DNA or RNA) can be made by the combination (e.g., artificial combination) of at least two segments of sequence that are not typically included together, not typically associated with one another, or are otherwise typically separated from one another. A recombinant nucleic acid can comprise a nucleic acid molecule formed by the joining together or combination of nucleic acid segments from different sources and/or artificially synthesized. A "recombinant polypeptide" (or "recombinant protein") often refers to a polypeptide (or protein) that results from a cloned or recombinant nucleic acid or gene. The source polynucleotides or polypeptides from which the different nucleic acid or amino acid sequences are derived are sometimes homologous (I.e., have, or encode a polypeptide that encodes, the same or a similar structure and/or function), and are often from different isolates, serotypes, strains, species, of organism or from different disease states, for example.

The term "recombinant" when used with reference, e.g., to a cell, nucleotide, vector, protein, or polypeptide typically indicates that the cell, nucleotide, or vector has been modified by the introduction of a heterologous (or foreign) nucleic acid or the alteration of a native nucleic acid, or that the protein or polypeptide has been modified by the introduction of a heterologous amino acid, or that the cell is derived from a cell so modified. Recombinant cells express nucleic acid sequences (e.g., genes) that are not found in the native (non-recombinant) form of the cell or express native nucleic acid sequences (e.g., genes) that would be abnormally expressed under-expressed, or not expressed at all. The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

The term "recombinantly produced" refers to an artificial combination usually accomplished by either chemical synthesis means, recursive sequence recombination of nucleic acid segments or other diversity generation methods (such as, e.g., shuffling) of nucleotides, or manipulation of isolated segments of nucleic acids, e.g., by genetic engineering techniques known to those of ordinary skill in the art. "Recombinantly expressed" typically refers to techniques for the production of a recombinant nucleic acid in vitro and transfer of the recombinant nucleic acid into cells in vivo, in vitro, or ex vivo where it may be expressed or propagated.

The term "upregulated" in the aspects of the present invention refers to detection of a transcript by quantitative RT-PCR of any of the malaria parasite nucleotides of the present invention, wherein the nucleotide transcription level is evaluated, when compared to a housekeeping gene such as but not limited seryl-tRNA-transferase. When a transcription level is less than 100 times that of the housekeeping gene, the evaluation is excluded. Any transcription level above this, wherein there is a difference of at least 2 times between the transcription level of the malaria parasite var gene in the parasite culture of interest eg the CSA selected and gender specifically recognised 3D7 parasite culture as compared to the control parasite culture eg the non-geneder specifically recognised 3D7 parasite culture, said gene is upregulated.

The term "translationally upregulated" in the aspects of the present invention refers to detection of a peptide or protein of any of the malaria parasite peptides or proteins of the present invention, wherein the peptide or protein detected by western blot, ELISA or IFA can be demonstrated to be increasingly expressed in parasite preparation of a parasite culture of interest eg the CSA selected and gender specifically recognised 3D7 parasite culture as compared to the control parasite culture eg the non-geneder specifically recognised 3D7 parasite culture as evaluated by those of ordinary skilled in the art.

An "immunogen" refers to a substance capable of provoking an immune response, and includes, e.g., antigens, autoantigens that play a role in induction of autoimmune diseases, and tumor-associated antigens expressed on cancer cells. An immune response generally refers to the development of a cellular or antibody-mediated response to an agent, such as an antigen or fragment thereof or nucleic acid encoding such agent. In some instances, such a response comprises a production of at least one or a combination of CTLs, B cells, or various classes of T cells that are directed specifically to antigen-presenting cells expressing the antigen of interest.

An "antigen" refers to a substance that is capable of eliciting the formation of antibodies in a host or generating a specific population of lymphocytes reactive with that substance. Antigens are typically macromolecules (e.g., proteins and polysaccharides) that are foreign to the host.

An "adjuvant" refers to a substance that enhances an antigen's immune-stimulating properties or the pharmacological effect(s) of a drug. An adjuvant may non-specifically enhance the immune response to an antigen. "Freund's Complete Adjuvant," for example, is an emulsion of oil and water containing an immunogen, an emulsifying agent and mycobacteria. Another example, "Freund's incomplete adjuvant," is the same, but without mycobacteria.

An "immunogenic composition" refers to a composition that will evoke an immune response when administered to a subject possessing an immune system.

A vector is a component or composition for facilitating cell transduction or transfection by a selected nucleic acid, or expression of the nucleic acid in the cell. Vectors include, e.g., plasmids, cosmids, viruses, YACS, bacteria, poly-lysine, etc. An "expression vector" is a nucleic acid construct or sequence, generated recombinantly or synthetically, with a series of specific nucleic acid elements that permit transcription of a particular nucleic acid in a host cell. The expression vector can be part of a plasmid, virus, or nucleic acid fragment. The expression vector typically includes a nucleic acid to be transcribed operably linked to a promoter. The nucleic acid to be transcribed is typically under the direction or control of the promoter.

"Substantially the entire length of a polynucleotide sequence" or "substantially the entire length of a polypeptide sequence" refers to at least about 50%, generally at least about 60%, 70%, or 75%, usually at least about 80%, or typically at least about 85%, 90%, 91%, 92%, 93%, 94%, 95%, 96%, 97%, 98%, 99%, 99.5% or more of a length of a polynucleotide sequence or polypeptide sequence.

The term "immunoassay" includes an assay that uses an antibody or immunogen to bind or specifically bind an antigen. The immunoassay is typically characterized by the use of specific binding properties of a particular antibody to isolate, target, and/or quantify the antigen.

The term "homology" generally refers to the degree of similarity between two or more structures. The term "homologous sequences" refers to regions in macromolecules that have a similar order of monomers. When used in relation to nucleic acid sequences, the term "homology" refers to the degree of similarity between two or more nucleic acid sequences (e.g., genes) or fragments thereof. Typically, the degree of similarity between two or more nucleic acid sequences refers to the degree of similarity of the composition, order, or arrangement of two or more nucleotide bases (or other genotypic feature) of the two or more nucleic acid sequences. The term "homologous nucleic acids" generally refers to nucleic acids comprising nucleotide sequences having a degree of similarity in nucleotide base composition, arrangement, or order. The two or more nucleic acids may be of the same or different species or group. The term "percent homology" when used in relation to nucleic acid sequences, refers generally to a percent degree of similarity between the nucleotide sequences of two or more nucleic acids. When used in relation to polypeptide (or protein) sequences, the term "homology" refers to the degree of similarity between two or more polypeptide (or protein) sequences (e.g., genes) or fragments thereof. Typically, the degree of similarity between two or more polypeptide (or protein) sequences refers to the degree of similarity of the composition, order, or arrangement of two or more amino acid of the two or more polypeptides (or proteins). The two or more polypeptides (or proteins) may be of the same or different species or group. The term "percent homology" when used in relation to polypeptide (or protein) sequences, refers generally to a percent degree of similarity between the amino acid sequences of two or more polypeptide (or protein) sequences.

The term "homologous polypeptides" or "homologous proteins" generally refers to polypeptides or proteins, respectively, that have amino acid sequences and functions that are similar. Such homologous polypeptides or proteins may be related by having amino acid sequences and functions that are similar, but are derived or evolved from different or the same species using the techniques described herein.

The term "subject" as used herein includes, but is not limited to, an organism; a mammal, Including, e.g., a human, non-human primate (e.g., baboon, orangutan, monkey), mouse, pig, cow, goat, cat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

The term "pharmaceutical composition" means a composition suitable for pharmaceutical use in a subject, including an animal or human. A pharmaceutical composition generally comprises an effective amount of an active agent and a carrier, including, e.g., a pharmaceutically acceptable carrier.

A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such as a nucleic acid, vector, gene, polypeptide, protein, substance, or composition thereof that, when administered to a subject who does not display signs or symptoms of pathology, disease or disorder, or who displays only early signs or symptoms of pathology, disease, or disorder, diminishes, prevents, or decreases the risk of the subject developing a pathology, disease, or disorder.

A "prophylactically useful" agent or compound (e.g., nucleic acid or polypeptide) refers to an agent or compound that is useful in diminishing, preventing, treating, or decreasing development of pathology, disease or disorder.

A "therapeutic treatment" is a treatment administered to a subject who displays symptoms or signs of pathology, disease, or disorder, in which treatment is administered to the subject for the purpose of diminishing or eliminating those signs or symptoms of pathology, disease, or disorder. A "therapeutic activity" is an activity of an agent, such as a nucleic acid, vector, gene, polypeptide, protein, substance, or composition thereof, that eliminates or diminishes signs or symptoms of pathology, disease or disorder, when administered to a subject suffering from such signs or symptoms. A "therapeutically useful" agent or compound (e.g., nucleic acid or polypeptide) indicates that an agent or compound is useful in diminishing, treating, or eliminating such signs or symptoms of a pathology, disease or disorder.

The term "gene" broadly refers to any segment of DNA associated with a biological function. Genes include coding sequences and/or regulatory sequences required for their expression. Genes also include non-expressed DNA nucleic acid segments that, e.g., form recognition sequences for other proteins (e.g., promoter, enhancer, or other regulatory regions). Genes can be obtained from a variety of sources, including cloning from a source of interest or synthesizing from known or predicted sequence information, and may include sequences designed to have desired parameters.

Generally, the nomenclature used hereafter and the laboratory procedures in cell culture, molecular genetics, molecular biology, nucleic acid chemistry, and protein chemistry described below are those well known and commonly employed by those of ordinary skill in the art. Standard techniques, such as described in Sambrook et al., Molecular Cloning—A Laboratory Manual (2nd Ed.), Vols. 1-3, Cold Spring Harbor Laboratory, Cold Spring Harbor, N.Y., 1989 (hereinafter "Sambrook") and Current Protocols in Molecular Biology, F. M. Ausubel et al., eds., Current Protocols, a joint venture between Greene Publishing Associates, inc. and John Wiley & Sons, inc. (1994, supplemented through 1999) (hereinafter "Ausubel"), are used for recombinant nucleic acid methods, nucleic acid synthesis, cell culture methods, and transgene incorporation, e.g., electroporation, injection, gene gun, impressing through the skin, and lipofection. Generally, oligonucleotide synthesis and purification steps are performed according to specifications. The techniques and procedures are generally performed according to conventional methods in the art and various general references, which are provided throughout this document. The procedures therein are believed to be well known to those of ordinary skill in the art and are provided for the convenience of the reader.

As used herein, an "antibody" refers to a protein comprising one or more polypeptides substantially or partially encoded by immunoglobulin genes or fragments of immunoglobulin genes. The term antibody is used to mean whole antibodies and binding fragments thereof. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 KDa) and one "heavy" chain (about 50-70 KDa). The N-terminus of each chain defines a variable region of about 100 to 110 or more amino acids primarily responsible for antigen recognition. The terms variable light chain (VL) and variable heavy chain (VH) refer to these light and heavy chains, respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region. The Fc portion of the antibody molecule corresponds largely to the constant region of the immunoglobulin heavy chain, and is responsible for the antibody's effector function (see, Fundamental immunology, W. E. Paul, ed., Raven Press, New York (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies.

Antibodies also include single-armed composite monoclonal antibodies, single chain antibodies, including single chain Fv (sFv) antibodies in which a variable heavy and a variable light chain are joined together (directly or through a peptide linker) to form a continuous polypeptide, as well as diabodies, tribodies, and tetrabodies (Pack et al. (1995) J Mol Biol 246:28; Biotechnol 11:1271; and Biochemistry 31:1579). The antibodies are, e.g., polyclonal, monoclonal, chimeric, humanized, single chain, Fab fragments, fragments produced by an Fab expression library, or the like. The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

An "antigen-binding fragment" of an antibody is a peptide or polypeptide fragment of the antibody that binds an antigen. An antigen-binding site is formed by those amino acids of the antibody that contribute to, are involved in, or affect the binding of the antigen. See Scott, T. A. and Mercer, E. I., Concise Encyclopedia: Biochemistry and Molecular Biology (de Gruyter, 3d ed. 1997), and Watson, J. D. et al., Recombinant DNA (2d ed. 1992) [hereinafter "Watson, Recombinant DNA"], each of which is incorporated herein by reference in its entirety for all purposes.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample. A nucleic acid is "operably linked" when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

The term "identical" or "identity," in the context of two or more nucleic acid or polypeptide sequences, refers to two or more sequences or subsequences that are the same or have a specified percentage of amino acid residues or nucleotides that are the same, when compared and aligned for maximum correspondence, as measured using one of the following sequence comparison algorithms or by visual inspection.

The term "serum" is used in its normal meaning, i.e. as blood plasma without fibrinogen and other clotting factors.

The term 'effective amount' refers to an amount or concentration of a substance such as an amino acid sequence, nucleotide sequence or an antibody, which is effective to produce a protective prophylactic or therapeutic response with respect to the disease malaria. In general, an effective amount of the substance, which is administered to a human subject, will vary depending upon a number of factors associated with that subject, including whether the subject has previously been exposed to Plasmodium falciparum. The person of ordinary skill in the art can determine an effective amount of the substance by varying the dosage of the product and measuring the resulting cellular and humoral immune and/or therapeutic responses subsequent to administration. In particular, the concentration range of an immunogenic substance is chosen so as to enhance the likelihood of eliciting an immunogenic response e.g. vaccinating the recipient for a long period of time, without causing a malaria infection in the vaccine recipient.

By 'RT-PCR' is meant as method that reverse transcribes RNA into cDNA. This is done by mixing and incubating a mRNA template with specific or random nucleotide primers, dNTP, and a reverse transcriptase enzyme (such as Superscript II).

By 'real time quantitative PCR' is meant a method including a fluorescent DNA intercalating dye in a PCR reaction mix. This method measures incorporated fluorescens at the end of each cycle making it possible to calculate the copy number of mRNA molecules in the original starting sample.

By the term "malaria" is meant any infection of a RBC in a subject, caused by Plasmodium falciparum.

PCR and RT-PCR

The polymerase chain reaction uses two oligonucleotide primers that hybridise to opposite strands and flank the target DNA sequence that is to be amplified. The elongation of the primers is catalyzed by a heat-stable DNA polymerase (such as Taq DNA Polymerase). A repetitive series of cycles involving template denaturation, primer annealing, and extension of the annealed primers by the polymerase results in exponential accumulation of a specific DNA fragment. The ends of the fragment are defined by the 5' ends of the primers. Because the primer extension products synthesised in a given cycle can serve as a template in the next cycle, the number of target DNA copies approximately doubles every cycle (Roche Diagnostics). If a fluorescent DNA intercalating dye is added to the PCR reaction mix, then by measuring fluorescence at the end of each cycle the the copy number of the sample can be calculated, this method is called quantitative real time PCR. RNA cannot serve as a template for PCR, so it must first be reverse transcribed into cDNA, this is done by mixing and incubating the mRNA template with a specific or random nucleotide primer, dNTP and a reverse transcriptase enzyme.

ELISA

Enzyme-linked-immunosorbent serologic assay—an assay that relies on an enzymatic conversion reaction and is used to detect the presence of specific substances. One type of ELISA is the two-antibody "sandwich" ELISA. This assay is used to determine the antigen concentration in unknown samples. The assay is done by coating a microtiter plate with antibody, antigen is then added and allowed to complex with the bound antibody. Unbound products are then removed with a wash, and a labeled second antibody (the "detection" antibody) is allowed to bind to the antigen, thus completing the "sandwich". The assay is then quantitated by measuring the amount of labeled second antibody bound to the matrix, through the use of a colorimetric substrate. In other variants of the ELISA, the plate can be coated with antigen and specific antibodies can be detected by incubating the plate with a bodily fluid. Unbound antibodies are then removed with a wash, and a labeled second antibody (the "detection" antibody) is allowed to bind to the primary antibody. The assay is then quantitated by measuring the amount of labeled second antibody bound to the matrix, through the use of a colorimetric substrate.

RIA

The basic principle of a radioimmunoassay (RIA) is the use of radiolabeled Abs or Ags to detect Ag:Ab reactions. The Abs or Ags are labeled with the 125I (iodine-125) isotope, and the presence of Ag:Ab reactions is detected using a gamma counter. RIAs can be performed in solution as well on filters. In solution the Ag:Ab complexes are precipitate and the amount of radioactivity in the supernatant is measured.

Dip Stick Test

Is a method of detecting specific antigen, antibody, DNA or mRNA from a bodily fluid sample. A nucleic acid, antigen or antibody is bound to the membrane of the dip stick and contact to a labelled or unlabelled bodily fluid is allowed for a given time. The nucleic acid, antigen or antibody bound on the membrane can in some methods be hybridised to nucleic acid, antigen or antibody labelled with a dye.

Hybridization Assay

A hybridisation assay utilizes the base pairing principle, where adenin hybridises with thymin and guanine with cytosin or analogues hereof. Serum can be tested for the presence of RNA or DNA by hybridisation together with a probe, labelled or unlabelled, solid phase or liquid phase.

DETAILED DESCRIPTION OF THE INVENTION

The inventive concept disclosed in the present application is based on the unexpected observation that the mRNA and protein expression of a specific *Plasmodium falciparum* var gene, var2csa, a member of an unusual class of PfEMP-1 types is up-regulated in all parasite lines and clones selected for CSA adhesion and expressed at high levels by placental parasites. This gene product is gender specifically and parity dependently recognised by immune serum from malaria-endemic areas. These observations indicate that proteins of the VAR2CSA family encoded by var2csa-type var genes are responsible for adhesion of iRBC to CSA. It also follows from these findings that such proteins are useful as therapeutic and prophylactic agents as well as biological tools and diagnostic agents for the study, treatment and prevention of PAM malaria.

Polypeptide Molecules of the invention

In its broadest aspect, the present invention relates to a polypeptide comprising at least one amino acid sequence selected from the group consisting of a) SEQ ID NO.: 2; and b) a sequence having at least 70% sequence identity to a); and c) sub-sequences of a) or b) with a minimum length of 6 amino acids; and d) sub-sequences of a) or b) comprising at least one B-cell epitope;

with the proviso that the amino acid sequence of SEQ ID NO.: 2 is excluded.

The amino acid sequence SEQ ID NO.: 2 comprises sequences encoded by exon I and exon II, 6 DBL domains, a transmembrane domain and the conserved ATS domain. For the present and any of the following aspects of the invention it applies that the ATS domain could be excluded from the scope of any embodiments of the present invention. The ATS domain consists of amino acids No. 2667 to 3056 of SEQ ID NO.: 2.

Said sub-sequences may be at least 100 amino acids in length and at least 70% identical to a region of comparable length within the sequence of SEQ ID NO.: 2.

For the present and any of the following aspects of the invention it applies that the preferred polypeptides of the invention have the ability to bind to CSA and may further be subject to gender-specific and parity dependent recognition by antibodies in sera isolated from subjects exposed to *Plasmodium falciparum*.

The predicted amino acid sequence of VAR2CSA in the parasite line NF54 is provided in the sequence listing as SEQ ID NO.: 2. For all the aspects of the invention, it is apparent that the polypeptides of the invention, which form the basis of the described embodiments of the invention may be less or equal to any length between 9-1250 amino acids, such as but not limited to less than or equal to 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 225, 250, 275, 300, 350, 400, 450, 500, 600, 700, 800, 900, 1000, 1250 amino acids in length.

With respect to all aspects of the invention it may be preferred that the polypeptides of the invention may have a length of 6-10, 6-20, 6-30, 6-40, 6-50, 6-60, 6-70, 6-80, 6-90, 6-100, 6-110, 6-120, 6-130, 6-140, 6-150, 6-160, 6-170, 6-180, 6-190, 6-200, 6-225, 6-250, 6-275, 6-300, 6-350, 6-400, 6-450, 6-500, 6-5 600, 6-700, 6-800, 6-900, 6-1000 or 6-1250 amino acids.

In addition to these fragments or sub-sequences of the polypeptide of the invention larger proteins comprising such sub-sequences as part of their sequence, are also embodiments of the present invention.

Preferred embodiments of the present invention include specific sub-sequences of the polypeptide of the invention having a minimum length of 6 amino acids such as sub-sequences that are at least 100 amino acids long. In even more preferred embodiments of the invention, these sub-sequences can be shown by known molecular biological techniques to be involved in the interaction with endothelial receptors, hereunder CSA. It is anticipated that relatively short sequences within the VAR2CSA protein are responsible for mediating adhesion to CSA. In particular, it is possible that certain DBL domains or parts hereof are responsible for the adhesion. In other preferred embodiments of the invention, the sub-sequences of the polypeptide of the invention can be shown to possess one or more antigen epitopes. In particular, such epitopes may be B-cell epitopes. Optionally, the sub-sequences may also comprise one or more T-cell epitopes alone or in combination with the B-cell epitopes. Finally, also larger polypeptides comprising the polypeptide of the invention or sub-sequences hereof with antigen epitopes and/or sequences involved in interaction with CSA are embodiments of the present invention.

It is also apparent that the polypeptide sequences of the invention can be present in the form of fusion proteins. In a further preferred embodiment, this fusion protein will comprise polypeptide sequences, which will facilitate the purification or detection of the protein. These polypeptide sequences may be but are not limited to tags that will facilitate purification and detection using commercially available systems such as the HA- ,-c-myc, His or GST tags.

The polypeptide embodiments of the present invention can therefore exhibit a vast degree of sequence identity to the full-length VAR2CSA sequence. It can for instance be appreciated that a fusion protein carrying within its sequence one or more B-cell epitopes and or regions of the polypeptide of the invention that are involved in adhesion to CSA will have a relatively low overall degree of sequence identity to full-length VAR2CSA. For all the aspects of the invention, it is thus apparent that the polypeptides of the invention may include sequences, which show anywhere between 1-100% sequence identity, such as at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 99% or preferably 100% sequence identity to VAR2CSA or a fragment or sub-sequence thereof.

Preferred embodiments of the invention comprise a fragment of the polypeptide of the invention that is involved in interaction with endothelial receptors such as CSA and thus exhibits adhesion to CSA. Preferably, the sequence has at least 70% sequence identity to a region of comparable length within the sequence of SEQ ID NO.: 2.

A more preferred embodiment pertains to an amino acid sequence selected from the group consisting of
- a) SEQ ID NO.: 2; and
- b) a sequence having at least 80% sequence identity to a); and
- c) a sub-sequence of a) or b) with a minimum length of 20 amino acids with the proviso that SEQ ID NO.: 2 and sub-sequences of a) and b), which, when aligned to the best possible fit with SEQ ID NO.: 2, comprise a region which align with less than 90% sequence identity to amino acids No. 2602-2622 of SEQ ID NO.: 2, be excluded.

It is further preferred that the amino acid sequence is capable of inducing an immune response against a molecule expressed on the surface of an intact erythrocyte infected by a placental parasite. It is equally preferred that the amino acid sequence is capable of inducing an immune response against a molecule expressed on the surface of an intact erythrocyte infected by a placental parasite.

In particularly preferred embodiments the sub-sequence comprises at least one B-cell epitope and/or at least one T-cell epitope, and in other particularly preferred embodiments it comprises one or more GAG-binding motifs.

It is further preferred that the amino acid sequence does not comprise a CIDR domain or DBL-γ domain and that the amino acid sequence is gender specifically recognised. Finally, It is preferred that the amino acid sequence is recognised in a parity dependent manner. In one embodiment of the invention, the sub-sequences of a) and b) are at least 100 amino acids in length and at least 80% identical to a region of comparable length within the sequence of SEQ ID NO.: 2.

It is understood that the polypeptide fragments of the invention may possess one or more types of post-translational modifications when expressed on the cell surface. These modifications may comprise, but are not limited to, glycosylation, phosphorylation, acylation, cross-linking, proteolytic cleavage, linkage to an antibody molecule, a membrane molecule, or another ligand.

The embodiments of the present invention thus relate to polypeptides of the PfEMP1 class or sub-sequences hereof as well as nucleic acid molecules encoding such polypeptides or sub-sequences, wherein said polypeptides and sub-sequences comprise structures that are involved directly or indirectly in the binding to CSA. The var2csa gene is a member of an unusual class of var genes and, in their widest perspective, the embodiments of the invention thus relate to nucleic acid molecules, which are characteristic in that they do not belong to the var1 gene subfamily as defined in Salanti et al. 2002. Furthermore, nucleic acid molecules, which are complementary to the nucleic acid molecules of the invention as described above as well as polypeptides encoded by these nucleic acid molecules are within the scope of the invention.

Nucleic Acid Molecules

One embodiment of the present invention relates to a nucleic acid molecule comprising at least one nucleotide sequence selected from the group consisting of
- a) SEQ ID NO.: 1 or a sequence complementary thereof; and
- b) a nucleotide sequence having at least 70% sequence identity to a); and
- c) sub-sequences of a) or b) with a minimum length of 18 nucleic acids; and
- d) sub-sequences of a) or b) which comprises at least one sequence encoding a B-cell epitope;

with the proviso that the nucleotide sequence of SEQ ID NO.: 1 is excluded.

The nucleic acid sequence SEQ ID NO.: 1 comprises exon I and exon II. For the present and any of the following aspects of the invention it applies that the exon II could be excluded from the scope of any embodiments of the present invention. The exon II domain consists of amino acids No. 8001 to 9171 of SEQ ID NO.: 1

It further applies that the nucleic acid sequence having the EMBL database accession number BQ739499; PfESToab46 g01.y1 *Plasmodium falciparum* 3D7 asexual cDNA *Plasmodium* DE *falciparum* cDNA 5' similar to TR:Q26030 Q26030 VARIANT SURFACE PROTEIN, deposited by Tang, K. et al. could be excluded from the scope of any embodiment of the present invention.

In particular, the nucleic acid molecule may comprise sub-sequences, which are at least 300 nucleotides in length and at least 70% identical to a region of comparable length within the sequence of SEQ ID NO.: 1.

The CDNA sequence encoding VAR2CSA in the parasite line NF54 is provided in the sequence listing as SEQ ID NO.: 1. Again, it is apparent for all the aspects of the invention that the nucleic acid molecules of the invention may be less than or equal to any length between 9-4500 nucleotides, such as less than or equal to 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 225, 250, 275, 300, 350, 400, 450, 500, 600, 700, 800, 900, 1000, 1250, 1500, 1750, 2000, 2500, 3000, 3500, 4000, 4500 nucleotides in length.

Still with respect to all aspects of the invention it may be preferred that the nucleic acid molecules of the invention may have a length of 6-10, 6-20, 6-30, 6-40, 6-50, 6-60, 6-70, 6-80, 6-90, 6-100, 6-110, 6-120, 6-130, 6-140, 6-150, 6-160, 6-170, 6-180, 6-190, 6-200, 6-225, 6-250, 6-275, 6-300, 6-350, 6-400, 6-450, 6-500, 6-600, 6-700, 6-800, 6-900, 6-1000, 6-1250, 6-1500, 6-1750, 6-2000, 6-2500, 6-3000, 6-3500, 6-4000 or 6-4500 nucleotides.

In some embodiments of the invention, sub-sequences of the nucleic acid molecules of the invention have a minimum length of 18 nucleic acids and in other embodiments these sub-sequences are at least 300 nucleotides long. Preferred nucleic acid embodiments further Include nucleic acids encoding fragments of the polypeptide of the invention that are involved in interaction with endothelial receptors such as CSA and thus exhibit adhesion to CSA. In addition, it is an object of preferred embodiments that sub-sequences of the nucleic acid molecule of the invention comprise nucleic acids encoding one or more B-cell epitopes and/or one or more T-cell epitopes.

Some characteristic structures lie within the peptide sequence of VAR2CSA and therefore also within the nucleotide sequence encoding this peptide sequence. Such structures comprise, but are not necessarily limited to, a string of at least 2 consecutive DBL domains as the N-terminal domains. On the other hand, some common features have been identified for proteins encoded by the var1 gene subfamily including the CIDR domains and the DBL-γ domains. These features are not found within the amino acid sequence of VAR2CSA.

Further embodiments comprise nucleic acid molecules that complement full-length var2csa or sequences identical in part hereto as well as nucleic acid sequences that complement fragments of full-length var2csa or sequences identical in part hereto. Preferred complementary nucleic acid molecules of the invention comprise nucleic acid molecules that are complementary to fragments of var2csa, which have a nucleotide sequence that encodes a polypeptide or parts of a polypeptide that are involved in interaction with CSA. Additionally, preferred complementary nucleic acid molecules of the invention are complementary to sequences encoding one or more B-cell epitopes and/or one or more T-cell epitopes.

As discussed for the polypeptide-based compounds of the invention it is also apparent that the nucleotide based embodiments may represent only part of the full-length sequence. In addition these nucleotide sequences may be present in combination with exogenous sequences. For all the aspects of the invention, it is thus apparent that the nucleic acids molecules of the invention may include sequences that have anywhere between 1-100% sequence identity to the full-length sequence of var2csa, such as at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 97% or, preferably, 100% sequence identity to var2csa or a fragment or sub-sequence thereof.

Preferred embodiments of the invention comprise a nucleotide sequence that encodes a polypeptide, which is involved in interaction with endothelial receptors such as CSA and thus exhibits adhesion to CSA. The nucleotide sequence may have at least 70% sequence identity to a region of comparable length within the sequence of SEQ ID NO.: 1.

More preferred embodiment of the present invention pertains to a nucleotide sequence selected from the group consisting of
  a) SEQ ID NO.: 1; and
  b) a sequence having at least 80% sequence identity to a); and
  c) a sub-sequence of a) or b) with a minimum length of 30 nucleic acids with the proviso that SEQ ID NO.: 1 and sequences and sub-sequences of a) or b), which, when aligned to give the best possible fit with SEQ ID NO.: 1, comprise a region of 70 nucleic acid residues or less which align with less than 90% sequence identity to nucleic acids No. 7800-8001 of SEQ ID NO.: 1, and or comprise a region of 40 nucleic acid residues or less which align with less than 90% sequence identity to nucleic acids No. 600-660 of SEQ ID NO.: 1, and/or comprise a region of 30 base pairs which align with less than 90 % sequence identity to nucleic acids No.: 1495-1540 of SEQ ID NO.:1, be excluded.

Especially preferred is a nucleic acid sequence which is capable of inducing an immune response against a molecule expressed on the surface of an intact erythrocyte infected by a placental parasite.

In particularly preferred embodiments the sub-sequence encodes at least one B-cell epitope and/or at least one T-cell epitope, and in other particularly preferred embodiments it encodes one or more GAG-binding motifs.

It is further preferred that the nucleic acid sequence does not encode a sequence comprising a CIDR domain or DBL-γ domain and that the nucleic acid sequence encodes an amino acid sequence that is gender specifically recognised. Finally, it is preferred that nucleic acid sequence encodes an amino acid sequence, which is recognised in a parity dependent manner.

In one embodiment of the invention, the sub-sequences of a) and b) are at least 300 nucleic acids in length and at least 80% identical to a region of comparable length within the sequence of SEQ ID NO.: 1.

It is to be understood that the nucleotide sequence of SEQ ID NO.: 1 when present within the genome of the intact *Plasmodium falciparum* parasites as well as the polypeptide sequence of SEQ ID NO.: 2 when present in or on the surface of intact red blood cells infected with *P. falciparum* are excluded from the scope of the present invention. This applies to all embodiments of the invention described in the present application. Compounds of the invention may however comprise sub-sequences of SEQ ID NO.: 1 and sub-sequences of SEQ ID NO.: 2 isolated and/or purified from the *Plasmodium* parasites or infected RBC. In addition, recombinant polypeptides comprising sub-sequences of the amino acid sequence of SEQ ID NO.: 2 may be generated by use of the above-mentioned nucleic acid embodiments. These can be cloned into vectors by the use of cloning techniques known in the art. The sequence encoding the polypeptide of interest is thereby linked to a heterologous promoter sequence. It may be preferred to optimise the codon context and codon pairing for the particular expression system. With respect to the polypeptide embodiments of the invention the incorporation of a secretory leader sequence may also be of use. The vector can be an expression vector in any of the mammalian, yeast, amphibian, insect, parasite, plant, or bacterial expression systems known in the art. It is therefore apparent that, with the exception of *Plasmodium* infected RBC, prokaryotic and eukaryotic cells hereunder mammalian cells and transformed cell lines as well as cells in animals possessing nucleotide and/or amino acid embodiments described herein, are within the scope of the present invention.

Var2csa or homologues hereof can be expressed in different expression systems eukaryotic or prokaryotic. In some instances it could be an advantage to recodonize the var2csa sequence or homologues hereof for expression in other hosts than *P falciparum*. in one example the sequence can be optimised for expression in different yeast systems, human cell in vitro systems, insect cell systems, in these systems in could be an advantage to purify the protein before using it as an vaccine or therapeutically. In another example the sequence could be optimised for expression in plant derived systems—from these transgenic plants the whole plant organism might be ingested to activate the immune system against PAM parasites, or the proteins could be purified. Plant expression systems could for example be transgenic potatoes, soya been, tobacco, banana, crops used for animal feeding, or other plants that can be made transgenic with known methods. Var2csa or homologues hereof can be delivered to the plant by different means, in one case the DNA can be transferred by *Agrobacterium* T-DNA vectors or by shooting the DNA inside the nucleus of the plant cell. Transient expression can be obtained with different virus vectors transfection the plant cell.

In a further preferred embodiment nucleic acid sequence is a re-codonised sequence. Particularly preferred are sequences that are recodonised in order to enhance or optimise expression of the resulting protein or polypeptide in a given expression system. Accordingly, in an even more preferred embodiment of the present invention the nucleic acid sequence has been recodonised in order to enhance expression in an expression system selected from the group consisting of: Yeast systems, human cell in vitro systems, insect cell systems and plant expression systems.

An example of such a recodonised nucleic acid is provided in the form of SEQ ID NO.: 3. This sequence represents the entire exon 1 of VAR2CSA including nucleic acids 1 to 8000 subjected to full recodonisation facilitating the expression of VAR2CSA in eucaryotic organisms. Accordingly, a currently most preferred embodiment of the invention is the recodonised sequence of SEQ ID NO.: 3.

Propagation of the cells or cell lines described above may be performed with the intention of providing recombinant forms of one or more of the nucleic acid or polypeptide embodiments of the invention in amounts that are sufficient for further processing or purification. It is therefore within the scope of the present invention to provide preparations of compounds, which comprise polypeptides of the invention as well as nucleic acid molecules encoding these polypeptides. Preparations of such compounds may have a desired degree of purity referring to the relative amounts of the desired polypeptide and for instance whole cell proteins and unwanted variants of the desired polypeptide as defined above. The existence of a wide range of protein purification and concentration techniques is known to the skilled artisan. These techniques include gel electrophoresis, ion-exchange chromatography, affinity and immunoaffinity chromatography, ceramic hydroxyapatite chromatography, differential precipitation, molecular sieve chromatography, isoelectric focusing, gel filtration, and diafiltration.

For the various types of chromatography, the desired molecules are suspended in a buffer, which promotes adhesion of the molecules to the active surface of the resin and are then applied to the chromatography column. Removal of contaminants is performed by washing the resin in a buffer of intermediate ionic strength or pH. Elution of the desired molecules is performed by changing the ionic strength or pH of the buffer to values that will promote the dissociation of the molecules from the active surface of the resin used. In the case of immunoaffinity chromatography, the polypeptide may be purified by passage through a column containing a resin to which is bound antibodies which are specific for at least a portion of the polypeptide. Furthermore, His- or GST tags may be added to the polypeptides of the invention. Subsequently, the resulting fusion proteins can be purified by affinity chromatography on for instance glutathione sepharose 4B and HIS tag Metal Chelate Affinity Chromatography.

It is readily apparent that a person skilled in the art can create a nucleic acid molecules of virtually any length by ligating a nucleic acid molecule encoding VAR2CSA or any part thereof to an exogenous nucleotide sequence. Recombinant nucleic acid molecules generated by this approach are embodiments of the invention. A recombinant construct can be capable of replicating autonomously within a host cell or, alternatively, it can become integrated into the chromosomal DNA. Such a recombinant nucleic acid molecule can comprise a sequence of genomic DNA, cDNA, synthetic or semi-synthetic origin. Again, It is preferred that such nucleic acid molecules are encoding one or more B-cell epitopes and/or one or more T-cell epitopes. The nucleic acid embodiments of the present invention can be altered by genetic engineering so as to introduce substitutions, deletions and/or additions. In preferred embodiments of the invention, these alterations will provide for sequences encoding functionally equivalent molecules or molecules with the same or improved properties. Such changes of the polypeptide embodiments can be generated using techniques that are known to a person skilled in the art, including random mutagenesis and site-directed mutagenesis.

The use of recombinant polypeptides of the invention may be preferred when it is required that the preparations of these polypeptides are essentially free of any other antigen with which they are natively associated, i.e. free of any other antigen from *Plasmodium* parasites. As an alternative this may also be accomplished by synthesizing the polypeptide fragments by the well-known methods of solid or liquid phase peptide synthesis.

In some aspects, the present invention can be used to both inhibit the adhesion of iRBC to CSA and to generate an immune response directed at var2csa. It is therefore within the scope of the invention to provide uses of any of the polypeptides of the present invention as medicaments that are therapeutically or prophylactically useful or both.

Medicaments

An embodiment of the present invention thus relates to at least one amino acid sequence selected from the group consisting of
 a) SEQ ID NO.: 2; and
 b) a sequence having at least 70% sequence identity to a); and
 c) sub-sequences of a) or b) with a minimum length of 6 amino acids; and
 d) sub-sequences of a) or b) comprising at least one B-cell and/or T-cell epitope for use as a medicament.

It is preferred, that these sub-sequences have a minimum length of 6 amino acids and that they are at least 70% identical to a region of comparable length within the sequence of SEQ ID NO.: 2. it is even more preferred that sub-sequences are at least 100 amino acids in length.

A more preferred embodiment pertains to an amino acid sequence selected from the group consisting of
 a) SEQ ID NO.: 2; and
 b) a sequence having at least 80% sequence identity to a); and
 c) a sub-sequence of a) or b) with a minimum length of 10 amino acids for use as a medicament.

It may be preferred that sub-sequence of a) or b) have a minimum length of 20 amino acids.

It is further preferred that the amino acid sequence is capable of inducing an immune response against a molecule expressed on the surface of an intact erythrocyte infected by a placental parasite. It is equally preferred that the amino acid sequence is capable of inducing an immune response against a molecule expressed on the surface of an intact erythrocyte infected by a placental parasite.

In particularly preferred embodiments the sub-sequence comprises at least one B-cell epitope and/or at least one T-cell epitope, and in other particularly preferred embodiments It comprises one or more GAG-binding motifs.

It is further preferred that the amino acid sequence does not comprise a CIDR domain or DBL-γ domain or is derived from a gene or a protein which does not comprise a CIDR domain or DBL-γ domain, and that the amino acid sequence is gender specifically recognised. Finally, it is preferred that the amino acid sequence is recognised in a parity dependent manner.

It readily appears that any feature and characteristic that is described for such an amino acid sequence for use as a medicament will also apply by analogy to a method for prevention or treatment of a disease or disorder. A method for prevention or treatment of a disease or disorder constitutes an additional aspect of the present invention. A method for prevention or treatment of pregnancy associated malaria is a preferred embodiment of the present invention.

Alternatively, therapeutic and prophylactic effects can be obtained as a result of the expression of polypeptides of the invention within a diseased subject or a subject at risk of contracting malaria. Therefore, it is also within the scope of the invention to provide uses of any of the nucleic acid molecules of the present invention as medicaments that are therapeutically or prophylactically useful or both.

A preferred embodiment of the present invention thus relates to a nucleic acid molecule comprising at least one nucleotide sequence selected from the group consisting of
   a) SEQ ID NO.: 1 or a sequence complementary thereof; and
   b) a nucleotide sequence having at least 70% sequence identity to a); and
   c) sub-sequences of a) or b) with a minimum length of 18 nucleic acids; and
   d) sub-sequences of a) and b) which comprise at least one sequence encoding a B-cell epitope for use as a medicament.

These sub-sequences have a minimum length of 18 nucleic acids and they may be at least 70% identical to a region of comparable length within the sequence of SEQ ID NO.: 1. it is even more preferred that sub-sequences are at least 300 nucleotides in length.

An equally preferred embodiment of the present invention pertains to a nucleotide sequence selected from the group consisting of
   a) SEQ ID NO.: 1; and
   b) a sequence having at least 80% sequence identity to a); and
   c) a sub-sequence of a) or b) with a minimum length of 30 nucleic acids for use as a medicament.

Especially preferred is a nucleic acid sequence which is capable of inducing an immune response against a molecule expressed on the surface of an intact erythrocyte infected by a placental parasite.

In particularly preferred embodiments the sub-sequence encodes at least one B-cell epitope and/or at least one T-cell epitope, and in other particularly preferred embodiments it encodes one or more GAG-binding motifs.

It is further preferred that the nucleic acid sequence does not encode a sequence comprising a CIDR domain or DBL-γ domain and that the nucleic acid sequence encodes an amino acid sequence that is gender specifically recognised. Finally, it is preferred that nucleic acid sequence encodes an amino acid sequence, which is recognised in a parity dependent manner.

In a further preferred embodiment the nucleic acid sequence is a re-codonised sequence. Particularly preferred are sequences that are recodonised in order to enhance or optimise expression of the resulting protein or polypeptide in a given expression system. Accordingly, in an even more preferred embodiment of the present invention the nucleic acid sequence has been recodonised in order to enhance expression in an expression system selected from the group consisting of: Yeast systems, human cell in vitro systems, insect cell systems and plant expression systems An example of such a recodonised nucleic acid is provided in the form of SEQ ID NO.: 3. This sequence represents the entire exon 1 of VAR2CSA including nucleic acids 1 to 8000 subjected to full recodonisation facilitating the expression of VAR2CSA in eukaryotic organisms. Accordingly, a currently most preferred embodiment of the invention is the recodonised sequence of SEQ ID NO.: 3.

Pharmaceutical Compositions

Additional aspects of the present invention relate to pharmaceutical compositions based on any of the polypeptide embodiments of the invention. Preferably, such a composition comprises at least one amino acid sequence selected from the group consisting of
   a) SEQ ID NO.: 2; and
   b) a sequence having at least 70% sequence identity to a); and
   c) sub-sequences of a) or b) with a minimum length of 6 amino acids; and
   d) sub-sequences of a) or b) comprising at least one B-cell epitope.

It is preferred, however, that the sub-sequences have a minimum length of 6 amino acids and that they are at least 70% identical to a region of comparable length within the sequence of SEQ ID NO.: 2. it is even more preferred that sub-sequences are at least 100 amino acids in length.

Alternatively, the pharmaceutical composition according to the present invention may be based on any of the nucleotide embodiments of the invention. In a preferred embodiment, the pharmaceutical composition comprises a vector containing at least one nucleotide sequence selected from the group consisting of
   a) SEQ ID NO.: 1 or a sequence complementary thereof; and
   b) a nucleotide sequence having at least 70% sequence identity to a); and
   c) sub-sequences of a) or b) with a minimum length of 18 nucleic acids; and
   d) sub-sequences of a) and b) which comprise at least one sequence encoding a B-cell epitope.

It is preferred that these sub-sequences have a minimum length of 18 nucleic acids and that they are at least 70% identical to a region of comparable length within the sequence of SEQ ID NO.: 1. it is even more preferred that sub-sequences are at least 300 nucleotides in length.

In a particularly preferred embodiment the pharmaceutical composition as described above is an immunogenic composition. It is further preferred that the immunogenic composition comprises an amino acid sequence selected from the group consisting of
   a) SEQ ID NO.: 2; and
   b) a sequence having at least 80% sequence identity to a); and
   c) a sub-sequence of a) or b) with a minimum length of 10 amino acids It is even more preferred that the amino acid sequence is capable of inducing an immune response against a molecule expressed on the surface of an intact erythrocyte infected by a placental parasite. It is equally preferred that the amino acid sequence is capable of inducing an immune response against a molecule expressed on the surface of an intact erythrocyte infected by a parasite that has been selected for its ability to mediate adhesion to CSA.

In particularly preferred embodiments the sub-sequence comprises at least one B-cell epitope, and in other particularly preferred embodiments it comprises one or more GAG-binding motifs.

It is further preferred that the amino acid sequence does not comprise a CIDR domain or DBL-γ domain and that the amino acid sequence is gender specifically recognised. Finally, it is preferred that the amino acid sequence is recognised in a parity dependent manner.

Alternatively the pharmaceutical composition may comprise a nucleic acid sequence selected from the group consisting of a) SEQ ID NO.: 1; and
b) a sequence having at least 80% sequence identity to a); and
c) a sub-sequence of a) or b) with a minimum length of 30 nucleic acids Especially preferred is a nucleic acid sequence which is capable of inducing an immune response against a molecule expressed on the surface of an intact erythrocyte infected by a placenta parasite.

In particularly preferred embodiments the sub-sequence encodes at least one B-cell epitope and/or at least one T-cell epitope, and in other particularly preferred embodiments it encodes one or more GAG-binding motifs.

It is further preferred that the nucleic acid sequence does not encode a sequence comprising a CIDR domain or DBL-γ domain and that the nucleic acid sequence encodes an amino acid sequence that is gender specifically recognised. Finally, it is preferred that nucleic acid sequence encodes an amino acid sequence which is recognised in a parity dependent manner.

It is preferred that the immunogenic composition described above is characterised in that it induces an IgG/IgM antibody response.

In a further preferred embodiment the nucleic acid sequence is a re-codonised sequence and in a most preferred embodiment of the invention the nucleic acid sequence is the recodonised sequence of SEQ ID NO.: 3.

In a specially preferred embodiment, any of the pharmaceutical compositions described in the present application may further comprise a pharmaceutically acceptable carrier and/or an adjuvant.

Pharmaceutical compositions comprising the nucleotide and polypeptide embodiments of the invention can be produced by conventional techniques so that the said sequences are present as monomeric, multimeric or multimerised agents. Furthermore, antibodies generated from the polypeptide embodiments of the invention may constitute part of such pharmaceutical compositions. In addition to the active ingredients, pharmaceutical compositions may further comprise one or more physiologically acceptable carriers, proteins, supports, adjuvants as well as components that may facilitate the delivery of the active components of the compositions. As described above, a large number of adjuvants are available including but not limited to Freund's adjuvant, mineral gels such as aluminium hydroxide, and surface-active substances such as lysolecithin, pluronic polyols, polyanions, peptides, oil emulsions, keyhole limpet hemocyanin, and dinitrophenol. As a pharmaceutical composition, the nucleic add and peptide embodiments of the invention will be purified and processed through one or more formulation steps. A large variety of formulation buffers will be physiologically acceptable, such as phosphate, citrate, and other organic acids.

It is further understood that a pharmaceutical composition must be clinically safe. More specifically, it must be free of virus and bacteria that can cause infection upon administration of the composition to a subject. It will therefore be necessary to process the composition through on or more steps of virus filtration and/or inactivation. The removal of virus by filtration can be obtained by passing the composition through a nanofilter whereas virus inactivation can be accomplished by the addition of various detergents and/or solvents or other antiviral compounds to the composition.

The polypeptide embodiments of the invention may be used in their purified form to generate various types of antibodies, and it is understood that such antibodies will also be considered as compounds of the invention. These antibodies may include, but are not limited to polyclonal, monoclonal, chimeric, single chain, Fab fragments and fragments produced by a Fab expression library. A person skilled in the art knows that antibodies can be produced by immunisation of various hosts including goats, rabbits, rats, and mice.

Alternatively, antibodies, such as chimeric antibodies, and anybody fragments corresponding to antibodies generated in response to immunisation with the nucleic acid sequences or amino acid sequences of the invention or parts of such antibodies can be produced by recombinant processes well known in the art. Preferred antibody fragments do not contain the Fc region of the antibody molecule. The Fc region is responsible for effector functions of the immunoglobulin (Ig) molecule such as complement fixation, allergic responses and killer T cell activation. The smaller size of the antibody fragment may help improve tissue bioavailability, which may be critical for better dose accumulation in acute disease indications. Furthermore, they have reduced immunogenicity, they do not induce precipitation (Fab only) and they can be used for a variety of in vivo applications and immunoassays.

Antibody fragments can be produced via recombinant methods creating single chain antibodies ("ScFv"), in which the heavy and light chain Fv regions are connected, or by enzymatic digestion of whole antibody.

In particular, Fabs can be converted to whole Ig molecules. The light-chain gene and variable gene fragment of the heavy-chain sequence of each clone can be inserted into a eukaryotic expression vector containing a Ig constant region gene, for instance of human origin.

Such chimeric antibodies, which are of partially human origin are less immunogenic than wholly murine MAbs, and the fragments and single chain antibodies are also less immunogenic. All these types of antibodies are therefore less likely to evoke an immune or allergic response. Consequently, they are better suited for in vivo administration in humans than wholly animal antibodies, especially when repeated or long-term administration is necessary.

Humanized antibodies have a greater degree of human peptide sequences than do chimeric antibodies. In a humanized antibody, only the complementarity determining regions (CDRS) which are responsible for antigen binding and specificity are animal derived and have an amino acid sequence corresponding to the animal antibody, and substantially all of the remaining portions of the molecule (except, in some cases, small portions of the framework regions within the variable region) are human derived and correspond in amino acid sequence to a human antibody. In addition to chimeric antibodies, such humanised antibodies may be preferred for therapeutic applications according to the present invention.

The term 'immunisation' refers to the injection of a polypeptide with immunogenic properties. Depending on the host species various types of adjuvants can be used in order to increase the immunological response including but not limited to Freund's adjuvant, mineral gels such as aluminium hydroxide, and surface-active substances such as lysolecithin, pluronic polyols, polyanions, peptides, oil emulsions, keyhole limpet hemocyanin, and dinitrophenol.

An important aspect of the present invention pertains to an antibody or antiserum induced in response to one or more amino acid sequences selected from the group consisting of
  a) SEQ ID NO.: 2; and
  b) a sequence having at least 80% sequence identity to a); and
  c) a sub-sequence of a) or b) with a minimum length of 10 amino acids and/or one or more nucleic acid sequences nucleic acid sequence selected from the group consisting of
  a) SEQ ID NO.: 1; and
  b) a sequence having at least 80% sequence identity to a); and
  c) a sub-sequence of a) or b) with a minimum length of 30 nucleic acids A preferred embodiment of this aspect of the invention pertains to an antibody, which is capable of binding to a molecule expressed on the surface of an intact erythrocyte infected by a placental parasite.

Another preferred embodiment pertains to an antibody, which is capable of binding specifically to a molecule expressed on the surface of an intact erythrocyte infected by a placental parasite. In this context, the term 'specific binding' indicates that the antibody recognises a panel of placental parasites expressing VSA-PAM to a significantly higher level than a panel of non-placental parasites as determined by flow cytometry (Staalsoe, et al. 2001).

Additionally, preferred embodiments of this aspect of the invention pertains to antibodies or parts of antibodies which are capable of preventing or reducing the binding of erythrocytes to CSA. It is conceivable that antibodies generated in response to immunisation with one or more of the nucleic acid sequences or amino acid sequences of the present invention when present in a sufficiently high concentration will provide a hindrance of the VAR2CSA dependent adhesion to CSA. In particular, antibodies of the IgG class may be used for this purpose. Furthermore, based on the molecular structures of the variable regions of the antibodies according to the present invention, a skilled person will be able use molecular modelling and rational molecular design to generate and screen small molecules which mimic the molecular structures of the binding region of the antibodies and prevent or inhibit the adhesion of infected erythrocytes to CSA.

In some embodiments of the present invention, it is preferred to use shorter sequences of the polypeptide of the invention fused to a powerful immunogenic molecule such as keyhole limpet hemocyanin resulting in the production of antibodies against this chimeric molecule. Accordingly, antibodies capable of recognising VAR2CSA can be produced by injection of synthetic peptides consisting of 14 to 150 amino acids corresponding to a particular sequence of the VAR2CSA polypeptide. As an alternative, a more diverse set of antibodies can be generated by injection of a purified polypeptide embodiment of the invention.

As suggested above, monoclonal antibodies directed against a fragment of VAR2CSA, such as a purified polypeptide embodiment of the invention, can be produced using any of the conventional techniques that provide for the production of antibodies from cell lines in continuous culture. These techniques include the hybridoma technique, the human B-cell hybridoma technique, and the EBV-hybridoma technique.

It will be readily appreciated that polypeptides of the invention can be incorporated into vaccines capable of inducing protective immunity against a specific subtype of malaria. In relation to the present invention it is preferred that the vaccine is directed specifically against the infectious activity of *Plasmodium falciparum* in the placenta, which is characteristic of PAM.

One important aspect of the present invention therefore relates to a vaccine comprising one or more B-cell epitopes from a polypeptide encoded by a member of the var2 gene family as defined by Salanti et al. 2002. This vaccine is characterised in that it induces an IgG/antibody response wherein said IgG/antibody specifically recognises a molecule expressed on the surface of an intact erythrocyte infected by placental parasites or parasites that have been selected for their ability to mediate adhesion to CSA. Generally, this molecule is recognised by the antibodies in a gender-specific and parity-dependent manner.

In a preferred embodiment of the present invention, such a polypeptide-based vaccine comprises at least one amino acid sequence selected from the group consisting of
  a) SEQ ID NO.: 2; and
  b) a sequence having at least 70% sequence identity to a); and
  c) sub-sequences of a) or b) with a minimum length of 6 amino acids; and
  d) sub-sequences of a) or b) comprising at least one B-cell epitope.

Sub-sequences of the polypeptide of the invention used in a vaccine may be any of the above mentioned amino acid lenghts and in addition to these fragments or sub-sequences of the polypeptide of the invention, larger polypeptides comprising sub-sequences of the invention as part of their sequence, are also embodiments of the present invention. It is preferred, however, that these sub-sequences have a minimum length of 6 amino acids and that they are at least 70% identical to a region of comparable length within the sequence of SEQ ID NO.: 2. it is even more preferred that sub-sequences are at least 100 amino acids in length.

In recent years there has been increased focus on nucleotide based vaccines. Other aspects of the present invention therefore concern nucleotide based vaccines such as vaccines based on DNA molecules or on RNA molecules, which result in the expression of one or more B-cell epitopes from a polypeptide encoded by a member of the var2 gene family. As for the polypeptide based vaccine this vaccine is characterised in that it induces an IgG/antibody response wherein said IgG/antibody specifically recognises a molecule expressed on the surface of an intact erythrocyte infected by placental parasites or parasites that have been selected for their ability to mediate adhesion to CSA. It is further desired that this molecule is recognised by the antibodies in a gender-specific and parity-dependent manner.

One embodiment of the present invention relates to a nucleotide based vaccine, which results in the expression of an amino acid sequence comprising one or more B-cell epitopes from a polypeptide encoded by a member of the var2csa gene family, said vaccine characterised in that it is capable of inducing an IgG/antibody response wherein said IgG/antibody specifically recognises a molecule expressed on the surface of an intact erythrocyte infected by placenta parasites or parasites that have been CSA-selected in vitro, and wherein said molecule is recognised by antibodies in a gender-specific and parity dependent manner.

In a preferred embodiment, the present invention relates to a nucleotide-based vaccine, which may be a DNA or RNA vaccine, comprising a vector comprising at least one nucleotide sequence selected from the group consisting of a) SEQ ID NO.: 1 or a sequence complementary thereof; and
b) a nucleotide sequence having at least 70% sequence identity to a); and
c) sub-sequences of a) or b) with a minimum length of 18 nucleic acids; and
d) sub-sequences of a) and b) which comprise at least one sequence encoding a B-cell epitope.

The vaccine may thus comprise any of the sub-sequences of the nucleotide sequence of the invention, which may have any of the sequence identities described above. It is preferred, however, that these sub-sequences have a minimum length of 18 nucleic acids and that they are at least 70% identical to a region of comparable length within the sequence of SEQ ID NO.: 1. it is even more preferred that sub-sequences are at least 300 nucleotides in length.

According to this aspect of the invention one approach is to incorporate the DNA encoding a polypeptide of the invention or parts hereof into a viral or bacterial vector. The following organisms, among numerous others, may be employed for this purpose: Coxsackie virus, vaccinia virus, Salmonella typhi or Salmonella typhimurium (for oral administration). In each case the carrier organism must be acquired by the host cell and the relevant DNA sequences used for production of the polypeptide of the invention or parts hereof. These in turn are recognised as abnormal by the host or recipient and an immune response ensues.

Alternatively, the parasite nucleic acid sequence may be incorporated into an RNA virus or used to prepare viral replicons. This approach allows for the delivery of coding sequences, such as mRNA, to the host cell without risking a replicative, infectious process.

In order to obtain expression of immunogenic polypeptides it is required that elements of a nucleotide-based vaccine are capable of entering into the relevant target cells of the subject receiving such a vaccine. Therefore, it is preferred that the vaccine further comprise one or more agents and/or vectors to facilitate such entry.

It is further preferred that the vector component of a nucleotide-based vaccine comprises a promoter for driving the expression in a mammalian cell line, a nucleotide sequence encoding a leader peptide for facilitating secretion/release of a polypeptide sequence from a mammalian cell, and a terminator.

The simple concept of a nucleotide-based vaccine is the inoculation of a recipient using the relevant DNA sequence alone. This 'naked DNA' approach avoids the administration of polypeptide directly, but its effectiveness depends on the ability of the host cell to utilise the injected DNA as a template for RNA and subsequent protein synthesis.

It is anticipated that the principal value of providing PAM-specific protective immunity to sporozoite-induced infection will be for those individuals who have had previous exposure to malaria. In the case of PAM such individuals will be primigravid women who live in endemic areas. However, it is also anticipated that multi-gravid women who have not yet acquired immunity towards placental infections with *P. falciparum* and previously unexposed pregnant women travelling into endemic areas and women likely to become pregnant during such travelling will benefit from receiving said vaccine.

While not being limited by way of theory it is believed that the protection against malaria obtained by the use of a vaccine is most likely a result of IgGs blocking the interaction between the iRBC and cells in the placenta. It is also possible, however, that opsonized erythrocytes are killed by macrophages or T-cells, either by fagocytosis or by other means.

In a preferred embodiment, the vaccine is therefore capable of inducing an immunoglobulin response and, accordingly, it comprises a polypeptide comprising one or more B-cell epitopes. It is desirable, however, that polypeptides comprising one or more T-cell epitopes are also part of the vaccine since assistance from T-cells may be required in order to obtain a good antibody response.

In another preferred embodiment of the invention, the vaccine is therefore based on the use of polypeptides of the invention wherein said polypeptides comprises one or more B-cell epitopes in combination with one or more T-cell epitopes. In a less preferred embodiment of the invention, the vaccine comprises B-cell epitopes in combination with T-cell epitopes originating from an exogenous molecule, and in an even less preferred embodiment, the peptides of the vaccine comprises only B-cell epitopes. In equally preferred embodiments of the invention, the vaccine is based on nucleotide sequences encoding polypeptides, which have the characteristics with respect to antigen epitopes described above.

Techniques exist for enhancing the antigenicity of immunogenic peptides including incorporation of these into a multimeric structure, binding to a highly immunogenic protein carrier, for example, keyhole limpet hemocyanin, or diptheria toxoid, and administration in combination with adjuvants or any other enhancers of immune response. Furthermore, it will be understood that polypeptides specific for a plurality of *Plasmodium* stages and species may be incorporated in the same vaccine composition to provide a multivalent vaccine. In addition, the vaccine composition may comprise antigens to provide immunity against other diseases in addition to malaria.

Immunogenic polypeptides of the invention as well as nucleic acid molecules encoding such polypeptides may be injected as is, or for convenience of administration, it can be added to pharmaceutically acceptable carriers or diluents. Suitable pharmaceutically acceptable carriers will be apparent to those skilled in the art, and include water and other polar substances, including lower molecular weight alkanols, polyalkanols such as ethylene glycol, polyethylene glycol, and propylene glycol as well as non-polar carriers.

Routes of administration, antigen dose, number and frequency of injections are all matters of optimisation within the scope of ordinary skill in the art, particularly in view of the fact that there is already experience in the art of providing protective immunity by the injection of irradiated sporozoites. Protective antibodies are usually best elicited by a series of 2 to 3 doses given about 2 to 3 weeks apart. The series can be repeated when concentrations of circulating antibodies in the vaccinee drops. Further, the vaccine can be used to immunise a human against other forms of malaria, that is, heterologous immunisation. The polypeptide is present in the vaccine in an amount sufficient to induce an immune response against the antigenic polypeptide and thus to protect against *Plasmodium* infection thereby protecting the human against malaria.

Vaccination protocols can include the identification of a subject in need of a vaccine, for instance adolescent females and/or pregnant women living in regions populated with *P. falciparum* or pregnant women travelling through such regions, and administration of one or more effective doses of the vaccine to this subject.

Pharmaceuticals and Compositions

Another aspect of the present invention is the production of pharmaceuticals based on polypeptides of the invention or sub-sequences hereof or nucleic acid sequences encoding such molecules, as described above. Such pharmaceuticals may also include agents such as but not limited to other polypeptides and in particular antibodies, which are capable of modulating the adhesion of VAR2CSA to CSA.

Accordingly, it is within the scope of the invention to provide the use of at least one amino acid sequence selected from the group consisting of
   a) SEQ ID NO.: 2; and
   b) a sequence having at least 70% sequence identity to a); and
   c) sub-sequences of a) or b) with a minimum length of 6 amino acids; and
   d) sub-sequences of a) or b) comprising at least one B-cell epitope for the manufacture of a composition, such as an immunogenic composition, which is to be administered in order to prophylactically or therapeutically reduce the incidence, prevalence or severity of PAM in a female subject.

These sub-sequences may have a minimum length of 6 amino acids and that they are at least 70% identical to a region of comparable length within the sequence of SEQ ID NO.: 2. it is even more preferred that sub-sequences are at least 100 amino acids in length.

A preferred embodiment of this aspect of the invention pertains to the use of a polypeptide sequence selected from the group consisting of
   a) SEQ ID NO.: 2; and
   b) a sequence having at least 80% sequence identity to a); and
   c) a sub-sequence of a) or b) with a minimum length of 10 amino acids for the manufacture of a composition which is to be administered in order to prophylactically or therapeutically reduce the incidence, prevalence or severity of pregnancy-associated malaria in a female subject.

Also in this context it is further preferred that the amino acid sequence is capable of Inducing an immune response against a molecule expressed on the surface of an intact erythrocyte infected by a placental parasite. It is equally preferred that the amino acid sequence is capable of inducing an immune response against a molecule expressed on the surface of an intact erythrocyte infected by a parasite that has been selected for its ability to mediate adhesion to CSA.

In particularly preferred embodiments the sub-sequence comprises at least one B-cell epitope, and in other particularly preferred embodiments it comprises one or more GAG-binding motifs.

It is further preferred that the amino acid sequence does not comprise a CIDR domain or DBL-γ domain and that the amino acid sequence is gender specifically recognised. Finally, it is preferred that the amino acid sequence is recognised in a parity dependent manner. In addition, the invention also relates to the use of a nucleic acid molecule comprising at least one nucleotide sequence selected from the group consisting of
   a) SEQ ID NO.: 1 or a sequence complementary thereof; and
   b) a nucleotide sequence having at least 70% sequence identity to a); and
   c) sub-sequences of a) or b) with a minimum length of 18 nucleic acids; and
   d) sub-sequences of a) and b) which comprise at least one sequence encoding a B-cell epitope for the manufacture of a composition, such as an immunogenic composition, which is to be administered in order to prophylactically or therapeutically reduce the incidence, prevalence or severity of PAM in a female subject.

It is preferred that these sub-sequences have a minimum length of 18 nucleic acids and that they are at least 70% identical to a region of comparable length within the sequence of SEQ ID NO.: 1. it is even more preferred that sub-sequences are at least 300 nucleotides in length.

Another preferred embodiment pertains to the use of a nucleotide sequence selected from the group consisting of
   a) SEQ ID NO.: 1; and
   b) a sequence having at least 80% sequence identity to a); and
   c) a sub-sequence of a) or b) with a minimum length of 30 nucleic acids for the manufacture of an composition which is to be administered in order to prophylactically or therapeutically reduce the incidence, prevalence or severity of pregnancy-associated malaria in a female subject.

Especially preferred is a nucleic acid sequence which is capable of inducing an immune response against a molecule expressed on the surface of an intact erythrocyte infected by a placenta parasite.

In particularly preferred embodiments the sub-sequence encodes at least one B-cell epitope and/or at least one T-cell epitope, and in other particularly preferred embodiments it encodes one or more GAG-binding motifs.

It is further preferred that the nucleic acid sequence does not encode a sequence comprising a CIDR domain or DBL-γ domain and that the nucleic acid sequence encodes an amino acid sequence that is gender specifically recognised. Finally, it is preferred that nucleic acid sequence encodes an amino acid sequence which is recognised in a parity dependent manner.

Again the nucleic acid sequence may be a re-codonised sequence and may, in particular be recodonised in order to enhance expression in an expression system selected from the group of expression systems previously mentioned.

A currently most preferred embodiment of the invention pertains to use of the recodonised sequence of SEQ ID NO.: 3.

It should be understood that any feature and/or aspect discussed above in connection with the use of the nucleic acid sequences and amino acid sequences according to the invention apply by analogy to methods of treatment or prevention of PAM according to the invention.

Delivery of these pharmaceuticals can be performed by any conventional route including, but not limited to, transdermal, parenteral, gastrointestinal, transbronchial, and transalveolar administration.

In preferred embodiments, antibodies directed against the polypeptides of the invention can be administered to a subject in order to provide protection against the retention and sequestration of iRBC in the placenta which is characteristic of PAM. Effective amounts of an agent that will promote an immune response against a compound of the present invention can be administered to subjects living in endemic areas so as to prevent the contraction of malaria. In another embodiment, a subject believed to be at risk for contracting malaria may be identified either by conventional methods or by one of the in vitro diagnostic techniques, which constitute other embodiments of the present invention. An effective amount of an agent that inhibits VAR2CSA mediated sequestration or elicits an immune response in a subject can then be administered to this subject.

Biotechnological Tools

The use of the nucleic acid and polypeptide-based embodiments of the present invention can also extend to their use as biotechnological tools and as components of diagnostic assays.

Additional embodiments of the invention therefore include an in vitro diagnostic method, which comprises contacting a sample such as a tissue or biological fluid with a polypeptide comprising a sequence selected from the group consisting of
  a) SEQ ID NO.: 2; and
  b) a sequence having at least 70% sequence identity to a); and
  c) sub-sequences of a) or b) with a minimum length of 6 amino acids; and
  d) sub-sequences of a) or b) comprising at least one B-cell epitope under conditions allowing an in vitro immunological reaction to occur between said polypeptide composition and the antibodies possibly present in the biological sample, and the in vitro detection of the antigen-antibody complexes possibly formed. In one preferred embodiment the polypeptide is immobilised on a solid support.

Other embodiments include an in vitro diagnostic method, which comprises contacting a sample such as a tissue or biological fluid with a nucleotide composition comprising a sequence selected from the group consisting of
  a) SEQ ID NO.: 1 or a sequence complementary thereof; and
  b) a nucleotide sequence having at least 70% sequence identity to a); and
  c) sub-sequences of a) or b) with a minimum length of 18 nucleic acids; and
  d) sub-sequences of a) and b) which comprise at least one sequence encoding a B-cell epitope under conditions allowing an in vitro reaction to occur between said nucleotide composition and the antibodies possibly present in the biological sample, and the in vitro detection of the antigen-antibody complexes possibly formed.

In a preferred embodiment the in vitro diagnostic method comprises contacting a sample with a polypeptide sequence selected from the group consisting of
  a) SEQ ID NO.: 2; and
  b) a sequence having at least 80% sequence identity to a); and
  c) a sub-sequence of a) or b) with a minimum length of 10 amino acids, under conditions allowing an in vitro immunological reaction to occur between the said polypeptide and the antibodies possibly present in said sample, and the in vitro detection of the antigen-antibody complexes possibly formed.

Also for the in vitro diagnostic method it may be preferred that the amino acid used is a sequence is capable of inducing an immune response against a molecule expressed on the surface of an intact erythrocyte infected by a placental parasite. It is equally preferred that the amino acid sequence is capable of inducing an immune response against a molecule expressed on the surface of an intact erythrocyte infected by a parasite that has been selected for its ability to mediate adhesion to CSA.

In particularly preferred embodiments the sub-sequence comprises at least one B-cell and/or T-cell epitope, and in other particularly preferred embodiments it comprises one or more GAG-binding motifs.

It is further preferred that the amino acid sequence does not comprise a CIDR domain or DBL-γ domain and that the amino acid sequence is gender specifically recognised. Finally, it is preferred that the amino acid sequence is recognised in a parity dependent manner.

In another preferred embodiment the in vitro diagnostic method comprises contacting a sample with a nucleic acid sequence selected from the group consisting of
  a) SEQ ID NO.: 1; and
  b) a sequence having at least 80% sequence identity to a); and
  c) a sub-sequence of a) or b) with a minimum length of 30 nucleic acids, under conditions allowing an in vitro biochemical reaction to occur between the said nucleic acid sequence and nucleic acid sequences possibly present in said sample.

Especially preferred is a nucleic acid sequence which is capable of inducing an immune response against a molecule expressed on the surface of an intact erythrocyte infected by a placental parasite.

In particularly preferred embodiments the sub-sequence encodes at least one B-cell epitope and/or at least one T-cell epitope, and in other particularly preferred embodiments it encodes one or more GAG-binding motifs.

It is further preferred that the nucleic acid sequence does not encode a sequence comprising a CIDR domain or DBL-γ domain and that the nucleic acid sequence encodes an amino acid sequence that is gender specifically recognised. Finally, it is preferred that nucleic acid sequence encodes an amino acid sequence which is recognised in a parity dependent manner.

In some aspects, the nucleic acid embodiments are employed as nucleic acid probes in hybridisation assays, in cloning, or as primers for polymerase chain reaction (PCR). Similarly, the polypeptide-based embodiments can be used as components of immunological reactions such as ELISA, radio-immunoassays (RIA) and adhesion-blocking assays. The scope of such work can be, for example, to characterise VAR2CSA, or regions of VAR2CSA involved in interaction with CSA as well as other molecules including other VARCSA species that are involved in such interactions.

Diagnostic embodiments of the present invention provides methods and kits for the diagnosis of malaria and pregnancy associated malaria in particular. Malaria, hereunder pregnancy associated malaria can be diagnosed by detecting *P falciparum* derived compounds related to VAR2CSA in a bodily fluid. These VAR2CSA related compounds can for example be mRNA, DNA, protein-antigen, peptide-antigen or antibody being of any subclass. The methods for in vitro diagnosis of pregnancy associated malaria could be PCR, RT-PCR, ELISA, RIA, Dip stick test or any hybridisation assay as defined:

In some diagnostic embodiments, nucleic acids complementary to the nucleic acid molecules of the invention or fragments hereof are used to identify var2csa nucleic acids (e.g. mRNA) present in a biological sample, for instance a tissue sample or a sample of body fluid such as blood or serum. In a preferred diagnostic embodiment, nucleic acid molecules complementary to fragments of var2csa comprising sequences, which are not found in nucleic acids encoding other VARCSA proteins, are used to identify var2csa nucleic acids (e.g. mRNA) present in a biological sample.

The concentration or expression level in the infected subject of var2csa nucleic acids or other nucleic acids, which encode proteins that can mediate adhesion to CSA will differ depending on the type of *Plasmodium* infection. Thus, some *Plasmodium* parasites will only cause the expression of low amounts of VAR2CSA or no expression at all. Likewise it will not be possible to detect any expression of VAR2CSA in subjects that are not carrying a *Plasmodium* infection. Accordingly, malaria and, more specifically, PAM can be diagnosed by determining the concentration of var2csa gene transcripts in an individual at risk of contracting this disease. In the case of PAM such individuals may be e.g. pregnant women who live in endemic and sub-endemic areas, and previously unexposed pregnant women travelling into endemic areas.

One embodiment of the present invention is therefore an in vitro diagnostic method whereby infection with Plasmodium and more specifically infection with *P. falciparum* can be detected. In a preferred embodiment, a disease state profile can be created by collecting data on the expression level of var2csa in a large number of infected subjects and subsequent using these sets of data as reference. The concentration or expression level of var2csa transcripts detected in a tested subject can then be compared to this reference material so as to predict or follow the disease-state of that particular individual. Thus, in some embodiments the term "var2csa disease-state profile" refers to the concentration or expression level or concentration range or expression level range of a nucleic acid sequence encoding VAR2CSA or a part hereof that is detected in a biological sample. Arrays comprising nucleic acid probes comprised by the nucleotide sequence of the invention or fragments hereof can be used to create such disease-state profiles.

Accordingly, a particular embodiment of this aspect of the invention is an in vitro diagnostic procedure, wherein a disease-state profile for a tested subject is generated by determining the concentration or expression level in a sample of sequences as defined above.

In a similar fashion to that discussed above, a VAR2CSA disease-state profile comprising concentration levels or concentration range levels of VAR2CSA amino acid sequences in healthy and diseased subjects can be created and used to follow the disease-state of an individual. Accordingly, in some embodiments the term "VAR2CSA disease-state profile" refers to the concentration or concentration range or the expression level or expression level range of a polypeptide corresponding to VAR2CSA or a part hereof in a biological sample. Preferred methods for detecting such proteins or polypeptides include radioactive or non-radioactive immune-based approaches such as ELISA or radio-immunoassays as well as standard membrane-blotting techniques.

The invention also relates to a method for the in vitro detection of antibodies, which correlate with malaria originating from the infection of an individual *P. falciparum* in a tissue or biological fluid likely to contain such antibodies. This procedure comprises contacting a biological fluid or tissue sample as defined above with a preparation of antigens comprising the polypeptide of the invention or any part hereof under conditions, which allow an in vitro immunological reaction to occur between these antigens and the antibodies possibly present in the tissue or fluid. It further comprises the in vitro detection of the antigen-antibody complexes possibly formed by the use of conventional techniques. As an example, a preferred method involves the use of techniques such as ELISA, as well as immuno-fluorescent or radio-immunological assays (RIA) or equivalent procedures.

Again, such techniques can be used for collecting data on the concentration of antibodies against the polypeptide of the invention or parts hereof in subjects infected with *Plasmodium* parasites. These data can serve as reference when compared to the concentration of antibodies against the polypeptide of the invention detected in a given subject and a disease-state profile can be generated on the basis hereof. Thus, in some embodiments the term "VAR2CSA disease-state profile" refers to the concentration or concentration range of VAR2CSA antibodies, which are detected in a biological sample.

With respect to the above embodiments, the invention further relates to host cells comprising the above-described nucleic acid molecules. The nucleic acid molecules may be transformed, stably transfected or transiently transfected into the host cell or infected into the host cell by a live attenuated virus. The preferred host cells may include, but are not limited to, prokaryotic cells, such as *Escherichia coli, Staphylococcus aureus*, and eukaryotic cells, such as *Sacchromyces cerevisiae*, CHO and COS cells as well as Bachulo virus infected hi-fi insect cells. Transformation with the recombinant molecules can be effected using methods well known in the art.

In other aspects of the invention, kits are provided which will simplify the use of the polypeptide and nucleotide embodiments of the invention for in vitro diagnostic purposes. Such an in vitro diagnostic kit may comprise a sequence selected from the group consisting of a) SEQ ID NO.: 2; and b) a sequence having at least 70% sequence identity to a); and c) sub-sequences of a) or b) with a minimum length of 6 amino acids; and d) sub-sequences of a) or b) comprising at least one B-cell and/or T-cell epitope.

In addition to this component, the kit may comprise reagents for preparing a suitable medium for carrying out an immunological reaction between an IgG/antibody present in a sample of body fluid and said sequence; and reagents allowing the detection of the antigen-antibody complexes formed, wherein said reagents may bear a radioactive or non-radioactive label.

A specific embodiment pertains to an in vitro diagnostic kit comprising a) a nucleic acid sequence and/or an amino acid sequence as defined above for the in vitro diagnostic method b) reagents for preparing a suitable medium for carrying out an immunological reaction between an IgG/antibody present in a sample of body fluid or tissue and said sequence; and c) reagents allowing the detection of the antigen-antibody complexes formed, wherein said reagents may bear a radioactive or non-radioactive label.

It is further preferred that the in vitro diagnostic kit comprises a polypeptide sequence selected from the group consisting of a) SEQ ID NO.: 2; and b) a sequence having at least 80% sequence identity to a); and c) a sub-sequence of a) or b) with a minimum length of 10 amino acids, Again, it may be preferred that the amino acid used is a sequence is capable of inducing an immune response against a molecule expressed on the surface of an intact erythrocyte infected by a placental parasite. It is equally preferred that the amino acid sequence is capable of inducing an immune response against a molecule expressed on the surface of an intact erythrocyte infected by a placental parasite.

Additionally, it may be preferred that an in vitro diagnostic kit comprises a nucleic acid sequence selected from the group consisting of
   a) SEQ ID NO.: 1; and
   b) a sequence having at least 80% sequence identity to a); and
   c) a sub-sequence of a) or b) with a minimum length of 30 nucleic acids It may further be preferred that the nucleic acid sequence is a sequence which is capable of inducing an immune response against a molecule expressed on the surface of an intact erythrocyte infected by a placental parasite.

In particularly preferred embodiments the sub-sequence encodes at least one B-cell epitope and/or at least one T-cell epitope, and in other particularly preferred embodiments it encodes one or more GAG-binding motifs.

It is further preferred that the nucleic acid sequence does not encode a sequence comprising a CIDR domain or DBL-γ domain and that the nucleic acid sequence encodes an amino acid sequence that is gender specifically recognised. Finally, it is preferred that nucleic acid sequence encodes an amino acid sequence, which is recognised in a parity dependent manner.

Again the nucleic acid sequence may be a re-codonised sequence and may, in particular be recodonised in order to enhance expression in an expression system selected from the group of expression systems previously mentioned.

A currently most preferred embodiment of the invention pertains to use of the recodonised sequence of SEQ ID NO.: 3.

Alternatively, the in vitro diagnostic kit may comprise IgGs/antibodies or antibody fragments as described above, which specifically recognise a sequence selected from the group consisting of
   a) SEQ ID NO.: 2; and b) a sequence having at least 80% sequence identity to a); and
   c) sub-sequences of a) or b) with a minimum length of 20 amino acids; and
   d) sub-sequences of a) or b) comprising at least one B-cell epitope as well as reagents for preparing a suitable medium for carrying out an immunological reaction between said IgG/antibody and a sequence possibly present in a sample of body fluid or tissue and reagents allowing the detection of the antigen-antibody complexes formed. Said agents or said antibodies may optionally bear a radioactive or non-radioactive label.

In a preferred embodiment, the kit comprises a solid support to which the IgGs/antibodies of the kit are coupled. Such a support may for instance comprise an organic polymer.

In an additional embodiment, the kit comprises one or more doses of a vaccine in addition to the diagnostic components as described above. It is contemplated that such a kit may simplify the process of identifying and treating subjects in need of one of the therapeutic or prophylactic embodiments of the invention. Furthermore, the diagnostic components of a kit may be used to determine the presence of IgGs/antibodies and thereby the efficiency of the vaccine in each individual subject.

In certain embodiments a kit comprises preparations of the polypeptide and/or nucleotide embodiments of the invention filled in a number of separate containers. The containers can be entirely separate or can be constituted by separate chambers of the same applicator device. Where the containers are separate, they could be provided in the form of a kit comprising separate dispensers or syringes. Where the containers form part of the same applicator, they could for example, be defined by separate barrels of a multi-barrel syringe. A kit may thus comprise containers and/or barrels, where one container or barrel contains an immunogenic substance and another container or barrel contains a diluent and/or a carrier and/or an adjuvant. Other containers or barrels may contain diagnostic components.

Novel Agents

Within the scope of the present invention are also methods for identifying and/or designing novel agents useful in the prevention or treatment of malaria. Embodied in the invention is therefore a method for identifying an agent, which is capable of disrupting the *Plasmodium* life cycle, and an agent, which specifically modulates VAR2CSA dependent adhesion to CSA, the method comprising providing a cell expressing an amino acid sequence selected from the group consisting of
   a) SEQ ID NO.: 2; and
   b) a sequence having at least 80% sequence identity to a); and
   c) sub-sequences of a) or b) with a minimum length of 20 amino acids; and
   d) sub-sequences of a) or b) comprising at least one B-cell and/or T-cell epitope and contacting said cell with the agent and detecting adhesion of said cell to chondroitin sulphate A.

By this approach, an agent, which inhibits adhesion of a polypeptide of the invention to CSA can be identified by contacting CSA or a representative fragment thereof with polypeptides of the invention or sub-sequences thereof in the presence of the agent. Detection is accomplished and successful agents identified—according to their ability to induce a desired modulation of the formation of complexes of CSA and polypeptides of the invention.

In a preferred embodiment, this method is based on the detection of cells, which adhere to CSA immobilised on a solid support. Again, such a support may for instance comprise a resin, a membrane, an organic polymer, a lipid or a cell or part thereof. According to another aspect of the invention a support comprising a polypeptide of the invention or a fragment thereof coupled to it can be used to capture CSA or fragments of CSA and thereby identify substances that are capable of modulating the interaction of CSA and a polypeptide of the invention. The method may be based on directly or indirectly labelled CSA or a labelled polypeptide of the invention as well as the labelling of whole cells using radioactive as well as non-radioactive techniques. Another possibility of using the polypeptide embodiments of the present invention is the development of a method for identifying an agent, which interacts with an amino acid sequence selected from the group consisting of
   a) SEQ ID NO.: 2; and
   b) a sequence having at least 70% sequence identity to a); and
   c) sub-sequences of a) or b) with a minimum length of 6 amino acids; and
   d) sub-sequences of a) or b) comprising at least one B-cell epitope;

said method comprising providing a cell expressing one or more of said polypeptides; contacting said cell with the agent; and detecting the interaction of the agent with one or more of the said polypeptides.

A specific embodiment pertains to a method for testing whether a molecule inhibits binding of an amino acid sequence as disclosed above to a receptor expressed on syncytiotrophoblast cells comprising a) isolating and culturing syncytiotrophoblast cells,
b) contacting said syncytiotrophoblast cells with a potential inhibiting-molecule,
c) contacting said endothelial cells with RBC infected with parasites which express any of the amino acid sequences disclosed above on their surface,
d) measuring the binding of the iRBC with said syncytiotrophoblast cells.

The agents identified by the use of these methods may be monoclonal or polyclonal antibodies.

In addition, the methods described above can be used to identify compounds that will induce a desired immune response in a subject or patient and thereby serve as valuable tools in the development of novel pharmaceutical compositions as for instance vaccines. Therefore, in a preferred embodiment of the invention, the methods described above are used for identifying polypeptides, which will induce a specific IgG/antibody response upon administration to a subject in need hereof, or nucleotide sequences encoding such amino acid sequences. Use of the methods for this purpose comprises injecting into a living organism one or more of the polypeptides defined above, contacting a tissue or a biological fluid sample from said organism with said polypeptides; allowing an in vitro reaction to occur between the polypeptides and antibodies possibly present in the biological tissue; and the in vitro detection of complexes possibly formed.

An additional preferred embodiment is a method as described above wherein said tissue or said biological fluid sample is contacted with polypeptides expressed on the surface of a cell.

An equally preferred embodiment is a method as described above wherein said tissue or said biological fluid sample is contacted with polypeptides expressed on the surface of erythrocytes selected for adhesion to CSA.

Finally, another preferred embodiment of the invention is a method as described above wherein said tissue or biological fluid sample is contacted with polypeptides immobilised on a solid support.

In other embodiments, protein models of the polypeptides of the invention are constructed by the use of conventional techniques within molecular biology. Agents that interact with polypeptides of the invention are constructed and approaches in combinatorial chemistry are employed in the development of agents that modulate VAR2CSA mediated interaction with CSA or are able to induce an immune response. Accordingly, novel agents that interact with VAR2CSA are developed, screened in a VAR2CSA characterisation assay, for Instance a VAR2CSA anti-adhesion assay as described above. The identity of each agent and its performance in the VAR2CSA characterisation assay, its effect on the modulation of VAR2CSA-mediated adhesion to CSA or its ability to induce an immune response is recorded on electronic or non-electronic media. These recorded data can serve as the basis for a library of VAR2CSA modulating agents. Such a library can again be employed to further identify agents that modulate VAR2CSA-mediated adhesion to CSA and can be valuable tools for selecting an appropriate pharmaceutical to treat a particular type of Infection with *Plasmodium*. It is further expected that the high throughput screening techniques currently in use within the biotech and pharmaceutical industries can readily be applied to the procedures outlined above.

Finally, an additional aspect of the invention provides a method of generating a vaccine against malaria. A specific embodiment of this aspect the invention is a method for generating a vaccine against pregnancy associated malaria comprising a) injecting a nucleic acid sequence or an amino acid sequence according to the invention in a subject under conditions allowing said sequences to induce the generation of antibodies
b) purifying said antibodies
c) determining whether said antibodies display binding to any of the amino acid sequences according to the invention, when expressed on the surface of a iRBC infected with a parasite.

With respect to the above description of the various aspects of the present invention and of the specific embodiments of these aspects it should be understood that any feature and characterising described or mentioned above in connection with one aspect and/or one embodiment of an aspect of the invention also apply by analogy to any or all other aspects and/or embodiments of the invention described.

FIGURE LEGENDS

FIG. 1.

Quantitative fluorometric measurements (m1-4) of antibodies in plasma from non-pregnant Ghanaian adults (m1-5b) and Danish controls (m1-5a) that recognise the VSA expressed by a parasite (G4, see table 1-1) obtained from a male malaria patient (panel A) and the VSA of a parasite isolated from the placenta of a woman with PAM (Gb170) (panel B)

FIG. 2.

Quantitative measurements of antibodies in plasma from pregnant Ghanaian women (m1-5c) and Danish controls (m1-5a) that recognise VSA expressed by a parasite isolated from a man (Panel A) and from the placenta of a woman with PAM ($VSA_{PAM}$) (panel B)

FIG. 3.

Purification of late-stage parasite infected red blood cells by high gradient magnetic separation. Parasitemia in the starting material (in vitro culture of a primary isolate), (panel A) and the MACS-column eluate (panel B) is visualised by microscopy of Glemsa stained thin smears.

FIG. 4.

Labelling of uninfected (panel A) and trophozoite-/schizont-infected erythrocytes (panel B) by IgG in plasma from unexposed (black histogram) and parasite-exposed individuals (gray overlay). Uninfected and infected erythrocytes were identified by the absence or presence of EB fluorescence, respectively.

FIG. 5.

Distribution of maternal haemoglobin (hb) levels in blood from women without pathology signs of placental *P. falciparum* infection (panel A) and from women with evidence (parasitised erythrocytes and haemozoin-containing phagocytes) of active-chronic type placental infection (panel B). Bar graphs show actual distribution, while smooth curves show fitted normal distributions.

FIG. 6.

Hemoglobin levels (panel A) and birth weights (panel B) in women without pathology signs of placental *P. falciparum* infection ("No infection"), and in women with evidence (parasitised erythrocytes and haemozoin-containing phagocytes) of active-chronic type placental infection in the absence ("negative") or presence ("positive") of VSA(PAM)-specific IgG.

FIG. 7.

Absence of parity-dependent IgG recognition of VSA expressed by unselected *P. falciparum* isolate Busua (panel A), and presence of marked parity-dependent IgG recognition following selection of the Busua isolate for VSA-mediated adhesion to CSA (panel B).

FIG. 8.

Genotyping of *Plasmodium falciparum* isolates on polymorphic loci in msp1 (panels A-C), msp2 (panels D, E), and glurp (panel F) before and after selection (CSA suffix) for adhesion to CSA in vitro, demonstrating conservation of genotype following selection. Lanes 1, 16: MW markers; Lanes 2-3: Busua and Busua-CSA; Lanes 4, 5: 2O02 and 2O2-CSA; Lanes 6, 7: 2H3 and 2H3-CSA; Lanes 8, 9: FCR3 and FCR3-CSA; Lanes 10, 11: NF54 and NF54-CSA; Lane 12: Negative control (uninfected RBC); Lane 13: 3D7; Lane 14: Positive control (K1, IC1, glurp: 3D7; MAD20, FC27: Hb3; RO33: 7G8); Lane 15: double-negative control (Master mix only).

FIG. 9.

Changes in var gene transcription in ring-stage *P. falciparum* NF54 induced by selection for adhesion to chondroitin sulphate by repeated rounds of panning in vitro. Transcription levels were measured by real-time PCR using primers specific for each of 54 var genes and two pseudogenes identified in the *P. falciparum* 3D7 genome.

FIG. 10.

Domain structure of 59 annotated var genes and the var1 gene family truncated pseudo-gene PFE1640w in the 3D7/NF54 genome. PF0030c=NF54var2csa. Phylogenetic trees were constructed using the ClustalW program with the neighbour-joining method. Bootstrap values given for 1000 replications.

FIG. 11.

Phylogenetic tree of DBL domains. Domains of NF54var2csa (PFL0030c) are highlighted. Domains are named by their gene of origin and type a=α, b=β, c=γ, d=67. domain types. The vertical bar is set to cluster sequences in DBL domain types. The dominant DBL type is indicated for each cluster. *) As the DBL-δ types are as different from each other as they are to any other type, they all form independent clusters in this tree. Phylogenetic tree was constructed using the ClustalW program with the neighbour-joining method. Bootstrap values given for 1000 replications.

FIG. 12.

Phylogenetic tree of 2kb 5′ UTR. Sequences are named by their flanking var gene. Clustering by vertical line was set after visual inspection of alignment. Clusters are named A through I. Cluster A and H comprises sequences of the var1 and 5B1 types. Two sequences form in depended clusters; F) the UTR of the var1 homologue PFE1640w and G) PFL0030c (NF54var2csa). Phylogenetic tree was constructed using the ClustalW program with the neighbour-joining method. Bootstrap values given for 1000 replications.

FIG. 13.

Presence of var2csa homologues in genomic DNA from genotypically distinct *P. falciparum* isolates. Lane 1: MW marker (GeneRuler 50 bp DNA Ladder. Lanes 2-20: 19 different parasite isolates obtained from the peripheral blood of pediatric *P. falciparum* malaria patients Arrow indicates expected product size (160 kb) amplified with primer set #75 (Table 3), targeting var2csa DBL3-X.

FIG. 14.

Similarity of 2O2var2csa and 3d7var2csa. Alignment of DBL2-X (panel A) and DBL3-X (panel B). Identical residues appear on black background, conserved amino acid changes on grey, and radical changes on white background.

FIG. 15.

Similarity of var2csa homologues in genotypically distinct parasite isolates. Alignment of DBL3-X from three peripheral blood parasites from children and four placental parasites, covering amino acids 1211-1320 in 3d7var2csa (panel A). Alignment of DBL3-X in the same isolates covering amino acids 1473 to 1568 (panel B). Shading as in FIG. 4.

FIG. 16

Comparison of plasma IgG levels (Elisa OD) to recombinant proteins among men (1, n=31) and delivering women (2, n=27) from Ghana. The proteins were derived from GLURP (GLURP), CIDR VAR1 (p33), DBL6VAR2CSA (M106), DBL1VAR2CSA (A153), DBL5VAR2CSA (M101), DBL4VAR2CSA (M95). The VAR2CSA reactivity in female plasma was statistically significantly higher than in the men (P=0.035, P=0.008, P=0.002, and P=0.006 for DBL6, DBL1, DBL5, and DBL4, respectively). There was no difference between the male and female reactivity for GLURP and CIDR VAR1 (P=0.52 and P=0.39, respectively).

FIG. 17

Comparison of plasma IgG levels (Elisa OD) to recombinant proteins among Cameroonian women in their first pregnancy (1, n=40) and women, who had been pregnant one or several times before the current pregnancy (2, n=40) from Ghana. The proteins were derived from CIDRVAR1 (p33), DBL4VAR2CSA (M95) and DBL5VAR2CSA (M101), The VAR2CSA reactivity in multigravidae plasma was statistically significantly higher than in primigravidae plasma (P=0.003 and P=0.041, DBL4 and DBL5, respectively). There was no difference between the reactivity for CIDRVAR1 (P=0.56)

FIG. 18

Logistic regression data as described in Example 10, Table 8

FIG. 19

Western blot of 6 SDS extractions of different NF54 isolates (1-6) and 2 extractions of FCR (7,8). The blot was developed by an antibody raised in mice against *E. coli* DBL4VAR2CSA. The lanes indicated with an asterisk were loaded with extracts originating from parasites, which had been selected for CSA adhesion and recognised by antibodies in female plasma but not in plasma from men living in endemic areas (gender specific recognition). The remaining lanes were loaded with extracts from unselected parasites, which were recognised equally well by male and female plasma.

EXAMPLES

Example 1

Erythrocytes Infected by Placental *P. falciparum* Parasites Causing PAM are Serologically Distinct from Erythrocytes Infected by Other *P. falciparum* Parasites Pregnancy-associated malaria (PAM) appears to arise as a result of the capacity of *Plasmodium falciparum* to express parasite-encoded variant surface antigens (VSA) on the surface of infected erythrocytes (IE). These VSA can mediate IE adhesion to glycosaminoglycans in the placental intervillous space. The higher susceptibility to PAM in primigravidae compared to multigravidae in areas of intense *P. falciparum* transmission implies that protective immunity specific for PAM-associated antigens can be acquired. The only prominent functional difference between erythrocytes infected by placental parasites derived from women with PAM and erythrocytes infected by parasites from non-pregnant malaria patients is a marked difference in the adhesive properties of the VSA expressed. It is therefore likely that acquired, PAM-specific protective immunity in multigravidae in areas of intense parasite transmission is directed towards VSA that are devoid of cross-reactivity to VSA expressed in non-pregnant hosts and that mediate IE adhesion in the placenta.

Materials and methods m1-1. Isolation of IE from malaria patients: Circulating human erythrocytes infected with *Plasmodium falciparum* (IE) were collected in vacutainers containing either heparin or citrate-phosphate-dextrose (CPD) as anticoagulant. Plasma and white blood cells were removed upon centrifugation at 800 g, and the erythrocyte pellet resuspended in an equal volume of freezing solution (28%(v/v) glycerol in 4.2%(w/v) sorbitol and 0.9%(w/v) NaCl in $H_2O$) and snap-frozen in liquid Nitrogen. Parasites sequestering in term placentas of women with PAM were isolated by flushing the placenta with 25 IU/ml heparin in PBS. Erythrocytes were pelleted, resuspended and cryopreserved as described above for peripheral erythrocytes.

m1-2. In vitro culture of *P. falciparum* parasites: Cryopreserved IE were restored by thawing at 37° C. followed by washing in 3.5% NaCl2 and washing twice in RPMI 1640 culture medium (www.lifetech.com). Parasites were maintained in a 5% suspension culture of uninfected human O+ erythrocytes in RPMI 1640, supplemented with Albumax, hypoxanthin, glutamine, gentamycin (all www.lifetech.com), and non-immune human serum. Culture medium was changed and Giemsa-stained smears were prepared for microscopy on a daily basis.

m1-3. Purification of IE from cultures: IE with haemozoin-containing trophozoites and schizonts were purified from in vitro cultures (m1 2) by magnet-activated cell sorting (MACS; www.miltenyibiotec.com), exploiting the magnetic properties of haemozoin. In short, IE were passed through a size-C MACS column mounted with a 0.9 mm×40 mm needle. The column was washed with phosphate buffered saline (PBS) supplemented with 2% foetal calf serum (FCS; PBS-S) until no erythrocytes could be seen in the eluate. The column was removed from the magnet, and the trophozoite- and schizont-containing IE retained in the column were then released by further washing. A purity of trophozoite-/schizont-infected IE>90% was usually reached by this procedure (FIG. 3).

m1-4. Detection of human VSA-specific IgG: Purified IE (m1 3) were labelled with 1 μl ethidium bromide (EB; www.sigma-aldrich.com) solution (0.1 mg/ml) per $10^5$ erythrocytes to allow discrimination between nucleic acid-containing IE and uninfected erythrocytes devoid of DNA/RNA. For each sample, $2×10^5$ erythrocytes in 100 μl PBS-S (m1 3) were used. EB-labelled IE were mixed with 1-5 μl of human plasma or antibody preparation, followed by goat anti-human IgG (www.dako.com), diluted 1:200 and by fluorescein isothiocyanate (FITC)-conjugated rabbit anti-goat Ig (www.dako.com), diluted 1:25. The antibodies were diluted in PBS-S, and 100 μl of the dilution was added per sample. At each step, samples were incubated for 30 min at 5 μC. The samples were washed twice in 3 ml PBS-S between each incubation step and once after the last. Samples were kept overnight at 5° C. before analysis on a Coulter EPICS XL-MCL flow cytometer (beckman.com). For quantification of FITC fluorescence, the mean fluorescence intensity (MFI) of the ethidium bromide positive red blood cells was calculated using WinList software (www.vsh.com). Plasma from Danish donors never exposed to *falciparum* malaria did not label uninfected erythrocytes or IE above the level of the secondary and tertiary antibodies alone. In contrast, the plasma pool prepared from hyper-immune Ghanaians selectively labelled IE but not uninfected erythrocytes (FIG. 4).

m1-5. Human plasma samples tested: The individual human plasma samples were obtained from the following groups of individuals:

a. Plasma from Danish adults without exposure to *P. falciparum* parasites were obtained at the Copenhagen University Hospital (Rigshospitalet) from laboratory staff, blood donors and pregnant women being screened for the presence of anti-RhD b. Non-pregnant adults (28 males and 30 females) residing in a malarious area (Gomoa Onyadze village, Southern Ghana)

c. Third-trimester pregnant women residing in a malarious area (Prampram, Southern Ghana).

d. Women giving birth at hospitals in Ebolowa, Cameroon.

e. Women giving birth at Kilifi District Hospital, Kenya.

TABLE 1

Overview of serological testing of parasite isolates obtained from non-pregnant malaria patients and from placentas of women with PAM.

| Isolate | Host pregnant | Origin | Gender-specific IgG recognition[1] | Parity-dependency $A^2$ | $B^3$ | $C^4$ |
|---|---|---|---|---|---|---|
| G4 | NO | Peripheral, | No | No | — | — |
| G12 |  | Sudan | No | — | — | — |
| 2H3 |  | Peripheral, | No | No | No | — |
| 2O2 |  | Sudan | No | No | — | — |
| E2015 |  | Peripheral, | No | — | No | — |
| E2037 |  | Ghana | No | No | — | — |
| E2039 |  |  | No | No | — | — |
| E2045 |  |  | No | — | No | — |
| E2064 |  |  | No | — | No | — |
| Busua |  |  | No | — | — | No |
| Gb170 | YES | Placental, | Yes | Yes | Yes | — |
| Gb172 |  | Gabon | Yes | Yes | — | — |
| Gb337 |  |  | Yes | Yes | Yes | — |
| EJ10 |  | Placental, | Yes | — | — | — |
| EJ17 |  | Ghana | Yes | Yes | — | — |
| EJ24 |  |  | Yes | — | — | Yes |

—: not done.
Yes in gender-specificity means that Ghanaian women but not Ghanaian men have higher levels of VSA antibodies than the Danish controls.
Yes in parity-dependency means that there is a statistically significant association between parity and VSA antibody level that is independent on the age of the woman.
Superscripted numbers refer to plasma sets used (see Table footnotes).
[1]Plasma set m1-5b.
[2]Plasma set m1-5c.
[3]Plasma set m1-5d.
[4]Plasma set m1-5e Gender-specific IgG Recognition of VSA Associated with PAM To determine whether the distinct adhesive phenotype of erythrocytes infected by placental parasites was mirrored by a distinct serological phenotype, IE was collected from non-pregnant malaria patients and from placentas of women with PAM [m1-1 and Table 1]. These parasites were adapted to in vitro culture (m1-2), and used within 4 weeks from thawing of the original isolates to determine plasma levels of IgG specific for the VSA expressed by each isolate by a fluorometric assay (m1-3, m1-4). VSA-specific IgG levels were first determined in a panel of plasma samples from Ghanaian non-pregnant adults (m1-5b). As seen in FIG. 1 and Table 1 the majority of both male and female adults have high levels of IgG specifically recognising the VSA expressed by parasites from non-pregnant individuals. In marked contrast, only few adults who were all women had levels of IgG specific for VSA expressed by placental isolates above background (nonmalaria exposed Danish controls) (m1-5a). This gender-specific IgG recognition pattern indicates that placental parasites VSA are completely distinct from VSA expressed by parasites Infecting non-pregnant individuals.

Parity-dependent IgG Recognition of VSA Associated with PAM

To further explore whether women acquire the above-mentioned "gender-specific" IgG as a result of exposure to placental parasites, the levels of VSA-specific IgG were measured in plasma samples from pregnant women in Ghana (m1-5c), Cameroon (m1-5d) and Kenya (m1-5e). In all cases, VSA expressed by placental parasite isolates ($VSA_{PAM}$) were recognised in a parity-dependent manner. Thus, levels of $VSA_{PAM}$-specific IgG in plasma increased with increasing number of pregnancies, independently of the age of the pregnant women (Table 1 and FIG. 2, right). In marked contrast, VSA expressed by parasite isolates from non-pregnant individuals were equally well recognised by women of all parities (Table 1 and FIG. 2, left). The parity dependency of specific IgG plasma levels thus further distinguishes $VSA_{PAM}$ from VSA expressed by other parasites. Furthermore, this feature makes $VSA_{PAM}$ the most likely target of PAM-specific protective immunity acquired by multigravidae in endemic areas.

Example 2

IgG Specific for Parasite-encoded Variant Antigens on the Surface of Erythrocytes Infected by Placental and CSA-adhering *P. falciparum* Parasites Mediates Protection Against the Maternal Anaemia and Low Birth Weight Caused by Placental Malaria Infection The major clinical consequences of PAM are severe maternal anaemia predisposing to perinatal maternal death and low birth weight (LBW) due to intrauterine growth retardation and premature birth.

To further substantiate the hypothesis that immunological protection against PAM is mediated by antibodies recognising a distinct type of VSA ($VSA_{PAM}$) selectively expressed by placental parasites, the levels of IgG specific for VSA expressed in one placental parasite isolate (EJ24, Table 1) and one isolate from a male patient (Busua, Table 1) were measured in plasma samples from Kenyan women well-characterised with regard to PAM. The plasma samples were drawn from a larger previously described study cohort (Shulman et al., 2001). All the women who donated plasma samples had detailed histological examination of their placentas at delivery and were classified as being either 1. Not Infected (IE absent, and no deposition of parasite pigment), 2. Recently infected (IE present, but no deposition of pigment), 3. Chronically infected (IE and pigment present), or 4. Resolved infection (IE absent, pigment present). Women carrying chronic infections at delivery were both more likely to deliver LBW babies (<2.5 kg) and to be anaemic (haemoglobin (Hb)<8 g/dl) than women who were not infected. In contrast, women who were either recently infected or had resolved a previous infection did not differ significantly from the uninfected group in these respects.

Maternal Hb levels in women with uninfected placentas closely followed the expected normal distribution with a peak around 10 g/dl (FIG. 5, left). The Hb distribution among women with chronic placental infections resembled that of uninfected women except for the apparent superposition of a small group of women where Hb levels were much lower, peaking around 6 g/dl (FIG. 5, right). A similar pattern was observed with respect to the distributions of birth weight in these two groups.

The transmission of *falciparum* malaria in this area of Kenya is relatively low and seasonal. This means that many women can go through an entire pregnancy without being infected, explaining why PAM also occurs quite frequently in multigravidae in this cohort.

Plasma levels of IgG specific for VSA of one placental isolate and one non-PAM isolate in plasma from 94 women with chronic placental infection were measured using the procedures described in Example 1. Of these 94 women, 32 had no measurable IgG specific for the $VSA_{PAM}$ expressed by the placental parasite. The mean haemoglobin level of these women was 7.5 g/dl compared to 9.4 g/dl for uninfected women (P<0.001, t-test) (FIG. 6, left). Fifty of the 94 women had significant $VSA_{PAM}$-specific IgG levels (levels higher than in a 16-fold dilution of a highly reactive plasma pool prepared from multigravid Ghanaian women). The mean level of haemoglobin in this group was 9.2 g/dl, not significantly different from the mean level in uninfected women (9.4 g/dl) (FIG. 6, left). With respect to birth weight, the 32 chronically infected women without $VSA_{PAM}$-specific IgG delivered children that were significantly smaller than those of uninfected women (mean birth weight: 2.4 kg versus 2.9 kg in control group, P<0.001) (FIG. 6, right). The mean birth weight of babies born to mothers with significant $VSA_{PAM}$-specific IgG was 2.9 kg as for the uninfected women (FIG. 6, right). These protective effects of $VSA_{PAM}$-specific IgG were similar in primi- and multi-gravidae, strongly indicating that the protection against low Hb and LBW in multigravidae is a direct result of their higher levels of $VSA_{PAM}$-specific antibodies. The effect was specific for $VSA_{PAM}$, as presence or absence of IgG with specificity for PAM-unrelated VSA (expressed by the isolate from a male patient) was unrelated to Hb or birth weight. These data directly point to $VSA_{PAM}$-specific IgG as the mediators of acquired protection against PAM-related anaemia and LBW.

Example 3

Erythrocytes Infected by *P. falciparum* Parasites Selected for Adhesion to Chondroitin Sulphate A (CSA) in Vitro are Serologically Distinct from Erythrocytes Infected by Isogenic *P. falciparum* Parasites not Adhering to CSA As described in Example 1 and Example 2, placental parasites express a unique type of VSA ($VSA_{PAM}$). Thus, only *P. falciparum*-exposed women (who either are, or recently have been, pregnant) possess $VSA_{PAM}$-specific plasma IgG, while such antibodies are uniformly absent from sympatric males. Pregnant women with PAM in the absence of $VSA_{PAM}$-specific IgG are more likely to be anaemic and to deliver LBW babies than uninfected pregnant women or pregnant women with significant plasma levels of $VSA_{PAM}$-specific IgG. For these reasons, VSA expressed by placental parasites ($VSA_{PAM}$) is an attractive candidate for the development of a vaccine protecting against the clinical consequences of PAM, and molecular identification of such VSA thus becomes a priority.

*Plasmodium falciparum* undergoes sexual reproduction with zygote formation, genetic interchange and melosis during its transmission through Anopheline mosquitoes. Thus, even parasites isolated from individuals in the same village within short time frames are genetically diverse. This is compounded by the fact that the var genes encoding the best characterised VSA family PfEMP1 genes are among the genes showing the largest degree of inter-genomic variation. This variability makes it difficult to reliably compare the level of gene transcription and expression in parasites isolated from different individuals.

Several independent studies have shown that *P. falciparum* parasites isolated from non-pregnant individuals commonly express VSA that can mediate IE adhesion to receptors such as CD36, whereas chondroitin sulphate A (CSA)-adhering IE are rarely found in such Individuals. In contrast, placental IE generally adhere strongly to CSA but not to CD36 or other host receptors exploited by IE in non-pregnant hosts. Each haploid parasite genome contains approximately 60 different var genes, and clonal switching between different var genes results in changes in the VSA (PfEMP1) being expressed and in the adhesive phenotype of IE.

Panning on CSA followed by propagation of CSA-adhering parasites (m3-1) was used to select and expand parasites that had acquired a CSA-adhering phenotype as a result of clonal var gene switching.

A total of 10 CSA-selected sub-lines were derived from seven parasite lines isolated from non-pregnant individuals and from three long-term adapted parasite lines (NF54, FCR3 and Hb3). After 3 to 8 rounds of panning on CSA, 5 of the sub-lines expressed a VSA that was recognised in the same gender-specific and parity dependent manner as that of placental isolates (Table 2 and FIG. 7). According to PCR-based genetic analysis in three polymorphic loci, the CSA selected sub-lines that were expressing gender-specific VSA were genetically indistinguishable from their parental lines expressing VSA that was non-gender-specific (FIG. 8). With such pairs of isogenic parasite lines expressing gender-specific and non-gender-specific VSA it becomes possible to compare gene expression both at RNA and protein level in parasite lines that do and do not express the gender-specific VSA of placental parasites, respectively, without having to account for genetic differences between two parasite isolates.

Induction of gender-specific VSA expression by CSA-selection of NF54 is of particular interest as this parasite line was derived from the same primary isolate and has been genetically identical in all loci investigated so far to the cloned 3D7 parasite line used for the malaria genome project.

TABLE 2

Serological phenotype of 7 parasites isolated from non-pregnant malaria patients (see Table 1) and 3 long-term laboratory lines (FCR3, Hb3, NF54) after a minimum of 3 rounds of panning on CSA in vitro.

| Isolate | Gender specific IgG recognition[1] | Parity dependency | | |
|---|---|---|---|---|
| | | A[2] | B[3] | C[3] |
| G4-CSA | No | No | n.d. | n.d. |
| G12-CSA | No | No | n.d. | n.d. |
| 2H3-CSA | Yes | Yes | Yes | n.d. |
| 2O2-CSA | Yes | Yes | n.d. | n.d. |
| E2037-CSA | No | No | n.d. | n.d. |
| E2039-CSA | No | No | n.d. | n.d. |
| Busua-CSA | Yes | n.d. | n.d. | Yes |
| FCR3-CSA | Yes | Yes | Yes | Yes |
| Hb3-CSA | No | n.d. | n.d. | n.d. |
| NF54-CSA | Yes | Yes | n.d. | n.d. | n.d.: not done.
Yes in Gender specificity means that Ghanaian women but not Ghanaian men have higher plasma levels of VSA-specific IgG than unexposed Danish controls.
Yes in Parity-dependency means that there is a statistically significant association between parity and VSA-specific IgG levels that is independent of age.
[1]Plasma set ml-5b.
[2]Plasma set ml-5c.
[3]Plasma set ml-5d.
[4]Plasma set ml-5e.

Example 4

Selection of *P. falciparum* isolate NF54 for Adhesion to CSA in Vitro Results in Selective Up-Regulation of a Single Var Gene (NF54var2csa)

Parasite-encoded PfEMP1 proteins expressed on the surface membrane of IE mediate the adhesion of such erythrocytes to a range of host receptors. The PfEMP1 proteins are encoded by the var gene family containing 50-60 members per haploid parasite genome. Different PfEMP1 molecules have different receptor specificities, and clonal switching between expression of the various var gene products in a mutually exclusive manner allows the parasite to modify its adhesion properties. Gene expression and switching can be examined using gene-specific primers and real-time PCR. To compare var gene expression in the parasite line NF54 before (NF54) and after (NF54 CSA) selection for adhesion to CSA (Example 3), RNA was purified from NF54 and NF54 CSA and used for the synthesis of cDNA. Total RNA was prepared with Trizol LS (www.invitrogen.com) as recommended by the manufacturer, and treated with DNAseI (www.invitrogen.com) until free of DNA (the absence of DNA in the samples was confirmed by 40 cycles of real-time PCR with actin primers [Table 3] with no change in base fluorescence). One µg of DNA-free RNA was then reverse transcribed using 120 units of Superscript II reverse transcriptase and primed with 150 ng of random hexamer primers (www.invitrogen.com). Reverse transcriptase PCR was performed at 42° C. for 50 min in a total volume of 60 µl.

TABLE 3

Primer sets used in real-time PCR assays to specifically amplify 54 var genes and two pseudogenes (underlined). Where several genes are listed next to a single primer set, primer targets in the listed genes were identical

| Primer set | Forward primer | Reverse primer | Target gene(s) |
|---|---|---|---|
| 1 | TGCGCTGATAACTCACAACA | AGGGGTTCATCGTCATCTTC | PFA0005w |
| 3 | AACCCCAATACCATTACGA | TTCCCCACTCATGTAACCAA | PFA0765c |

TABLE 3-continued

Primer sets used in real-time PCR assays to specifically amplify 54 var genes and two pseudogenes (underlined). Where several genes are listed next to a single primer set, primer targets in the listed genes were identical

| Primer set | Forward primer | Reverse primer | Target gene(s) |
|---|---|---|---|
| 4 | GACGAGGAGTCGGAAAAGAC | TGGACAGGCTTGTTTGAGAG | PF10_0001 |
| 5 | GTGCACCAAAAGAAGCTCAA | ACAAAACTCCTCTGCCCATT | PF10_0406 |
| 6 | GAGGCTTATGGGAAACCAGA | AGGCAGTCTTTGGCATCTTT | PF11_0007 |
| 7 | GACGGCTACCACAGAGACAA | CGTCATCATCGTCTTCGTTT | PF11_0008 |
| 8 | TGCTGAAGACCAAATTGAGC | TTGTTGTGGTGGTTGTTGTG | PF11_0521 |
| 9 | TCGATTATGTGCCGCAGTAT | TTCCCGTACAATCGTATCCA | PFL0020w |
| 10 | TGGTGATGGTACTGCTGGAT | TTTATTTTCGGCAGCATTTG | PFL0030c |
| 11 | GACGCCTGCACTCTCAAATA | TTGGAGAGCACCACCATTTA | PFL0935c |
| 12 | AGCAAAATCCGAAGCAGAAT | CCCACAGATCTTTTCCTCGT | PFL1950w |
| 13 | AAAGCCACTAGCGAGGGTAA | TGTTTTTGCCCACTCCTGTA | PFL1955w/ PFL1970w |
| 15 | CATCCATTACGCAGGATACG | AAATAGGGTGGGCGTAACAC | PFL1960w |
| 17 | GGCACGAAGTTTTGCAGATA | TTTGTGCGTCTTTCTTCGTC | PFL2665c |
| 18 | CGGAGGAGGAAAAACAAGAG | TGCCGTATTTGAGACCACAT | PFL0005w |
| 19 | CGGAATTAGTTGCCTTCACA | CATTGGCCACCAAGTGTATC | PF13_0364 |
| 20 | CACAGGTATGGGAAGCAATG | CCATACAGCCGTGACTGTTC | PF13_0003 |
| 21 | CAATTTTGGGTGTGGAATCA | CACTGGCCACCAAGTGTATC | PFB1055c |
| 22 | ATGTGCGCTACAAGAAGCTG | TTGATCTCCCCATTCAGTCA | PFB0010w |
| 23 | CAATCTGCGGCAATAGAGAC | CCACTGTTGAGGGGTTTTCT | PFC1120c/ PFC0005w |
| 25 | ATATGGGAAGGGATGCTCTG | TGAACCATCGAAGGAATTGA | PFD0020c |
| 26 | ACCGCCCCATCTAGTGATAG | CACTTGGTGATGTGGTGTCA | PFD0615c |
| 27 | TAAAAGACGCCAACAGATGC | TCATCGTCTTCGTCTTCGTC | PFD0625c |
| 28 | ACTTTCTGGTGGGAATCAG | TTCACCGCCACTTACTTCAG | PFD0630c/ PFD0635c |
| 30 | GACGACGATGAAGACGAAGA | AGATCTCCGCATTTCCAATC | PFD0005w |
| 31 | AGAGGGTTATGGGAATGCAG | GCATTCTTTGGCAATTCCTT | PFD0995c/ PFD1000c |
| 34 | TGCAACGAAACATTAGCACA | AGCAGGGGATGATGCTTTAC | PFD1015c |
| 35 | AAACACGTTGAATGGCGATA | GACGCCGAGGAGGTAAATAG | PFD1235w/ MAL7P1.1 |
| 36 | TGACGACTCCTCAGACGAAG | CTCCACTGACGGATCTGTTG | PFD1245c |
| 37 | AAGAAAGTGCCACAACATGC | GTTCGTACGCCTGTCGTTTA | PFE1640w |
| 38 | GAAGCTGGTGGTACTGACGA | TATTTTCCCACCAGGAGGAG | PFE0005w |
| 39 | ATTTGTCGCACATGAAGGAA | AACTTCGTGCCAATGCTGTA | MAL6P1.252 |
| 40 | TTTGGGATGACACCAAGAAA | GTCGCTTGATGAAGGAGTCA | PF08_0140 |
| 41 | GGTGTCAAGGCAGCTAATGA | TATGTCCTGCGCTATTTTGC | PF08_0141 |
| 43 | GTCGTGGAAAAACGAAAGGT | TATCTATCCAGGGCCCAAAG | PF08_0142 |

TABLE 3-continued

Primer sets used in real-time PCR assays to specifically amplify 54 var genes and two pseudogenes (underlined). Where several genes are listed next to a single primer set, primer targets in the listed genes were identical

| Primer set | Forward primer | Reverse primer | Target gene(s) |
|---|---|---|---|
| 44 | ATGTGTGCGAGAAGGTGAAG | TGCCTTCTAGGTGGCATACA | MAL6P1.4 |
| 45 | CAATTTTTCCGACGCTTGTA | CACATATAGCGCCGTCCTTA | PF07_0048 |
| 46 | GCGACGCTCAAAAACATTTA | TCATCCAACGCAATCTTTGT | PF07_0050 |
| 47 | ACCAAATGGTGACTTGCTCA | TTTTCATCGACGGATGATGT | MAL7P1.50 |
| 49 | GTTGAGTCTGCGGCAATAGA | CTGGGGTTTGTTCAACACTG | PF07_0049 |
| 50 | CACACATGTCCACCACAAGA | ACCCTTCTGTGGTGTCTTCC | MAL7P1.56 |
| 51 | ACGTGGTGGAGACGTAAACA | CCTTTGTTGTTGCCACTTTG | MAL7P1.55 |
| 52 | CGTGGTAGTGAAGCACCATC | CCCACCTTCTTGTGGTTTCT | PF07_0051 |
| 53 | TGACGACGATAAATGGGAAA | TTCTTTTGGAGCAGGGAGTT | PF07_0139 |
| 54 | ACCAAGTGGTGACAAAGCAG | GGGTGGCACACAAACACTAC | PFD1005c/ PFD1015c |
| 55 | TTTGTCCGGAAGACGATACA | ATCTGGGGCAGAATTACCAC | PF08_0106 |
| 56 | TGCAAACCACCAGAAGAAAG | GTTCTCCGTGTTGTCCTCCT | PFI0005w |
| 57 | CGTAAAACATGGTGGGATGA | GGCCCATTCAGTTAACCATC | PFA0015C/ PFI1820W/ MAL6 P1.314 |
| 58 | CACACGTGGACCTCAAGAAC | AAAACCGATGCCAATACTCC | PF11830c |
| 64* | ACGATTGGTGGGAAACAAAT | CCCCATTCTTTTATCCATCG | PFL0030c |
| 65* | AAAGGAATTGAGGGGGAAAT | TAAACCACGAAACGGACTGA | PFL0030c |
| 73* | CCAAAATATAGCGAGCACA | CCTTCATCTTGCTCTTGTCG | PFL0030c |
| 74* | AAAGGAACCGGATGCTAATG | TGCTTCATTTCCGATGTTTG | PFL0030c |
| 75* | TAGTGAACCTATTTATATTCGT | CACCATTTGTATGTCCATGT | PFL0030c |
| 60** | AAGTAGCAGGTCATCGTGGTT | TTCGGCACATTCTTCCATAA | PF07_0073 |
| 61** | TGTACCACCAGCCTTACCAG | TTCCTTGCCATGTGTTCAAT | PF14_0425 |
| 100** | AGCAGCAGGAATCCACACA | TGATGGTGCAAGGGTTGTAA | PFL2215w |

*Primers specific for PFL0030c, but downstream to primer set #10
**Endogenous control genes: seryl-tRNA synthetase (PF07_0073), fructose-biphosphate aldolase (PF14_0425), actin (PFL2215w). To study gene expression of individual var genes a specific primer set for each of 54 var genes and two pseudogenes in the NF54 genome was made [Table 3], and real-time PCR was performed on cDNA from NF54 and NF54-CSA. Real-time PCR was done using a Rotorgene thermal cycler system (www.corbettresearch.com).

TABLE 4

Change in NF54var2csa gene transcription after selection for CSA-specific adhesion by in vitro panning. Specific primers targeting different var2csa regions (FIG. 1, Table 2) were used to measure transcription before (NF54) and after CSA selection (NF54-CSA). The fold change in transcription levels, normalised against seryl-tRNA synthetase, was calculated for each primer set by the ΔΔCt method (User Bulletin #2, Applied Biosystems, www.appliedbiosystems.com). Two other endogenous control genes, fructose-biphosphate aldolase and actin were included to confirm seryl-tRNA synthetase as a valid gene for data normalisation.

| Gene | Nucleotide | Domain | Primer set | $Ct_{NF54}$ | $Ct_{NF54-CSA}$ | $\Delta Ct_{NF54}$ | $\Delta Ct_{NF54-CSA}$ | $\Delta\Delta Ct$ | Change (x) |
|---|---|---|---|---|---|---|---|---|---|
| var2csa | 2451 | DBL2-X | 10 | 22.58 | 15.18 | 2.58 | -3.82 | -6.4 | 84.45 |
| var2csa | 4200 | DBL3-X | 65 | 23.66 | 16.77 | 3.66 | -2.23 | -5.89 | 59.30 |
| var2csa | 4570 | DBL3-X | 75 | 26.25 | 18.95 | 6.25 | -0.05 | -6.3 | 78.79 |

TABLE 4-continued

Change in NF54var2csa gene transcription after selection for CSA-specific adhesion by in vitro panning. Specific primers targeting different var2csa regions (FIG. 1, Table 2) were used to measure transcription before (NF54) and after CSA selection (NF54-CSA). The fold change in transcription levels, normalised against seryl-tRNA synthetase, was calculated for each primer set by the ΔΔCt method (User Bulletin #2, Applied Biosystems, www.appliedbiosystems.com). Two other endogenous control genes, fructose-biphosphate aldolase and actin were included to confirm seryl-tRNA synthetase as a valid gene for data normalisation.

| Gene | Nucleotide | Domain | Primer set | $Ct_{NF54}$ | $Ct_{NF54\text{-}CSA}$ | $\Delta Ct_{NF54}$ | $\Delta Ct_{NF54\text{-}CSA}$ | $\Delta\Delta Ct$ | Change (x) |
|---|---|---|---|---|---|---|---|---|---|
| var2csa | 5880 | DBL4-ε | 73 | 24.68 | 17.02 | 4.68 | −1.98 | −6.66 | 101.13 |
| var2csa | 6510 | DBL5-ε | 64 | 22.34 | 14.82 | 2.34 | −4.18 | −6.52 | 91.77 |
| var2csa | 6777 | DBL6-ε | 74 | 22.43 | 15.51 | 2.43 | −3.49 | −5.92 | 60.55 |
| Seryl-tRNA synthetase | — | — | 60 | 20.05 | 19.05 | 0 | 0 | 0 | 1 |
| Fructose-biphosphate aldolase | — | — | 61 | 17.75 | 16.74 | −2.25 | −2.26 | −0.01 | 1.01 |
| Actin | — | — | 100 | 18.97 | 17.57 | −1.03 | −1.43 | −0.4 | 1.32 |

Reactions were performed in 20 μl volumes using Quanti-Tect SYBR Green PCR master mix and 0.5 mM primers, according to manufacturer's instructions (www.qiagen.com). PCR cycling conditions optimised for P. falciparum cDNA were 95° C. for 15 min followed by 40 cycles of 94° C. for 30 sec, 54° C. for 40 sec, and 68° C. for 50 sec with a final extension at 68° C. for 10 min. Data acquisition was done at the end of elongation of each cycle. Specificity of amplification was ascertained by melting-curve analysis of each PCR product. Electrophoresis of PCR products and EB staining was performed and revealed no bands from no-template controls and single bands for all targets in cDNA PCR products. Quanti-fication was done using the Rotorgene software version 4.6 (www.qiagen.com). Transcription levels of the endogenous P. falciparum genes actin, seryl-tRNA synthetase and aldolase were analysed in order to determine the most accurate endogenous control. P. falciparum seryl-tRNA synthetase displayed the most uniform transcription profile in different parasite isolates and an unchanged pattern throughout the parasite life and was thus used for calculations of fold changes in var gene transcription by the ΔCT method (described in User Bulletin #2, Applied Biosystems, www.appliedbiosystems.com). Real-time PCR followed by calculating fold change in NF54-CSA compared to NF54 demonstrated marked upregulation of a single var transcript. The transcription of all other var genes was downregulated in the NF54-CSA compared to NF54 (FIG. 9). The upregulated var gene, called NF54var2csa, was also the most dominant var transcript when doing real-time PCR with the 54 var gene-specific primers. The upregulated and dominant NF54var2csa gene showed 50-100-fold higher level of expression following CSA selection both in ring-stage and trophozoite/schizont-stage NF54 parasites [Table 4]. Five additional primer sets targeting NF54var2csa sequences 3' to the original primer set (10, Table 3) were made and used in real-time PCR on cDNA from NF54 and NF54-CSA. Real-time PCR results were independent on which of these primer sets was used, i.e. for all the primer sets targeting NF43var2csa the gene showed upregulation in NF54 CSA compared to NF54 [Table 4].

Example 5

The NF54var2csa Gene that is Selectively Upregulated in P. fakiparum Isolate NF54 Following Selection for Adhesion to CSA in vitro has a Unique Sequence Structure and 5' Untranslated Region Among Var Genes All var genes are characterised by a two-exon structure. Exon 1 encodes a large extra-erythrocytic and highly variable region containing two to seven Duffy-binding like (DBL) domains and mostly one or two cysteine-rich inter-domain region (CIDR) domains. Based on sequence homologies, the DBL domains can be sub-divided into α, β, γ, δ, and ε types and the CIDR domains into CIDRα other (CIDR-O) types (Smith et al, 2000). A subset of var genes furthermore contains a second cysteine-rich domain called C2. Exon 2 encodes the intra-erythrocytic (cytoplasmic) and conserved part of the protein.

To date, one particular var gene (FCR3varCSA) encoding PfEMP1 domains with affinity for CSA has strongly been advocated as the central element in the pathogenesis of PAM (Buffet et al., 1999; Reeder et al., 1999; Douki et al., 2002; Vazquez-Macias et al., 2002). FCR3varCSA belongs to a sub-family of highly similar var genes (var1), present in many parasite genomes including that of NF54 (Rowe et al., 2002; Salanti et al., 2002). The var1 homologue in NF54 is the truncated pseudo-gene PFE1640w (Table 3).

Figure 10:
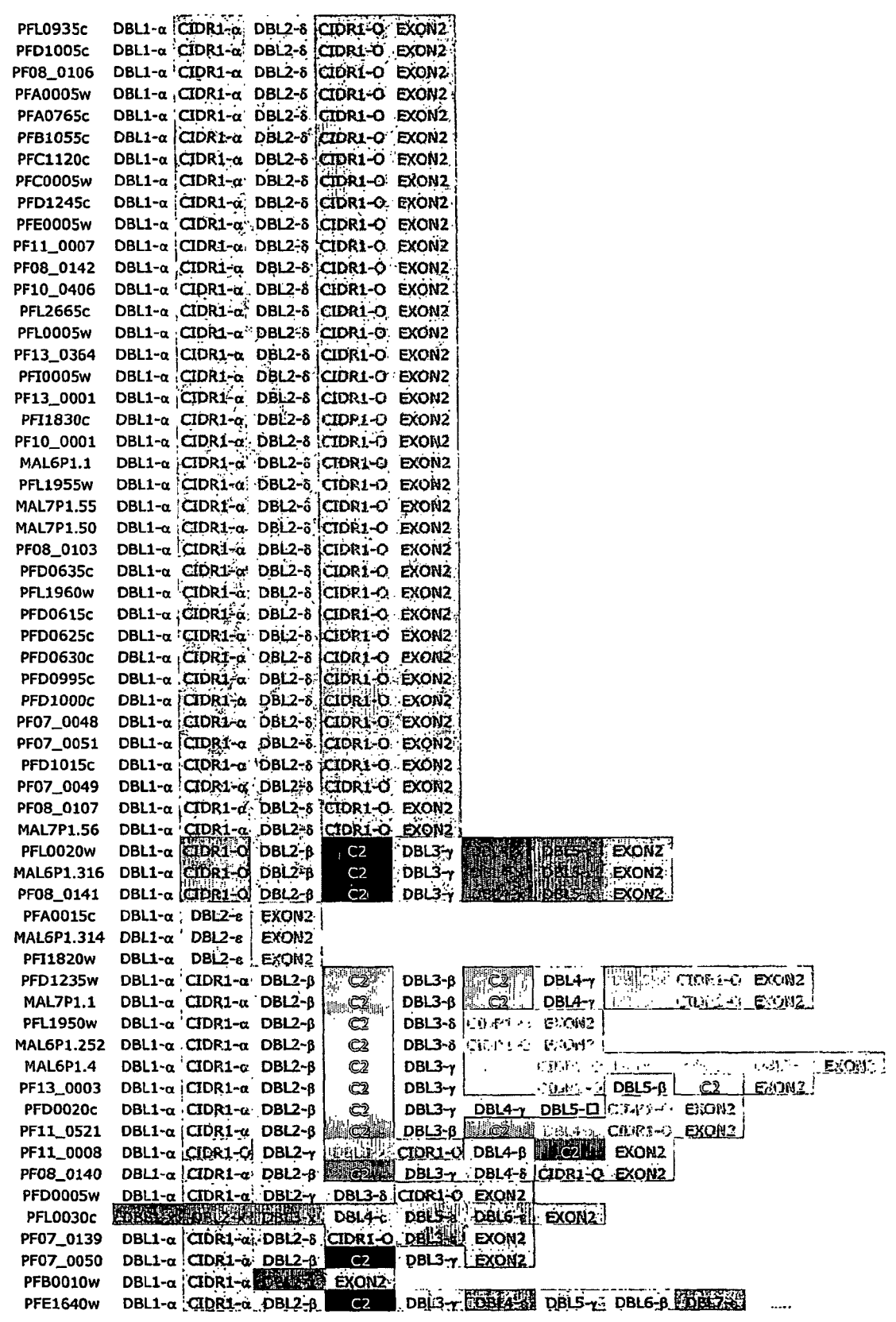

The entire genome of the P. falciparum clone 3D7 genome is now known, including its complete var gene repertoire. FIG. 10 shows the domain structure of each of the 59 var genes as well as the truncated pseudo-gene PFE1640w, and a NF54var2csa is the only var gene that does not encode a DBL1α domain. As in only three other var genes, a CIDR domain does not follow the first N-terminal DBL domain in NF54varcsa. NF54varcsa does not contain a DBL-γ domain, which is noteworthy as the previously described CSA adhesiveness of var1 PfEMP1 molecules has been mapped to DBL-γ domains (Buffet et al., 1999; Reeder et al., 1999). Finally, the three N-terminal DBL domains cannot be assigned to any of the existing DBL categories and are therefore termed DBL-x. Though other var genes contain domains that have been designated DBL-x, none have the NF54VAR2CSA domain structure of three successive DBL-x domains.

Figure 11:
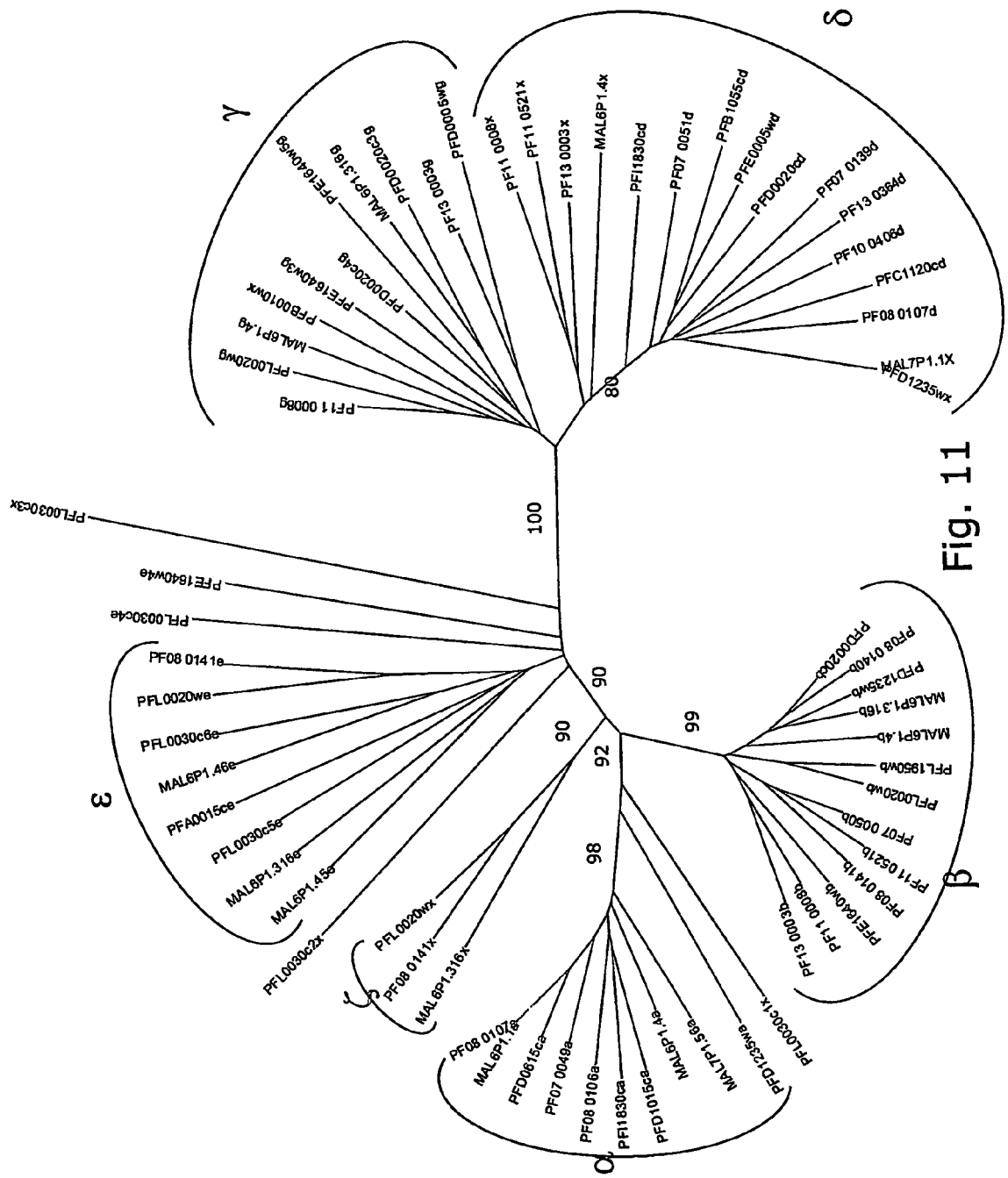

In order to investigate the relationship between DBL-x domains, a phylogenetic analysis of all DBL-x var gene domains in the 3D7 genome as well as 10 DBL-α, 10 DBL-β, 10 DBL-γ, 10 DBL-δ, and 10 DBL-ε domains from other 3D7 var genes was performed (FIG. 11). Two semi-conserved homology blocks were located in all DBL types. These blocks frame sequences of 150-300 amino acids, i.e., approximately 50% of a domain. The blocks were P(X/P)RR and P(Q/X)(F/X)(L/X)RW(E/.)EW, respectively. Phylogenetic trees were constructed using the ClustalW program with the neighbour-joining method and depicted in Jalview (www.ebi.ac.uk/clustalw).

As shown in FIG. 11, the DBL1-x domain of NF54VAR2CSA (PFL0030c1x) fits within the cluster of DBL1-α domains. Nevertheless, it appears to be distinct from these DBL1-α domains, as confirmed by separate phylogenetic analysis of all DBL1 domains over a longer sequence stretch (not shown). Although the NF54VAR2CSA DBL2-x domain (PFL0030c2x) is closer related to DBL-ε type domains than to other domain types, both this and the NF54VAR2CSA DBL3-x domain (PFL0030c3x) form independent clusters, when clustering is set to differentiate between DBL types (FIG. 11). The NF54VAR2CSA DBL4-ε domain (PFL0030c4e) forms a separate cluster, whereas the NF54VAR2CSA DBL5-ε (PFL0030c5e) and DBLε (PFL0030c6e) domains both cluster with other DBL-ε domains (FIG. 11).

Figure 12:
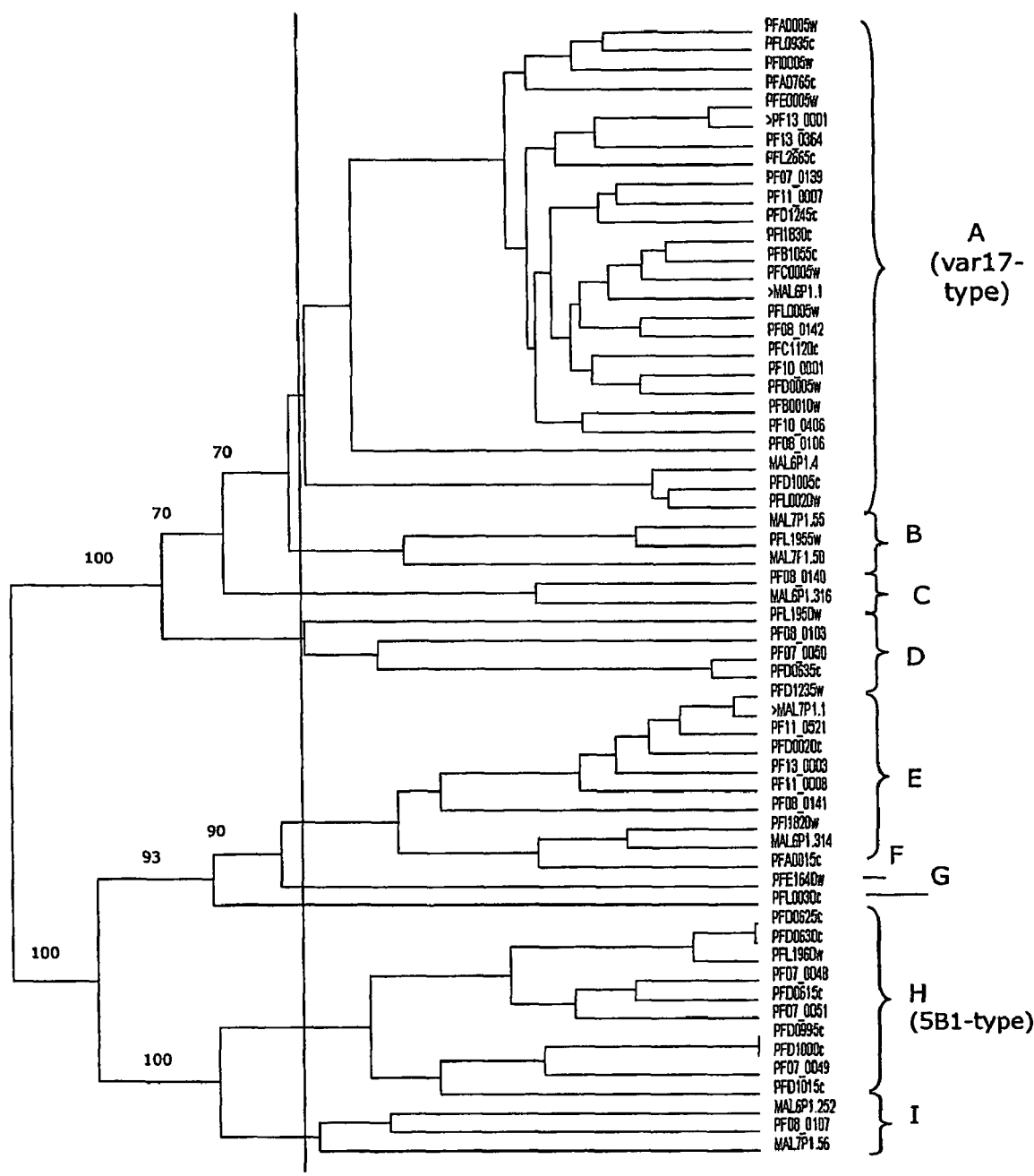

Further phylogenetic analysis of the 2 kb 5' un-translated regions (UTR) of all var genes as well as the var1 homologue PFE1640w (FIG. 12) confirmed the unique characteristics of NF54var2csa. It has previously been described that the var1 family is flanked by a distinct 5' UTR compared to two other 5' UTR regions (var17-type and var5B1-type) commonly found to flank var genes (Vazquez-Macias et al., 2002). In FIG. 12 the var17- and 5B1-types correspond to 5' UTR clusters A and H, respectively. In agreement with the above-mentioned report that var17 and 5B1 are common UTR regions, it was found that these two UTR regions flank the majority of var genes and primarily those with the most common domain structure (FIGS. 10 and 12). The 5' UTR of var1 was found to form an independent cluster consistent with its previous description (cluster F in FIG. 12). However, the most divergent 5' UTR (cluster G in FIG. 12) was that of NF54var2csa. In fact, no other hits were found to neither var1 nor NF54var2csa 5' UTR sequences in BLAST analysis (www.plasmodb.org) of the 3D7/NF54 genome (data not shown).

A detailed sequence identity search of exon1 of var2csa and VAR2CSA to other known sequences, primarily var and PfEMP1s was conducted.

By conducting a BLAST search under default conditions at the NCBI search engine and database we found following sequence identities to the var2csa and VAR2SCA exon1 sequences.

Throughout the amino acid sequence there was less than 80% amino acid identity in stretches down to 10 amino acids except at the following stretches (numbers relate to the transcription initiation codon of var2csa)

| From aa no | to aa no | length |
|---|---|---|
| 98 | 146 | 48 |
| 154 | 173 | 19 |
| 209 | 231 | 22 |
| 265 | 282 | 17 |
| 647 | 664 | 17 |
| 1131 | 1141 | 10 |
| 1366 | 1374 | 8 |
| 1760 | 1771 | 11 |
| 1675 | 1691 | 16 |
| 1604 | 1618 | 14 |
| 1563 | 1575 | 12 |
| 1188 | 1199 | 11 |
| 1535 | 1548 | 13 |
| 1276 | 1287 | 11 |
| 1481 | 1494 | 13 |
| 1415 | 1426 | 11 |
| 1319 | 1330 | 11 |
| 1858 | 1874 | 16 |
| 1903 | 1915 | 12 |
| 2172 | 2187 | 15 |
| 2026 | 2044 | 18 |
| 2090 | 2103 | 13 |
| 2142 | 2162 | 20 |
| 2420 | 2446 | 26 |
| 2361 | 2376 | 15 |
| 2463 | 2486 | 23 |
| 2269 | 2282 | 13 |

Throughout the amino acid sequence there was less than 90% amino acid identity in stretches down to 15 amino acids except at the following stretches (numbers relate to the transcription initiation codon of var2csa)

| From aa no | to aa no | length |
|---|---|---|
| 2505 | 2521 | 16 |
| 2549 | 2570 | 21 |
| 2638 | 2660 | 22 |

Throughout the amino acid sequence there was less than 90% amino acid identity in stretches down to 20 amino acids except at the following stretches (numbers relate to the transcription initiation codon of var2csa)

| From aa no | to aa no | length |
|---|---|---|
| 2602 | 2622 | 20 |

Throughout the nucleic acid sequence there was less than 80% amino acid identity in stretches down to 30 nucleic acids except at the following stretches (numbers relate to the transcription initiation codon of var2csa)

| from bp no | to bp no | |
|---|---|---|
| 7800 | 8001 | 90% ID over 70 bp |
| 601 | 660 | 90% ID over 40 bp |
| 1495 | 1540 | 90% ID over 30 bp |

Based on the above evidence it can be concluded that the NF54var2csa gene has a completely unique structure as expected for a gene encoding a VSA central to the pathogenesis of PAM. Furthermore, the NF54varcsa gene is flanked by a unique 5' UTR region, most likely containing a unique promoter for the gene.

Example 6

NF54var2csa Belongs to the var2csa Gene Sub-family that is Common and Highly Conserved in Many *P. falciparum* Isolates NF54var2csa is the dominant transcript and is highly upregulated in the *P. falciparum* isolate NF54 following selection for CSA adhesion (NF54-CSA; Example 4). All the 3D7 var genes differ from each other, but smaller blocks of sequences with high similarity are found in various var genes.

To date, only one sub-family of PfEMP1 has been defined (var1). Apart from the var1 sub-family, all PfEMP1 genes described so far from other parasite isolates differ from each other, and from the 3D7 var genes. It has therefore been assumed that the global repertoire of var genes is very large. This constitutes an obvious obstacle for the development of vaccines based on var genes and their products, as a high degree of conservation is a prerequisite for vaccine pan-reactivity.

Figure 13:
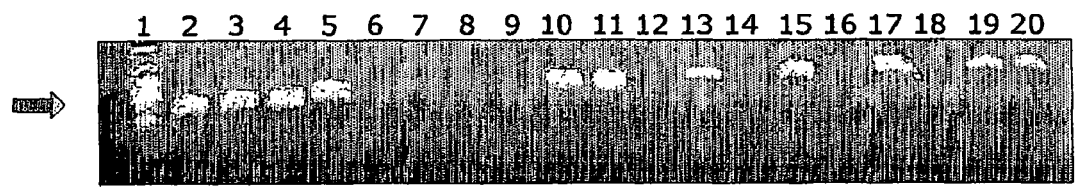

To test the degree of inter-genomic diversity of NF54var2csa, 19 different parasite isolates obtained from the peripheral blood of paediatric *P. falciparum* malaria patients were tested. Genomic DNA was isolated (www.clontech.com) using the NucleoSpin purification kits according to the manufacturer's recommendations. PCR was carried out in 0.2-ml microfuge tubes in a reaction volume of 20 μl using a PE2400 PCR machine (www.perkin-elmer.com). Final concentrations of the PCR reagents were as follows: Hotstart Taq polymerase (www.qiagen.com): 0.1 U; primers: 1 μM; dNTP: 2.5 mM, each; and $MgCl_2$: 1.5 mM). Cycling conditions were optimised for *P. falciparum* DNA: 15 min at 95° C. followed by 30 cycles of 30 sec at 94° C., 30 sec at 53° C., and 4 min at 68° C., with a final extension for 10 min at 68° C. The PCR products were visualised and size was determined in a 1% agarose gel containing EB. PCR amplification using NF54var2csa-specific primers (Table 1) on genomic DNA from 19 isolates from non-pregnant patients yielded a definite band of the expected size of 160 bp in 11 of the isolates (FIG. 13).

To demonstrate the extent of sequence similarity, 2,457 bp corresponding to 819 amino acids were cloned and sequenced. Gene-specific primers for NF54var2csa were used to perform PCR on genomic DNA from 2O2. PCR products were gel-purified using the Qiagen gel purification kit according to the manufacturer's instructions (www.qiagen.com). Purified PCR fragments were ligated into the pCRII TOPO vector using TOPO TA cloning kit, and TOP10 competent cells were transformed with the ligation mix (www.invitrogen.com). Positive clones were selected and propagated. Plasmid preparations were made using MiniPrep spin columns (www.qiagen.com).

Sequencing was performed on an ABI Prism 377 using the Big Dye terminator reaction mix (www.perkin-elmer.com). Proofreading and translation were done with ABI Prism software. It was found that 684 of 819 cloned from 2O2 were identical to the NF54var2csa sequence (FIG. 14).

In the same manner two different sets of NF54var2csa-specific primers (amplifying fragments of 309 bp and 264 bp, respectively) were used on genomic DNA from three other peripheral blood parasite isolates from children (BM033, BM074, and BM078), and four placental parasite isolates (Ej021, Ej023, Ej017, and Ej010). Alignments were done using ClustalW and a sequence similarity of 90-100% between NF54var2csa and the 7 parasite genes was found (FIG. 15).

Taken together, these data show that NF54var2csa belongs to a conserved and common gene family (var2) and thus fullfils two required criteria for any candidate gene in vaccine development.

Example 7

In Vitro Panning of *P. falciparum* Isolates on Chondroitin Sulphate A Results in Up-regulation of Var2csa but not of Var1 Genes The conserved var1 gene sub-family (Salanti et al., 2002) contains the FCR3varCSA gene that previously has been suggested as the gene encoding the mediator of CSA-specific placental parasite sequestration leading to PAM. To directly assess the likelihood that var1 genes and var2csa genes encode proteins that can be seen as vaccine candidates in the development of a vaccine against PAM, the change in transcription of var1 and var2csa genes in isogenic *P. falciparum* isolates was quantified before and after selection for adhesion to CSA in vitro. To this end, matched pairs of CSA-adhering and non-adhering 2O2 and FCR3 parasites (Example 3) were used. cDNA was made as described in Example 4 and real-time PCR was performed on this material using var1-specific and var2csa-specific primers (Table 3). The results showed that selection for adhesion to CSA resulted in up-regulation of var2csa homologues in all three of these well-characterised isolates, whereas transcription of var1 was unaffected by this procedure (Table 5).

TABLE 5

Fold change in transcription of var1 and var2csa induced by selection for adhesion to CSA matched pairs of genotypically distinct parasite isolates.

| Parasite | | Change (x) following selection | |
|---|---|---|---|
| Unselected | CSA-selected | var1 | var2csa |
| NF54 | NF54-CSA | 0.24 | 48.6 |
| 2O2 | 2O2-CSA | 1.4 | 6.2 |
| FCR3 | FCR3-CSA | 1.4 | 58.9 |

These results apart, it has been discovered that the 3D7 var1 gene homologue (PFE1640w) is truncated at the end of DBL7-ε and does not contain the expected gene intron or the exon 2 sequence. This indicates that CSA adhesion in NF54 is not mediated by a var1 homologue, as also suggested by the lack of upregulation of the gene (Table 5). Similarly, it has been shown that the FCR3CSA strain with a FCR3varCSA knockout genotype still could bind to CSA in vitro.

Taken together, these data show that in contrast to var1 genes, the transcription of var2csa genes is up-regulated in a range of CSA-adhering isolates having the characteristic serological phenotype indicating expression of $VSA_{PAM}$ antigens on the surface of IE.

Example 8

Transcription of var2csa is Higher in Placental Isolates than in Peripheral Blood Isolates from Children As described in previously examples, it was found that selection of *P. falciparum* for adhesion to CSA resulted in marked and specific upregulation of var2csa. Most placental parasite isolates adhere to CSA in vitro (Fried and Duffy, 1996) and express VSA that appear very similar or identical to those of CSA-selected parasites (Ricke et al., 2000; O'Neill-Dunne et al., 2001; Staalsoe et al., 2001).

TABLE 6

Levels of transcription of var2csa in three placental isolates (EJ010, EJ017, EJ024) and three peripheral blood parasites from children with malaria (BM033, BM074, BM078), normalised against seryl-tRNA synthetase. The NF54 isolate and the in vitro selected isolate NF54csa is included for comparison. ΔCt values were calculated as the Ct-var2csa minus Ct value of the housekeeping gene. Gene-specific primer set #75 (Table 3), made on the basis of gene alignment (FIG. 15) was used for the assaying.

| Parasite | Ct - var2csa | Ct - seryl-tRNA | ΔCt |
| --- | --- | --- | --- |
| NF54 | 32.1 | 23.2 | 8.9 |
| NF54-CSA | 25.5 | 21.7 | 3.8 |
| BM033 | 33.6 | 22.1 | 11.5 |
| BM074 | 32.5 | 18.7 | 13.8 |
| BM078 | none | 21.4 | >15 |
| EJ010 | 28.9 | 21.6 | 7.3 |
| EJ017 | 25.5 | 20.3 | 5.2 |
| EJ024 | 27.5 | 20.4 | 7.1 |

To further substantiate the merits of var2csa in a PAM-vaccine context, the levels of transcription of var2csa genes in parasite isolates obtained from the peripheral blood of non-pregnant individuals were compared to levels in placental parasites. Real-time PCR was performed with var2csa specific primers #75 (Table 3) and compared var2csa transcription to that of an endogenous control gene. Sequencing of the six var2csa examined is described in Example 6. The sequences from the three peripheral blood isolates from children (BM033, BM074, and BM078) and the three placental isolates (EJ010, EJ017, EJ024) were used to make one primer set specific for all 6 sequences (primer set #75; Table 3). RNA isolation, cDNA synthesis and real time PCR was performed as described in Example 6. As direct comparison between isogenic parasites was impossible in this case, real-time PCR was used to determine threshold level (Ct) values for var2csa and the house-keeping seryl-tRNA synthetase gene, and their difference (ΔCt) was calculated as a measure of the relative level of transcription of these two genes. Ct-seryl-tRNA synthetase values were consistently lower than Ct-var2csa values for all isolates tested, showing that seryl-tRNA synthetase was always transcribed at higher levels than var2csa. However, the ΔCt values were consistently lower among isolates from the placenta than among isolates from non-pregnant individuals, indicating less difference in transcription levels between seryl-tRNA and var2csa, and hence higher relative transcription of var2csa in the placental isolates (Table 5). This example shows that both parasites panned on CSA in vitro and placental parasites express var2csa at a quantitatively higher level than unselected and peripheral parasites from non-pregnant Individuals, respectively.

Example 9

Gender Specific and Parity Dependent Recognition of Synthetic VAR2CSA Peptides and Recombinant Fusion Proteins To make recombinant proteins of VAR2CSA the 3d7var2csa DBL1x,2x,3x,4x,5x,6x sub-cloned into the pGEX-4T1 vector by PCR using the following domain-specific oligonucleotide primers and a hot start taq polymerase (Qiagen) and PfuTurbo Stratagene):

```
DBL1x.Fw:
5'-C CCG GGA GTG CAG TAC TAT GGA AGT GGA-3',

DBL1x.Rv:
5'-G CGG CCG C CC ACC TTC CTT ACC AGA GGA-3'

DBL2x+.Fw:
5'-C CCG GGA TCA GAT GCT AAT AAT CCG TCT-3'

DBL2x+.Rv:
5'-G CGG CCG C GT TTC TCC ATC ACC TGA-3'

DBL2x.Rv:
5'-CG GAA TTC GTA CTT GCA TCT TTA ACT AAT-3'

DBL2x.Rv:
5'-G CGG CCG C GT TTC TCC ATC ACC TGA-3'

DBL3x.Fw:
5'-CGGAATTC GAC TGT AGT GAA CCT ATT TAT ATT-3'

DBL3x.Rv:
5'-AATTGCGGCCGCTTAAGCATTATTATATTCATAATA-3'

DBL4x.Rv:
5'-cg gaa ttc ata tgt tcg tgc gaa caa-3',

DBL4x.Rv:
5'-G CGG CCG C TC CAC ATC ATT CCA TTC-3',

DBL5x.Rv:
5'-cg gaa ttc gac gac aag agc aag atg aag-3',

DBL5x.Rv:
5'-G CGG CCG CAA ATC AGT CCA AGT ATC ATC-3'

DBL6x.Fw:
5'-CG GAA TTC GAT GAT ACT TGG ACT GAT TTG-3'

DBL6x.Rv:
5'-G CGG CCG CAG AAT GTC ACT GGT ATT-3'
```

The proteins encoding single domains were expressed as fusion proteins (*E. coli* strain BL21) at the carboxyterminus of glutathione S-transferase from *Schistosoma japonicum*, and purified by affinity chromatography on glutathione sepharose 4B (Amersham Pharmacia Biotech) (pGEX4-T1) in the absence of DTT and other reducing agents. To express VAR2CSA in eucaryotic organisms the exon1 ranging from nt 1 to 8000 was subjected to a full recodonisation:

An artificial codon table was generated by combining the codon usage of Trichoplusia ni and *Homo sapiens* genes. The codon bias of the synthetic VAR2CSA gene was adapted to this "artiflcial" codon usage table. In addition, regions of very high (>80%) or very low (<30%) GC content was avoided and the GC-content was adjusted to 50% where possible. During the optimization process following cis-acting sequence motifs were avoided:

internal TATA-boxes, chi-sites and ribosomal entry sites

AT-rich or GC-rich sequence stretches repeat sequences and RNA secondary structures (cryptic) splice donor and acceptor sites, branch points No reveres-complementary sequence identities longer than 20 nucleotides are found when the optimized sequence is aligned to the transcription of Homo sapiens. No RNA interference should therefore be expected. The entire gene was divided into and constructed as four ~2kb long fragments using PstI (2028), KasI (3759) and PvuII (5899) and cloned into pCR-Script-Amp (Stratagene, Calif., USA) Kpn1 and Sac1 restriction sites. The recodonised VAR2CSA exon1 sequence is listed as SEQ ID NO.: 3

The protein encoding 3d7var2csa DBL1x, DBL2x, Inter-domain2, DBL3x, DBL4x, DBL5x, DBL6x was expressed in Bachulo virus infected hi-fi insect cells and purified by HIS tag Metal Chelate Affinity Chromatography purification by cloning the domains into the pBlueBAc4.5/V5-His TOPA TA vector (Invitrogen) using the following primers:

```
DBL1x    GCC ATG GTG GAC AAG TCC TCC ATC
DBL1x    GAT GCA GGT CTT GTT GCT
DBL2x    GCC ATG GGC AAC AAG ACC TGC ATC
DBL2x    CTG CAC GCA CTT GTT CTC
ID2      GCC ATG GAG AAC AAG TGC GTG CAG
ID2      GCA GCC TCT GAT GTA GAT
DBL3x    GCC ATG GAG ATG AAG TCC TCC GAG
DBL3x    GTG GCA CAG GGA CTT GTT
DBL4x    GCC ATG GAT CTT GGA CTT GTC GTC
DBL4x    CAT CTT GGA CTT GTC GTC
DBL5x    GCC ATG GTG GAC AGA TGC TTC GAC
DBL5x    CTT GTT GCA GAT GTA GTC
DBL6x    GCC ATG GAA CAG GAA AGC GAT GGA
DBL6x    GAA CAG GAA AGC GAT GGA
```

These primers were used to clone all VAR2CSA domains into the pBlueBac4.5 transfer vector for high-level expression of the genes utilizing the polyhedrin promoter from Autographa califomica multi nuclear polyhedrosis virus. To obtain the genes as secreted proteins the domains was subcloned into the pBAD topo TA vector (Invitrogen) and cut out of this vector so that the V5 epitope and the polyhistidine tag is included in the fragment. This fragment was then cloned into the pAcGP67A Baculovirus transfer vector (BD Bioscience) for production of secreted recombinant VAR2CSA protein. This vector contains a 5' gp67 secretion signal sequence and a polyhedrin promoter for high level expression in virus infected insect cells An alignment of var2csa and the 58 other var genes from the PlasmoDB identifies a region of 28 amino acids in VAR2CSA dbl1-x with no sequence similarity to the other var genes. Blast search against GenBank also showed that this epitope is unique and is not contained in any other known protein.

The peptide consisting of H-LIDDMERHREECTSEDH-KSKEGTSYCST-OH was synthesised at Schaerfer-N (Denmark, Copenhagen) and dissolved in water and stored at −20° C. until use. This unique epitope and the recombinant VAR2CSA proteins was used to exemplify that VAR2CSA is better recognised by sera from multigravidae African women than sera from a mixed population of African men and women. For ELISA, the peptide and proteins was diluted in 0.1 M glycine/HCl (pH 2.75). The wells of Maxisorp micro titre plates (Nunc, Roskilde, Denmark) were coated with antigen (0.5 μg/well) by overnight incubation at 40C. The plates were emptied, and any residual binding capacity was blocked with 100 μl of blocking buffer (1% bovine serum albumin, 0.5 M NaCl, 1% Triton-X-100 in phosphate-buffered saline (PBS), pH 7.2) per well. After incubation for 0.5 h at room temperature, the plates were washed four times with washing buffer (PBS, 0.5 M NaCl, 1% Triton-X-100, pH 7.4) and 100 μl of plasma diluted 1:200 in blocking buffer was added to each well. The plates were then incubated for one hour at room temperature, and then washed and incubated for one more hour at room temperature with peroxidase-conjugated rabbit anti-human Immunoglobulin G (IgG) (Dako, Glostrup, Denmark) diluted 1:1000 in blocking buffer. Subsequently, the plates were washed and 100 μl of o-phenylenediamine substrate (0.6%, Dako) diluted in 0.1 M sodium citrate buffer (pH 5.0) with 0.05% (v/v) $H_2O_2$, was added to each well. Finally, the plates were incubated at room temperature in the dark before the addition of 100 μl of 2.5 M $H_2SO_4$ and the optical density (OD) was measured at 492 nm.

Figure 16:
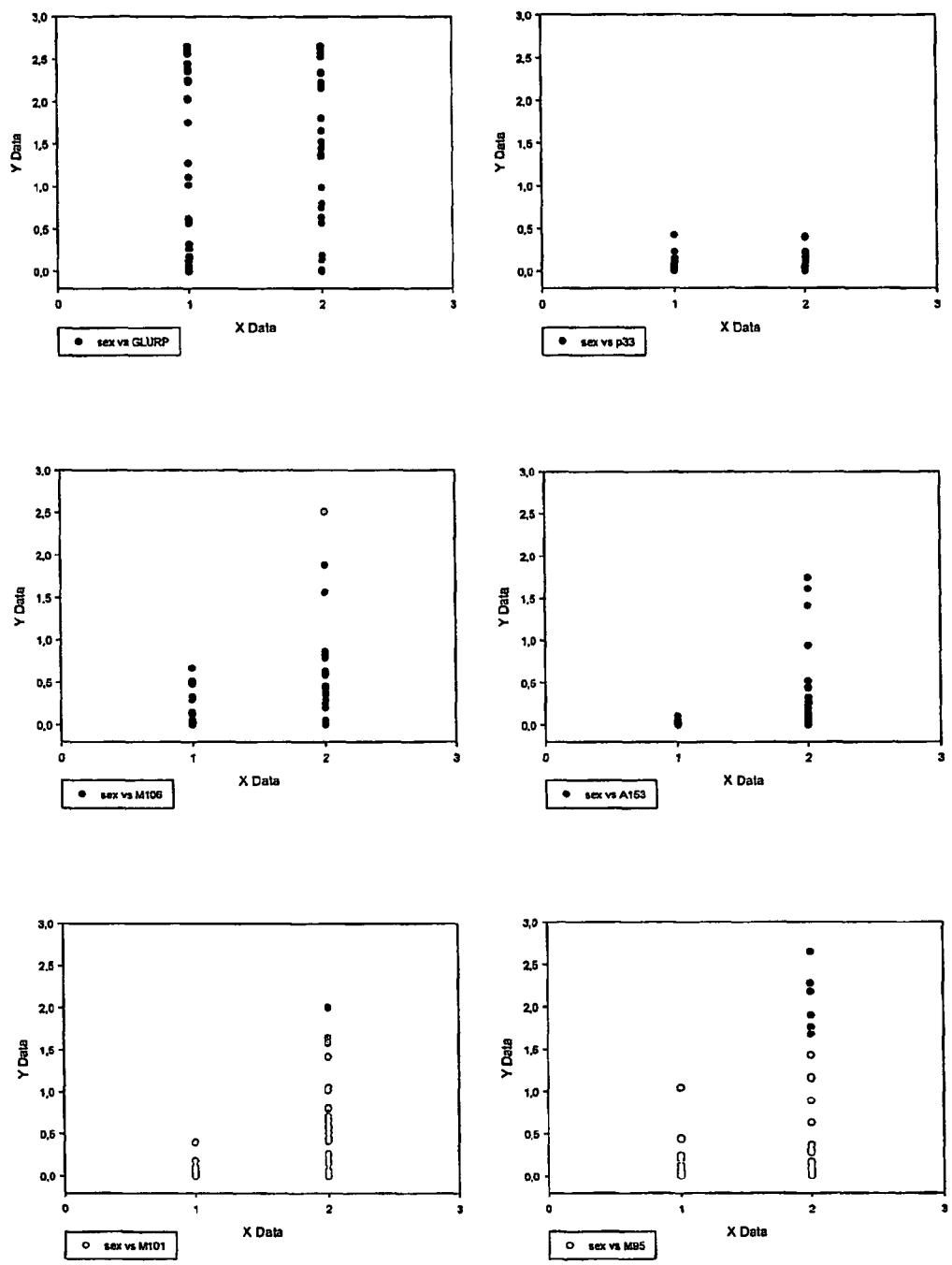

In this example we compare the level of IgG antibodies to the recombinant E. coli fusion proteins in plasma from 31 men and 27 delivering women living in Ghana. Four proteins were derived from VAR2CSA (DBL1, DBL4, DBL5 and DBL6, respectively) and two control proteins were derived from VAR1 (CIDR) and GLURP. As shown in attached figure (FIG. 16) IgG VAR2CSA levels were statistically significantly higher in the women than in the men (P between 0.035 and 0.002, Mann-Whitney) whereas the IgG levels to the two non-VAR2CSA malaria constructs were not (P=0.389 and P=0.53, for VAR1 and GLURP, respectively).

Figure 17:
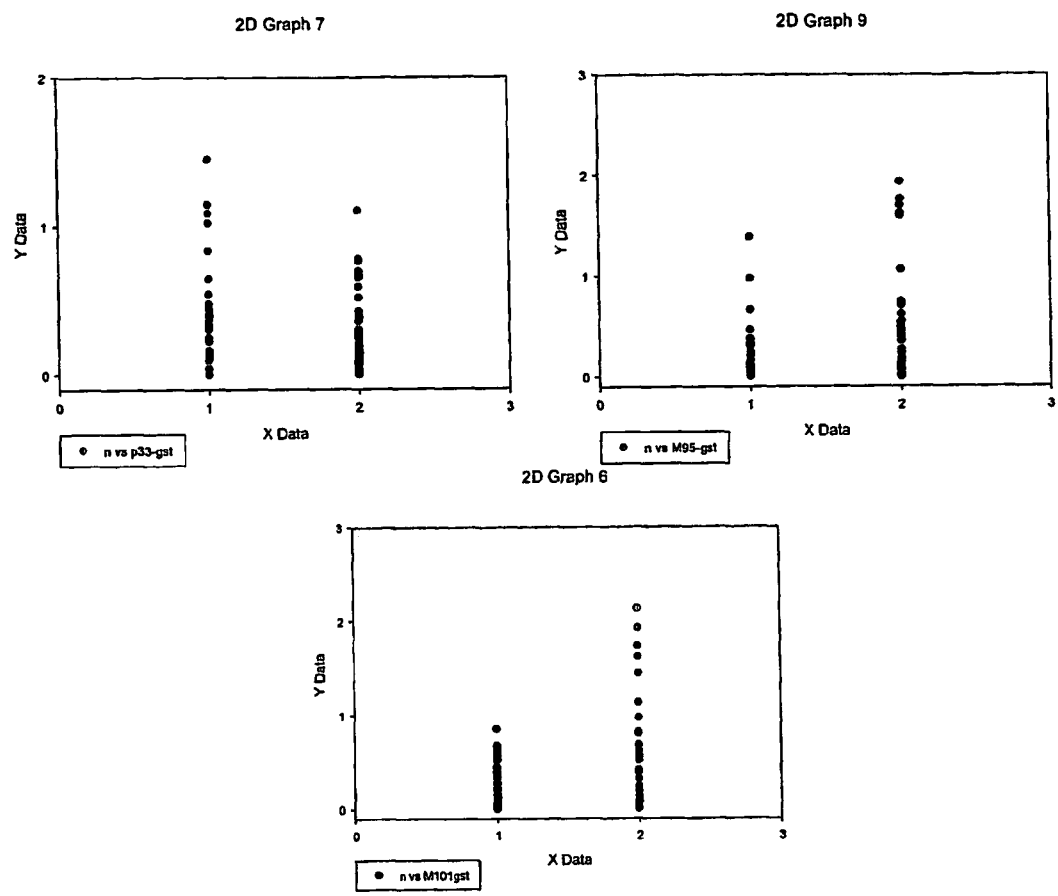

In this example we also compare the levels of antibodies among primigravidae and multigravidae Camerounian women. FIG. 17 shows that the levels of IgG to DBL5 and DBL4 of VAR2CSA were statistically significantly higher in multigravidae (P=0.041 and P=0.003, respectively), whereas the reactivity to CIDR-VAR1 was comparable in the two groups (P=0.56).

Example 10

Presence of antibodies against VAR2CSA domains is predictive of favorable birth outcome and delivering mothers hemoglobin levels In this example we measure the level of IgG antibodies to the recombinant VAR2CSA E. coli fusion proteins in plasma from African women and compare it to birth outcome. Production of recombinant proteins and ELISA was performed as described in the previously example.

The association between birth outcome and presence of VAR2CSA antibodies was Investigated in plasma antibodies from women delivering at Kilifi District Hospital, Kenya (Shulman et al., 2001). Haemoglobin and peripheral malaria slides were taken prior to delivery, placental biopsies and smears were taken at the time of delivery and birthweight and maternal height and weight were measured soon after birth. Information was obtained on socio-economic and educational status. The association between severe anaemia, birthweight, and antibody reactivity was investigated for women in whom the placental histology showed signs of acute and chronic malaria infection. These women have a high risk of complications due to PAM (Shulman and Dorman, 2003).

Table 7 shows that IgG levels to VAR2CSA were positively correlated. Furthermore IgG levels to VAR1 correlated negatively to birthweight in a linear regression model including DBL5VAR2 IgG levels (ELISA OD values DBL5), IgG levels to a VAR1 peptide (ELISA OD values to VAR1p), weight of mother (weightmot), mothers middle arm circumference (muacmot), the number of previous pregnancies (pregnumber), and the sex of the baby (sexn).

In a logistic regression model (table 8) including weightmot and muacmot, the odds ratio of giving birth to a low birth weight baby (below 2.500 g) was 0.20 (P=0.001) in women who had antibodies to DBL5 of VAR2CSA, as compared to women without these antibodies. Regression models including a range of other factors showed similar results (data not shown). The mean birth weight in women with and without DBL5 VAR2CSA antibodies were 2.852 g and 2.4935 g, respectively. This difference was statistical significant (mean difference and 95% CI, 359 g [118-601], P=0.004 two sample t-test).

The value of VAR1 and VAR2CSA antibodies was directly compared in a model including ELISA reactivity to two short peptides that by blast searches in Genebank represented sequences unique for the two respective proteins. Table 9 shows that the presence of antibodies to the VAR2CSA peptide was associated with a markedly reduced risk (odds ratio 0.05) of giving birth to a low weight baby, whereas the odds ratio for women having VAR1 antibodies was higher than 2, but not statistically significantly different from 1 (P=0.126).

The odds ration (table 10) for the mother having anaemia below 7 g/dl was 0.31 (95% CI 0.11-0.91, P=0.032) in women with DBL5VAR2CSA antibodies compared to those without such antibodies in a model including age of the mother, HIV status and number of pregnancies. Presence of VAR1 antibodies was not associated with anaemia.

The parasite load in the placenta was correlated to plasma antibody level in women who had a placental smear positive for malaria parasites. The placental parasites counts were negatively correlated to the level of antibodies against the VAR2CSA peptide ($R_s$=−0.24, p=0.037, spearman's rank order test), but not correlated to the level of antibodies to the VAR1CSA peptide ($R_s$=0.07, p=0.53 Sperman's rank order test). Furthermore, the median parasite load was lower in those with an antibody response to the VAR2CSA peptide than in those without such antibodies (median count and 10/90 percentiles, 6 [2-31] vs 16 [3-611], P<0.045).

Regression Data

TABLE 7

Linear regression model using birth weight as dependant variable and level of IgG plasma antibodies against DBL5 VAR2CSA (DBL5) and a VAR1 peptide (VAR1p), weight of mother, middle arm circumference of mother (muacmot) and number of previous pregnancies (pregnumber) and child gender (sexn) as independent variables in 110 women delivering at a hospital in Coastal Kenya in which a placental biopsy showed histological evidence of acute and chronic placental malaria infection {Shulman, Marshall, et al. 2001}. The relation between the birthweight and the individual parameters is shown below.
Table 7 Birthweight

| Parameter | Coef. | Std. Err. | P > |t| | [95% Conf. Interval] |
|---|---|---|---|---|
| DBL5 | 0.323 | 0.128 | 0.013 | 0.069-.577 |
| VAR1p | −0.682 | 0.248 | 0.007 | −1.17--.189 |
| weightmot | 0.0372 | 0.011 | 0.001 | 0.015-.059 |
| muacmot | −0.0926 | 0.040 | 0.022 | −0.172-.014 |
| pregnumber | 0.0772 | 0.040 | 0.058 | −0.003-.157 |
| sexn | 0.235 | 0.116 | 0.045 | 0.005-.464 |
| cons | 2.62 | 0.647 | 0.000 | 1.34-3.97 |

| Source | SS | df | MS |
|---|---|---|---|
| Model | 10.4 | 6 | 1.74 |
| Residual | 36.5 | 103 | .354 |
| Total | 46.9 | 109 | .430 |

Number of obs = 110
Prob > F = 0.0002
R-squared = 0.2224
Adj R-squared = 0.1771
Root MSB = .59532

Table 8. Logistic regression with low birth weight (below 2500 g) as dependant variable and presence/absence of antibodies against DBL5 VAR2CSA (DBL5pos), weight of mother (weightmot), middle arm circumference of mother (muacmot) as indepadant variables in 110 women delivering at a hospital in Coastal Kenya in which a placental biopsy showed histological evidence of acute and chronic placental malaria infection {Shulman, Marshall, et al. 2001}.

Number of obs=110; LR chi2(3)=22.25; Prob>chi2=0.0001 Log likelihood=−59.12; Pseudo R2=0.158

TABLE 8

Logistic regression with low birth weight (below 2500 g) as a dependant variable and presence/absence of antibodies against DBL5 VAR2CSA (DBL5pos), weight of mother (weightmot), middle arm circumference of mother (maucmot) as an independent variables in110 women delivering at a hospital in Coastal Kenya in which a placental biopsy showed histological evidence of acute and chronic malaria infection {Shulman, Marshall, et all. 2001}.
Table 8 Low birth weight

| Parameter | Odds Ratio | Std. Err. | P > |z| | [95% Conf. Interval] |
|---|---|---|---|---|
| DBL5pos | 0.200 | 0.099 | 0.001 | 0.076-0.527 |
| weigthmot | 0.852 | 0.047 | 0.003 | 0.765-0.949 |
| muacmot | 0.442 | 0.238 | 0.026 | 1.04-1.99 |

Number of obs = 110;
LR chi2(3) = 22.25;
Prob > chi2 = 0.0001;
Log likelihood = −59.12;
Pseudo R2 = 0.158

Figure 18:
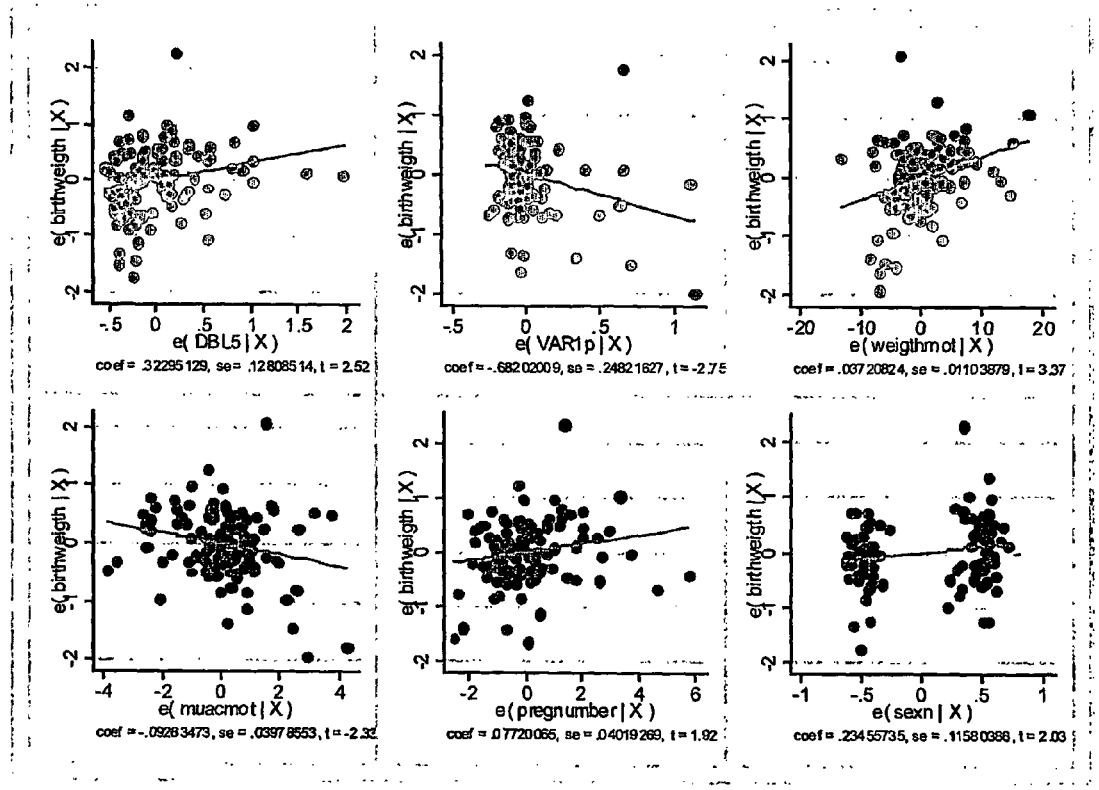

See also FIG. 18.

TABLE 9

Logistic regression with low birth weight (below 2500 g) as dependant variable and presence/absence of antibodies to peptides based on VAR2CSA and VAR1 (VAR2ppos or VAR1ppos, respectively), weight of mother (weightmot) and middle arm circumference (muacmot) as independent variables in117 women delivering at a hospital in Coastal Kenya in which a placental biopsy showed histological evidence of acute and chronic placental malaria infection.
Table 9 Low birth weight

| Parameter | Odds Ratio | Std. Err. | P > |z| | [95% Conf. Interval] |
|---|---|---|---|---|
| VAR2ppos | 0.058 | 0.067 | 0.014 | 0.006-0.560 |
| VAR1ppos | 2.125 | 1.037 | 0.123 | 0.816-5.53 |
| weightmot | 0.825 | 0.046 | 0.001 | 0.739-0.920 |
| muacmot | 1.472 | 0.235 | 0.016 | 1.076-2.014 |

Number of obs = 117;
LR chi2(4) = 25.19;
Prob > chi2 = 0.0000
Log likelihood = −61.88;
Pseudo R2 = 0.169

TABLE 10

Logistic regression with anaemia (below 7 g/dl) as dependant variable and presence/absence of antibodies to DBL5 VAR2CSA (DBL5pos), VAR1peptide (VAR1ppos), HIV status (HIVpos) and number of previous pregnancies (pregnumber) as independent variables in 109 women delivering at a hospital in Coastal Kenya in which a placental biopsy showed histological evidence of acute and chronic placental malaria infection.
Table 10 Anaemia

| Parameter | Odds Ratio | Std. Err. | P > |z| | [95% Conf. Interval] |
|---|---|---|---|---|
| DBLS5os | 0.294 | 0.153 | 0.019 | 0.106-0.817 |
| VAR1ppos | 2.06 | 1.18 | 0.209 | 0.667-6.35 |
| HIVpos | 2.67 | 1.93 | 0.174 | 0.647-11.02 |
| Pregnumber | 0.86 | 0.142 | 0.363 | 0.622-1.19 |

Number of obs = 109;
LR chi2(4) = 10.14;
Prob > chi2 = 0.038
Log likelihood = −54.81;
Pseudo R2 = 0.085

Example 11

Murine anti-VAR2CSA Antibodies

To generate antibodies against VAR2CSA, the domains were expressed and purified as described. The recombinant proteins and synthetic peptides were used to immunize Balb/c mice and Rabbit (5 μg, given subcutaneously in Freund's complete adjuvant followed by two 5 μg booster injections in Freund's incomplete adjuvant), the resulting immune sera reacted with the immunizing antigen when tested by Western blotting.

A DNA vaccination approach to generate antibodies to var2csa domains was also used. All domains was cloned into the Eucaryotic TA expression vector pCR3.1 (Invitrogen) using the following primers:

```
DBL1xfw     gcc atg g TG GAC AAG TCC TCC ATC

DBL1xrv     CTA GAT GCA GGT CTT GTT GCT

DBL2xfw     gcc atg g GC AAC AAG ACC TGC ATC

DBL2xrv     CTA CTG CAC GCA CTT GTT CTC

ID2fw       gcc atg g AG AAC AAG TGC GTG CAG

ID2rv       CTA GCA GCC TCT GAT GTA GAT

DBL3xfw     gcc atg g AG ATG AAG TCC TCC GAG

DBL3xrv     CTA GTG GCA CAG GGA CTT GTT

DBL4xfw     gcc atg g AT CTT GGA CTT GTC GTC

DBL4xrv     CTA CAT CTT GGA CTT GTC GTC

DBL5xfw     gcc atg g TG GAC AGA TGC TTC GAC

DBL5xrv     CTA CTT GTT GCA GAT GTA GTC

DBL6xfw     gcc atg g AA CAG GAA AGC GAT GGA

DBL6xrv     CTA GAA CAG GAA AGC GAT GGA
```

Plasmids were propagated in TOP10 cells (Invitrogen) and plasmid was purified using Plasmid GIGA prep kit (Qiagen). Plasmid DNA was injected IM to mice 4 times with 3 weeks intervals and finally boosted with the recombinant protein corresponding to the domain.

Figure 19:
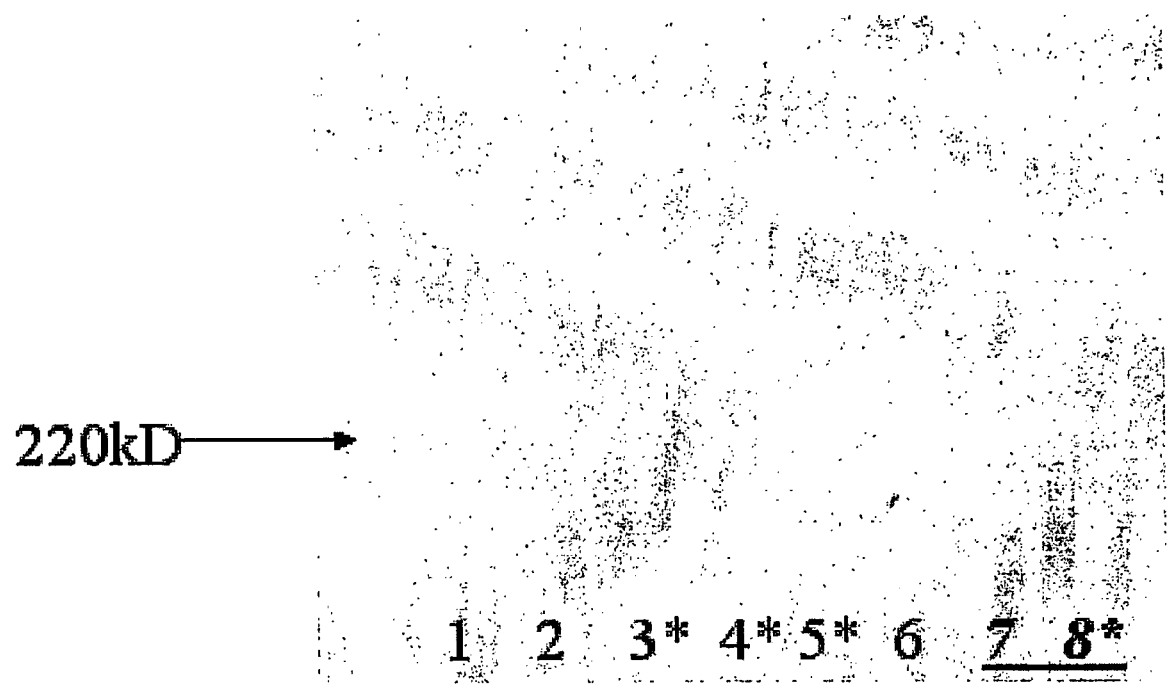

For detection of differential expression of VAR2CSA, total protein was extracted from unselected parasites and parasite, which had obtained the VSApam phenotype upon CSA selection. Western blotting was performed with antibodies raised against the conserved exon2 and against VAR2CSA. The attached figure (FIG. 19,) shows that VAR2CSA expression was upregulated in the two tested parasite lines (NF54 and FCR3) after CSA selection. Also confocal microskopi was used to determine that the VAR2CSA specific antibodies reacted with the surface of the infected erythrocytes, and only with erythrocytes infected with CSA selected parasites These antibodies against the recombinant VAR2CSA domains was tested for their ability to react with the surface of infected erythrocytes based on 1) flow cytometry, 2) wet IFA, and 3) confocal microscopy and we found that they reacted specifically with the surface of intact $VSA_{PAM}$ expressing infected erythrocytes and not to $VSA_{non-PAM}$ parasites, as defined below.

Parasites expressing $VSA_{PAM}$ are those that do not adhere to endothelial receptors such as CD36 and ICAM-1 but binds to glycosaminoglycans of intervillous space. $VSA_{PAM}$ is recognised by IgG of hyper-immune parous women, but by men (that do recognise $VSA_{nonPAM}$ at a level comparable to that of the women) relative to non-endemic control samples.

Parasites expressing $VSA_{non-PAM}$ are those that adhere to endothelial receptors such as CD36 and ICAM-1 and show little or no binding to glycoseaminoglycans of intervillous space. $VSA_{non-PAM}$ is recognised by IgG of both hyper-immune men and parous women and equally well by women of all parities after correction for age and parasite exposure.

Example 12

Anti-adhesion Assay

It is becoming increasingly apparent that acquired protective immunity to *P. falciparum* infection relies on Abs specifically recognizing variant parasite antigens expressed on the surface of late stage-infected erythrocytes. In this scenario, only parasites expressing variant antigens to which the host does not possess adequate specific Ab are likely to cause disease, and immunity is likely to depend on the accumulation of a large panel of Ab specificities recognizing different variants of such antigens. PAM is often associated with sequestration of large quantities of parasites in the placenta, even when peripheral parasitemia is scant. Placental parasites have been shown to adhere preferentially to CSA, while parasites from nonpregnant malaria patients rarely possess this phenotype. Furthermore, plasma from multigravid, but not primigravid, women from endemic areas can inhibit adhesion of placental parasites to CSA. It has previously been shown that levels of Abs to the CSA-specific isolate are strongly associated with parity and with the ability to inhibit parasite adhesion to CSA (Ricke et. al., 2000). The data point to interference with CSA-dependent sequestration as the basis for parity-dependent acquisition of anti-PAM immunity, and suggest it as a target for vaccination against PAM. To show that VAR2CSA is responsible for in vitro adhesion of NF54 parasites to CSA, an antibody adhesion assay with the murine antibodies against VAR2CSA was performed.

Antiadhesion was measured by $^3$H labeled parasites: For use in adhesion assays, parasite cultures with a parasitemia of ~1% late trophozoites and schizonts were first transferred from Albumax II medium (Life Technologies), with a high concentration of hypoxanthine (Hpx), into RPMI 1640 plus 5% normal human serum (low Hpx) and maintained for 24 h. The parasites then were labeled by exposure to [3H]Hpx (Amersham; 8.75 MBq/mL of RBCs) for another 24 h. Finally, the cultures were enriched for late-stage iRBCs and Incubated for 30 min, with or without test plasma. Microtiter plates (Falcon; Becton Dickinson) were coated with CSA or HA (50 μg/mL, 100 μL/well; Sigma) overnight at 5° C. In a wet chamber and then blocked with bovine serum albumin (BSA; 20 mg/mL, 100 μL/well) in PBS at room temperature for 30 min. We added enriched [$^3$H]Hpx-labeled late-stage iRBCs to CSA-coated wells (2×106 cells/well) and incubated the wells at 37° C. for 1 h. Nonadherent iRBCs were removed by 4 washes in RPMI 1640. Adherent iRBCs were harvested onto glass fiber pads, and the [$^3$H]Hpx activity was measured in a liquid scintillation counter (Beckman Coulter). Inhibition of iRBC adhesion by plasma was calculated as 1−(testCSA−controlBSA)/controlCSA−controlBSA), where testCSA is counts per minute of iRBCs preincubated with plasma and adhering to CSA-coated wells, and controlCSA and controlBSA refer to counts per minute of iRBCs not preincubated with plasma and adhering to CSA- and BSA-coated wells, respectively.

Cytoadhesion of NF54-CSA was significantly inhibited by plasma from multigravid woman, and more importantly binding of NF54CSA to CSA was strongly inhibited by the anti-VAR2CSA antibodies. In this example it is shown that antibodies raised against recombinant VAR2CSA inhibit parasite adhesion to CSA in vitro. An obvious consequence of this finding is that vaccine induced antibodies against VAR2CSA constructs can hinder binding of parasites to placental tissue and thus prevent pregnancy-associated malaria.

The same antibodies were also found to inhibit binding of parasites to culture grown syncytiotrophoblasts. Inhibition assays were also done using short time cultured placental tissue. Placentas were obtained from the maternity ward at Copenhagen University Hospital (Rigshospitalet) and trophoblasts isolated from placental tissue using DNAse and trypsin followed by Percoll gradient centrifugation. Trophoblasts were cryopreserved or directly cultured on plastic plates in a medium containing epidermal growth factor. After 5 days the cells developed into syncytiotrophoblasts and used for parasite binding assays for a period of approximately 5 days. I was found that the antibodies that inhibited the homologue parasite NF54CSAs binding to CSA also inhibited binding of placental isolates to the cultured syncytiotrophoblasts To further study CSA adhesion all domains were cloned into the pDISPLAY vector (Invitrogen) using the following primers:

```
DBL1xfw    CC CCC GGG ATG GAG AAG TCC TCC ATC

DBL1xrv    TCC CCG CGG GAT GCA GGT CTT GTT GCT

DBL2xfw    CC CCC GGG AGC AAC AAG ACC TGC ATC

DBL2xRv    TCC CCG CGG CTG CAC GCA CTT GTT CTC

ID2fw      CC CCC GGG GAG AAC AAG TGC GTG CAG

ID2rv      TCC CCG CGG GCA GCC TCT GAT GTA GAT

DBL3xfw    CC CCC GGG AAG ATG AAG TCC TCC GAG

DBL3xRv    TCC CCG CGG GTG GCA CAG GGA CTT GTT

DBL4xfw    CC CCC GGG CAG GTG AAG TAC TAC GAA

DBL4xRv    TCC CCG CGG CAT CTT GGA CTT GTC GTC

DBL5xfw    CC CCC GGG CTG GAC AGA TGC TTC GAC

DBL5xRv    TCC CCG CGG CTT GTT GCA GAT GTA GTC

DBL6xfw    CC CCC GGG ATC TAC AGG CTG AAG CAC

DBL6xRv    TCC CCG CGG GAA CAG GAA AGC GAT GGA
```

The ability of the different domains to bind directly to CSA has in this example been assayed using a mammalian expression system. Domains was cloned into the pDisplay vector (Invitrogen). This vector allows display of cloned proteins on the cell surface. Each domain will be fused at the N-terminus to the murine Ig κ-chain leader sequence, which targets the protein to the cell surface, and at the C-terminus to the platelet derived growth factor receptor (PDGFR) transmembrane domain, which anchors the protein to the cell membrane. A human non-adherent T cell and a CHO cell line was used for transient expression of the recombinant proteins. This approach have enabled us to study cell adhesion to CSA.

Example 13

Identification of CSA Binding Sites in Silico and in Vitro

We identified positively charged egions exposed at the surface which could participate in the binding of GAGs. This approach requires information pertaining to the secondary structure of the protein, so the predictive Chou-Fasman algorithm was employed to analyze the VAR2CSA protein sequence. The Chou-Fasman algorithm contained in the Protean v. 3.07a module of the DNAstar analysis package (Madison, Wis.) reports the regions containing alpha helices, beta sheets, and reverse turns, positively and negatively charged regions, and those regions likely to be exposed at the surface. Parameters used in the algorithm were as follows: α-helix threshold 103, β-strand threshold 105. Following this the entire sequence was examined for putative GAG binding motifs. Subsequent searches were performed using well-characterized motifs found to exist in several other proteins which do not exactly fit the pre-defined models. The identified potential GAG binding sites were further inspected for the likelihood of surface exposure. Eight classic Cardin-Weintraub motifs and eight variations on these motifs were identified. The foremost secondary structural element in GAG binding motifs is the presence of reverse turns. Regions that are rich in turns may loop a portion of the protein onto the surface forming a cup of positive charge that can align appropriately to interact electrostatically with GAGs. However, some known GAG binding sites do not contain reverse turns. Examples include Apo E, laminin, and protein C inhibitor. In the var2csa protein, most of the predicted sites contain predicted reverse turns, although five do not. To determine the likelihood that these identified motifs could participate in GAG protein interactions, regions at the surface of the proteins were examined. All of the putative binding sites appear to be sufficiently accessible to participate in GAG protein interactions.

To study the GAG (CSA) binding sites in vitro we made mini library of var2csa in bacteriophage lamda using EcorR1/HindIII arms contained in the T7Select system (Novagen). The T7Select415 vector was chosen for high-copy number display of small peptides (50aa). For amplifying the library a plate lysate was made and a subsequent plaque assay to determine titer. The VAR2CSA peptide library was screened by biopanning on ELISA plates coated with CSA (SIGMA). Elution was performed with different elution buffers, in this example the T7 elution buffer (Novagen). To determine whether enrichment has occurred after the biopanning, 4 simultaneously biopanning reactions were set up and each was biopanned 5 times. After the 5× biopanning the lysate was titered and plated at low density (100 pfu/plate). 50 well spaced plaques was picked and PCR amplified using the T7SelectUP primer and T7SelectDOWN primer and sequenced using the same primers on an ABI Prism 377 (Perkin Elmer) using the Big Dye Terminator (Perkin Elmer) reaction mix and ABI Prism proofreading and translation software.

In this example we report the sequences that were found to bind CSA both in silico and in vitro:

Amino acid range of the found epitope given from the start methionine of the VAR2CSA is indicated in parentheses

| | |
|---|---|
| (2115-2122) | IKRKLDRL |
| (1716-1723) | TKRARTDW |
| (843-851) | DAKRNRKAG |

-continued

| (2462-2469) | KRKKWWDM |
| (2385-2393) | CKYKRDPKL |
| (2404-2412) | SEVERLKKV |
| (454-464) | IKANKKKVCKH |
| (2003-2012) | GCKHKTKLDE |
| (2241-2249) | EGYKKYKGM |
| (1190-1200) | EKKCKENESTN |
| (1415-1424) | KINKKQKKNG |
| (595-603) | EKGKKTQEL |
| (321-328) | CKDKCKKY |
| (332-340) | VKKWKSEWE |
| (2667-2677) | MKKKPKTP |
| (1764-1769) | EKEKKKPNE |
| (1484-1498) | KRKCEEYKKYISEKK |
| (2223-2132) | KKYQEWSRKR |
| (2036-2053 | RRRQLCFSRIVRGPANLR |

REFERENCES

Brabin, B. J. 1983 An analysis of malaria in pregnancy in Africa Bull World Health Organ 61: 1005-1016.

Buffet, P. A., Gamain, B., Scheidig, C., Baruch, D., Smith, J. D., Hernandez-Rivas, R. et al. 1999 Plasmodium falciparum domain mediating adhesion to chondroitin sulfate A: a receptor for human placental infection Proc Natl Acad Sci U S A 96: 12743-12748.

Duffy, P. E., Fried, M. 1999 Malaria during pregnancy: parasites, antibodies and chondroitin sulphate A Biochem Soc Trans 27: 478-482.

Fried, M., Duffy, P. E. 1996) Adherence of Plasmodium falciparum to chondroitin sulphate A in the human placenta Science 272: 1502-1504.

Fried, M., Nosten, F., Brockman, A., Brabin, B. T., and Duffy, P. E. 1998 Maternal antibodies block malaria Nature 395: 851-852.

Gardner, M. J., Hall, N., Fung, E., White, O., Berriman, M., Hyman, R. W. et al. 2002 Genome sequence of the human malaria parasite Plasmodium falciparum Nature 419: 498-511.

Lavstsen, T., Salanti, A., Jensen, A. T. R., Arnot, D. E., and Theander, T. G. (2003). Sub-grouping of Plasmodium falciparum 3D7 var genes based on sequence analysis of coding and non-coding regions. Malar. J. 2.

O'Neill-Dunne, I., Achur, R. N., Agbor-Enoh, S. T., Valiyaveettil, M., Naik, R. S., Ockenhouse, C. F. et al. 2001 Gravidity-dependent production of antibodies that inhibit binding of Plasmodium falciparum-infected erythrocytes to placental chondroitin sulfate proteoglycan during pregnancy infect immun 69: 7487-7492.

Ricke, C. H., Staalsoe, T., Koram, K., Akanmori, B. D., Riley, E. M., Theander, T. G., and Hviid, L. 2000 Plasma antibodies from malaria-exposed pregnant women recognize variant surface antigens on Plasmodium falciparum-infected erythrocytes in a parity-dependent manner and block parasite adhesion to chondroitin sulphate A J Immunol 165: 3309-3316.

Robinson, B. A., Welch, T. L., and Smith, J. D. (2003). Widespread functional specialization of Plasmodium falciparum erythrocyte membrane protein 1 family members to bind CD36 analysed across a parasite genome. Mol. Microbiol. 47, 1265-1278.

Salanti, A., Jensen, A. T. R., Zornig, H. D., Staalsoe, T., Joergensen, L., Nielsen, M. A. et al. 2002 A sub-family of common and highly conserved var genes expressed by CSA-adhering Plasmodium falciparum Mol Biochem Parasitol 122: 111-115.

Salanti, A., Staalsoe, T., Lavstsen, T., Jensen, A. T., Sowa, M. P., Arnot, D. E., Hviid, L., and Theander, T. G. (2003). Selective upregulation of a single distinctly structured var gene in chondroltin sulphate A-adhering Plasmodium falciparum involved in pregnancy-associated malaria. Mol Microbiol 2003. Jul. ;49. (1):179.-91. 49, 179-191.

Shulman, C. E., Marshall, T., Dorman, E. K., Bulmer, J. N., Cutts, F., Peshu, N., and Marsh, K. 2001 Malaria in pregnancy: adverse effects on haemoglobin levels and birthweight in primigravidae and multigravidae Trop Med Int Health 6: 770-778.

Smith, J. D., Chitnis, C. E., Craig, A. G., Roberts, D. J., Hudson-Taylor, D. E., Peterson, D. S., Pinches, R., Newbold, C. I., and Miller, L. H. (1995). Switches in expression of Plasmodium falciparum var genes correlate with changes in antigenic and cytoadherent phenotypes of infected erythrocytes. Cell 82, 101-110.

Smith, J. D., Subramanian, G., Gamain, B., Baruch, D. I., and Miller, L. H. (2000). Classification of adhesive domains in the Plasmodium falciparum erythrocyte membrane protein 1 family. Mol Biochem. Parasitol. 2000. Oct. ;110. (2): 293.-310.110, 293-310.

Staalsoe, T., Megnekou, R., Flevet, N., Ricke, C. H., Zornig, H. D., Leke, R. et al. 2001 Acquisition and decay of antibodies to pregnancy-associated variant antigens on the surface of Plasmodium falciparum infected erythrocytes that are associated with protection against placental parasitemia J Infect Dis 184: 618-626.

Staalsoe et al. 1999 Detection of Antibodies to Variant Antigens on Plasmodium falciparum-Infected Erythrocytes by Flow Cytometry Cytometry 35: 329-336.

Wahlgren, M., Fernandez, V., Chen, Q. J., Svärd, S., and Hagblom, P. 1999 Waves of malarial variations Cell 96: 603-606.

The invention claimed is:

1. An isolated polypeptide comprising an amino acid sequence that is at least 90% identical to a sub-sequence of SEQ ID NO:2 with a minimum length of 100 amino acids, wherein said amino acid sequence
   (i) does not comprise a cysteine-rich inter-domain region (CIDR) domain or Duffy-binding like-γ (DBL-γ) domain, and
   (ii) comprises (a) at least one B-cell epitope, (b) at least one T-cell epitope, or (c) at least one B-cell epitope and at least one T-cell epitope, and
   (iii) is capable of inducing an immune response against a molecule expressed on the surface of an intact erythrocyte infected by a placental parasite.

2. An isolated polypeptide according to claim 1, wherein said sub-sequences comprise one or more glycos-amino glucans-binding motifs.

3. An isolated polypeptide according to claim 1, wherein said amino acid sequence is gender specifically recognised.

4. An isolated polypeptide according to claim 1, wherein said amino acid sequence is recognised in a parity dependent manner.

5. An immunogenic composition comprising an isolated polypeptide according to claim 1.

6. An immunogenic composition according to claim 5, said composition characterised in that it induces an IgG/IgM antibody response.

7. An in vitro diagnostic kit comprising:

1) An isolated polypeptide comprising an amino acid sequence that is at least 90% identical to -a sub-sequence of SEQ ID NO:2 with a minimum length of 100 amino acids and wherein said sub-sequence comprises (a) at least one B-cell epitope, (b) at least one T-cell epitope, or (c) at least one B-cell epitope and at least one T-cell epitope;

2) reagents for preparing a suitable medium for carrying out a reaction between an IgG/antibody present in a sample of body fluid or tissue and said sequence, and
3) reagents allowing the detection of the antigen-antibody complexes formed;

wherein said reagents may bear a radioactive or non-radioactive label.

* * * * *